United States Patent
Bonora et al.

(10) Patent No.: US 10,092,929 B2
(45) Date of Patent: Oct. 9, 2018

(54) WAFER TRAY SORTER WITH DOOR COUPLED TO DETECTOR

(71) Applicant: Brooks Automation, Inc., Chelmsford, MA (US)

(72) Inventors: Anthony C. Bonora, Portola Valley, CA (US); Brian Compian, Cupertino, CA (US); Jeff P. Henderson, Campbell, CA (US); Robert W. Carlson, Milpitas, CA (US)

(73) Assignee: Brooks Automation, Inc., Chelmsford, MA (US)

( * ) Notice: Subject to any disclaimer, the term of this patent is extended or adjusted under 35 U.S.C. 154(b) by 3 days.

(21) Appl. No.: 15/386,799

(22) Filed: Dec. 21, 2016

(65) Prior Publication Data

US 2017/0100750 A1 Apr. 13, 2017

Related U.S. Application Data

(62) Division of application No. 13/830,692, filed on Mar. 14, 2013, now Pat. No. 9,545,724.

(51) Int. Cl.
  *H01L 21/677* (2006.01)
  *B07C 5/34* (2006.01)
  (Continued)

(52) U.S. Cl.
  CPC .............. *B07C 5/3412* (2013.01); *B07C 5/00* (2013.01); *B25J 15/0028* (2013.01); *B25J 15/022* (2013.01); *G01N 35/04* (2013.01); *H01L 21/67271* (2013.01); *H01L 21/67721* (2013.01); *H01L 21/67766* (2013.01); *H01L 21/67772* (2013.01); *H01L 21/67778* (2013.01);
  (Continued)

(58) Field of Classification Search
  None
  See application file for complete search history.

(56) References Cited

U.S. PATENT DOCUMENTS 6,013,920 A * 1/2000 Gordon ............. H01L 21/67265
   250/559.33
6,188,323 B1 * 2/2001 Rosenquist ....... H01L 21/67265
   340/686.5
(Continued)

FOREIGN PATENT DOCUMENTS

CN  1216285 A  5/1999
JP  H0826418 A  1/1996
(Continued)

*Primary Examiner* — Gerald McClain
(74) *Attorney, Agent, or Firm* — Martine Penilla Group, LLP

(57) ABSTRACT

A tray engine includes a vertical drive column, a rotation mechanism for rotating the vertical drive column, and an end effector attached to the vertical drive column. The end effector includes an end effector base attached to the vertical drive column. The end effector further includes a slide attached to the end effector base to support a tray, when present. The slide enables the tray to slide along a length of the end effector base. The tray engine includes a drive mechanism attached to the end effector base for moving along the length of the end effector base to enable the tray, when present, to slide linearly along the length and load or unload the tray to or from the slide.

5 Claims, 58 Drawing Sheets

(51) Int. Cl.
  *B07C 5/00* (2006.01)
  *B25J 15/00* (2006.01)
  *B25J 15/02* (2006.01)
  *H01L 21/67* (2006.01)
  *H01L 21/687* (2006.01)
  *G01N 35/04* (2006.01)

(52) U.S. Cl.
  CPC .. *H01L 21/67781* (2013.01); *H01L 21/68707* (2013.01); *B07C 2501/0063* (2013.01); *G01N 2035/0418* (2013.01); *G01N 2035/0425* (2013.01)

(56) References Cited

U.S. PATENT DOCUMENTS

| | | | |
|---|---|---|---|
| 6,396,072 B1* | 5/2002 | Meyhofer | G06M 1/101 250/239 |
| 6,452,201 B1* | 9/2002 | Wang | H01L 21/67265 250/559.29 |
| 6,591,162 B1* | 7/2003 | Martin | H01L 21/67242 700/225 |
| 6,799,521 B2 | 10/2004 | Tai et al. | |
| 6,984,839 B2* | 1/2006 | Igarashi | G01V 8/12 250/559.28 |
| 7,066,707 B1 | 6/2006 | Bonora et al. | |
| 7,192,791 B2* | 3/2007 | Hofmeister | H01L 23/544 257/618 |
| 7,648,327 B2 | 1/2010 | Bonora et al. | |
| 8,454,293 B2* | 6/2013 | Gilchrist | H01L 21/67772 414/217 |
| 8,821,099 B2* | 9/2014 | Hall | H01L 21/67775 118/500 |
| 9,239,228 B2* | 1/2016 | Natsume | G01B 11/002 |
| 9,496,161 B2* | 11/2016 | Johnson | H01L 21/67769 |
| 9,514,974 B2* | 12/2016 | Sharrock | H01L 21/681 |
| 2002/0023444 A1 | 2/2002 | Felder et al. | |
| 2003/0119214 A1* | 6/2003 | Kitazawa | H01L 21/67265 438/5 |
| 2003/0229416 A1 | 12/2003 | Tai et al. | |
| 2006/0120833 A1 | 6/2006 | Bonora et al. | |
| 2006/0177289 A1* | 8/2006 | Bonora | H01L 21/67766 414/217 |
| 2007/0009345 A1* | 1/2007 | Hall | H01L 21/67775 414/222.01 |
| 2010/0034621 A1* | 2/2010 | Martin | H01L 21/67265 414/217.1 |
| 2010/0172721 A1* | 7/2010 | Gilchrist | H01L 21/67772 414/217 |
| 2011/0158774 A1* | 6/2011 | Yamaguchi | H01L 21/67265 414/222.02 |
| 2015/0010379 A1* | 1/2015 | Sharrock | H01L 21/681 414/292 |
| 2015/0022821 A1* | 1/2015 | Mazzocco | H01L 21/67259 356/601 |
| 2015/0214079 A1* | 7/2015 | Eom | H01L 21/67778 134/56 R |
| 2017/0084476 A1* | 3/2017 | Sharrock | H01L 21/681 |
| 2018/0040494 A1* | 2/2018 | Rebstock | H01L 21/67265 |

FOREIGN PATENT DOCUMENTS

| | | |
|---|---|---|
| JP | 2005255327 A | 9/2005 |
| JP | 2011124591 A * | 6/2011 |
| JP | 2011228633 A | 11/2011 |
| WO | 8404723 A1 | 12/1984 |

* cited by examiner

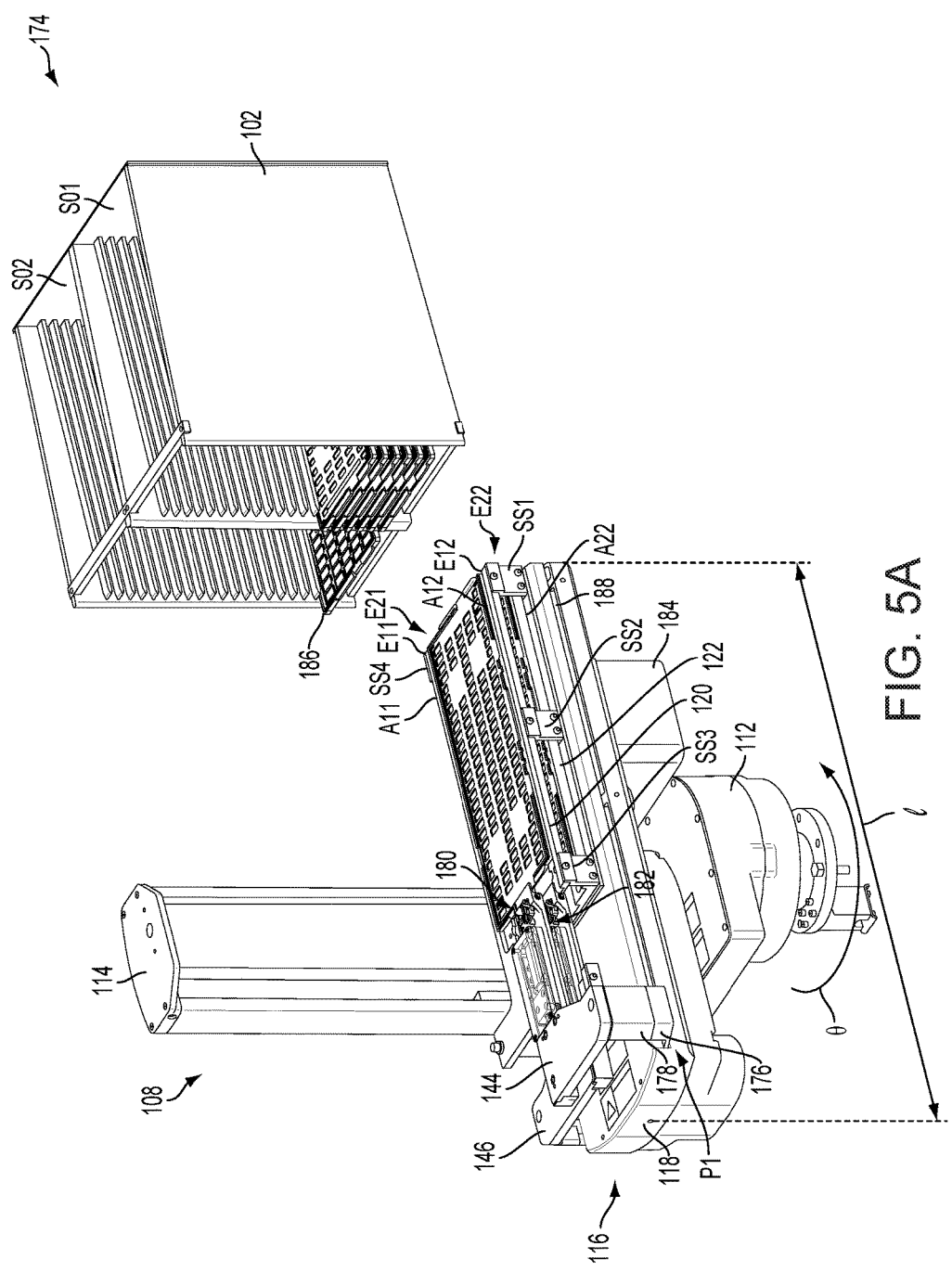

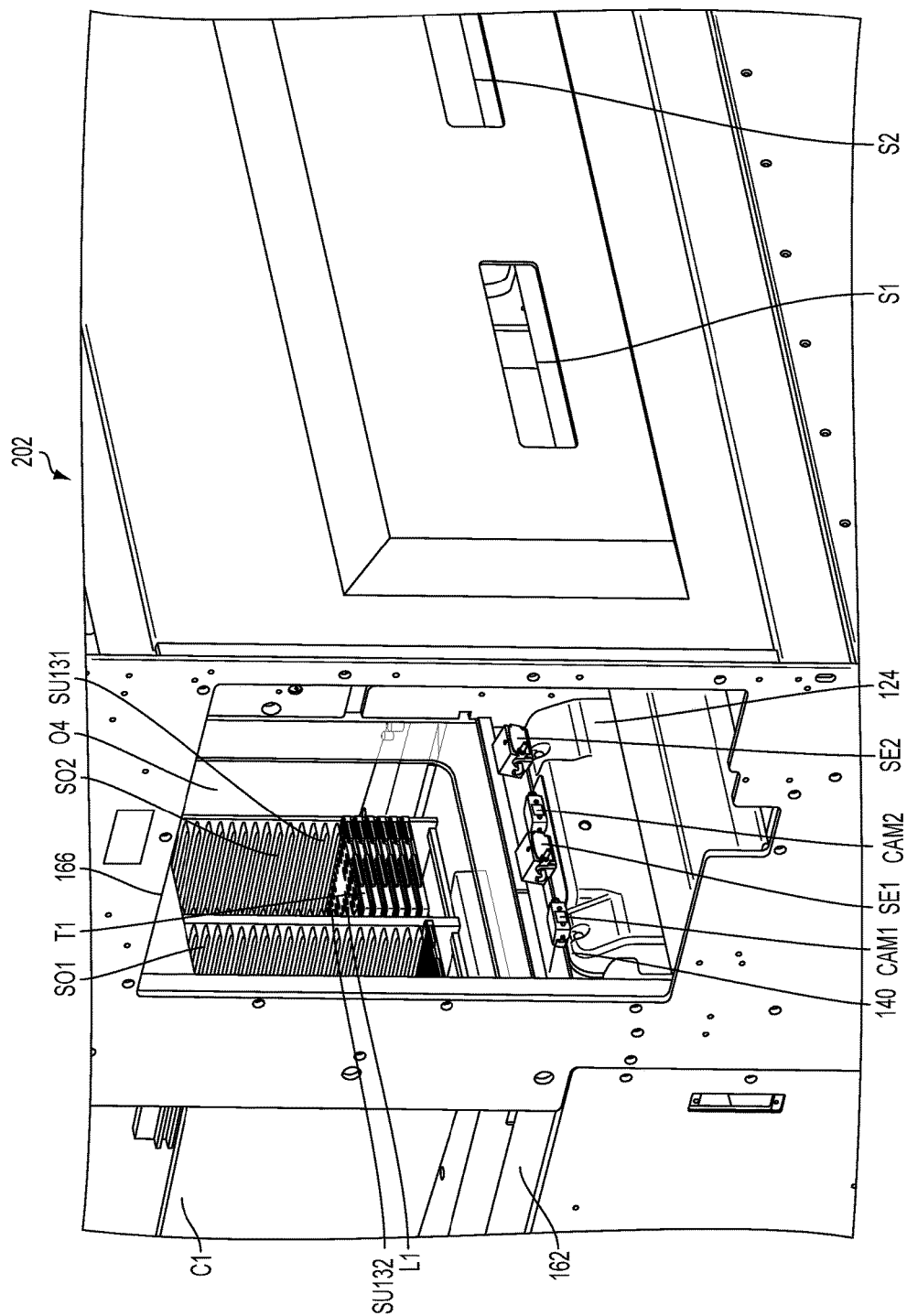

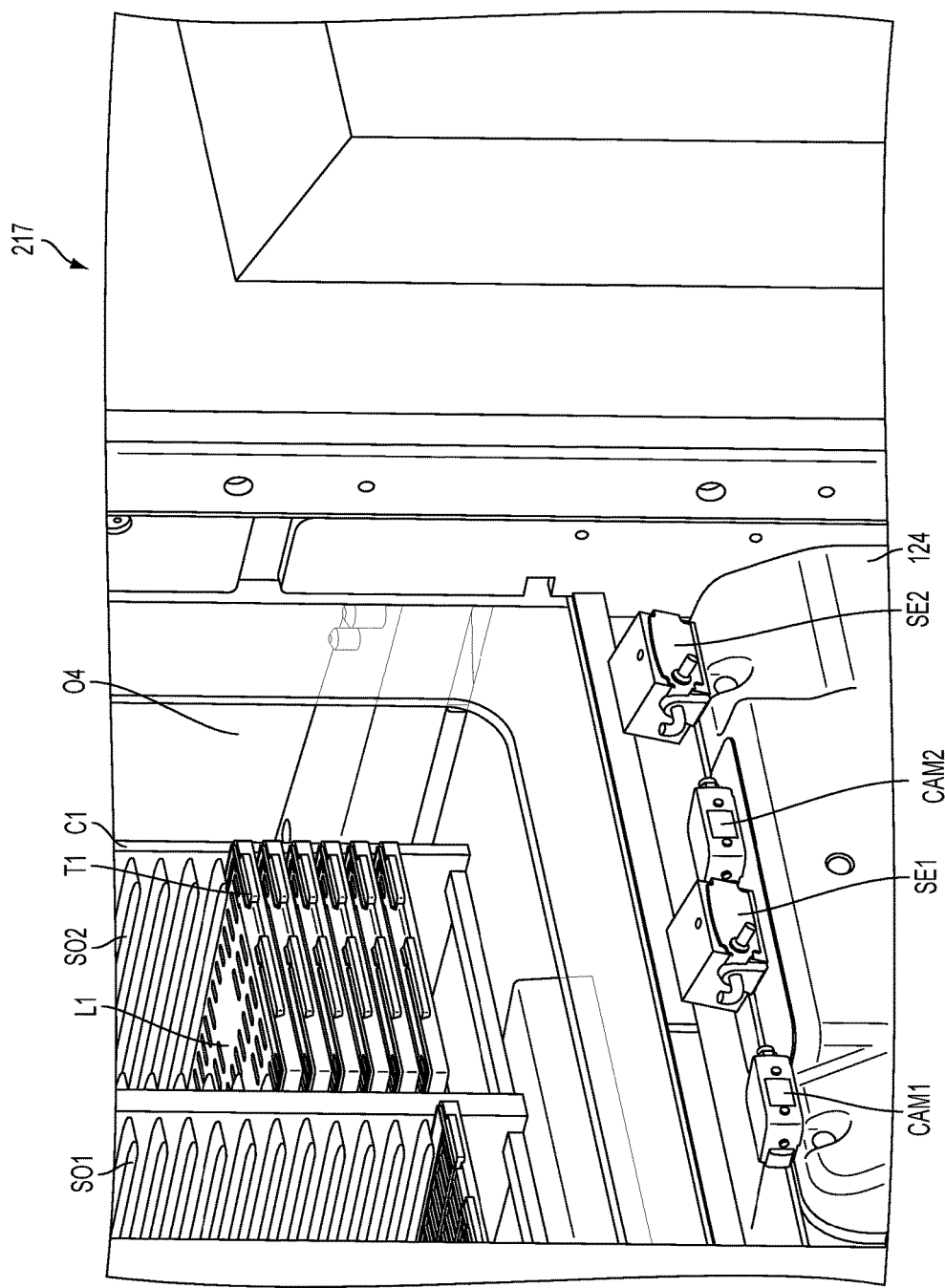

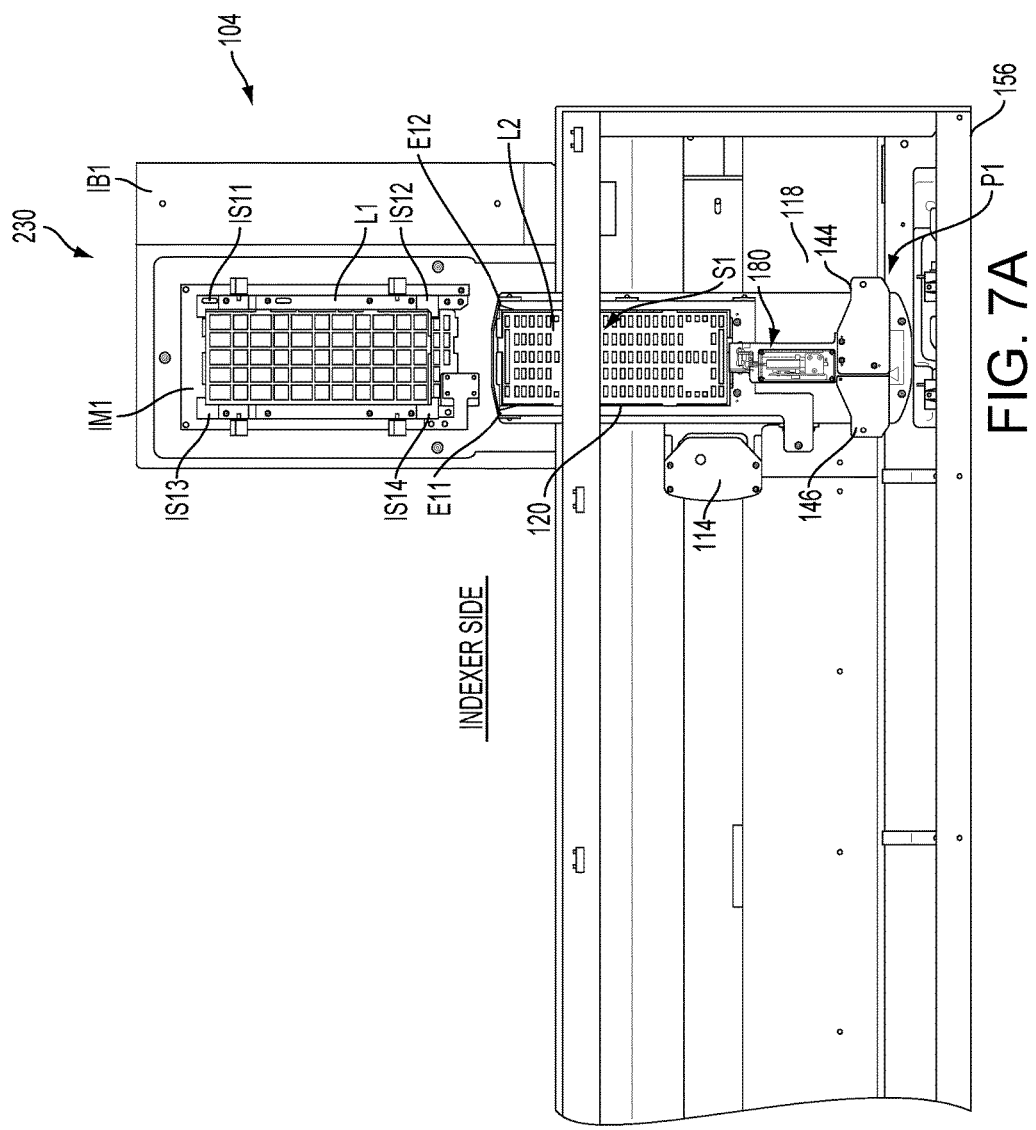

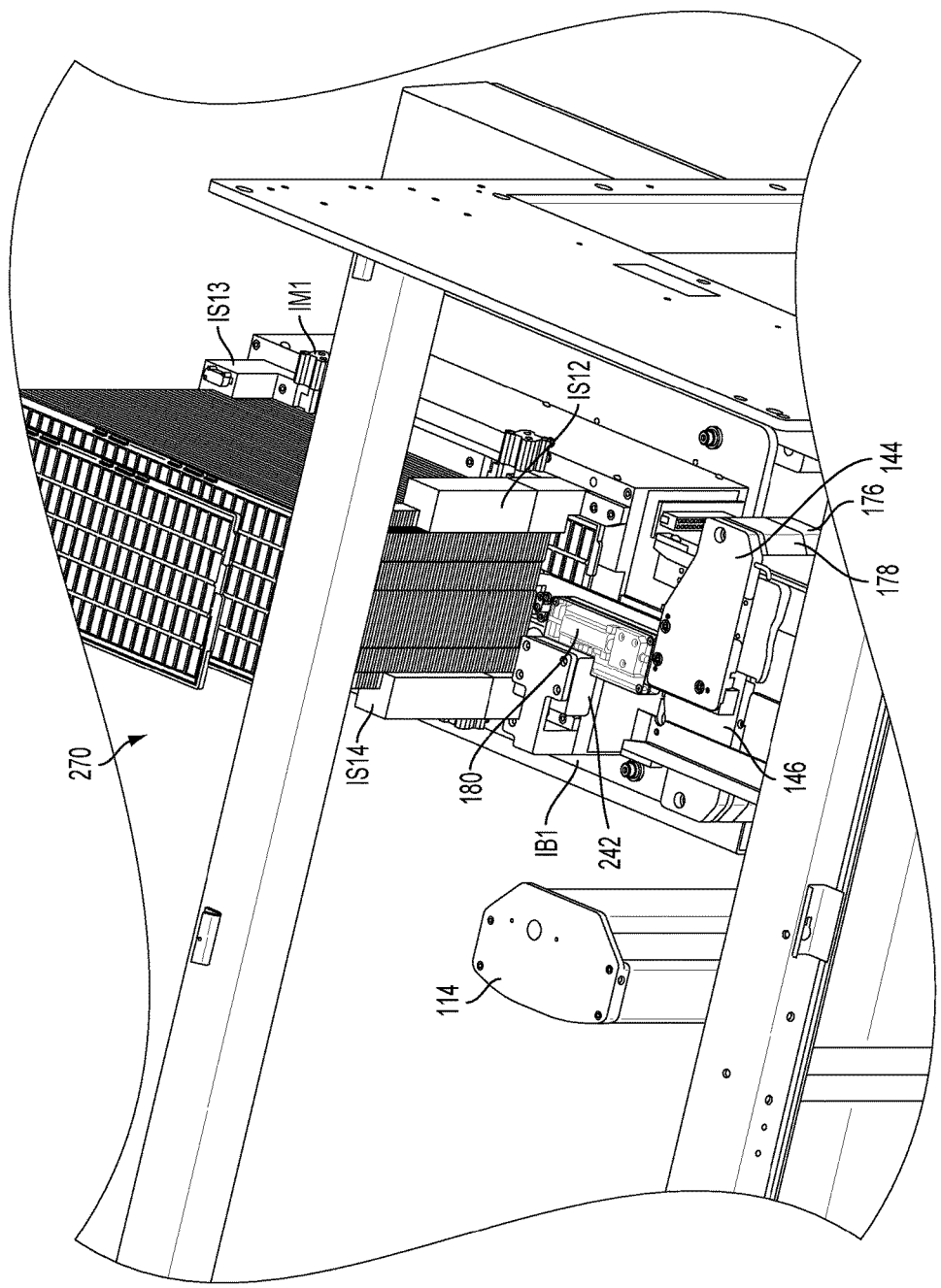

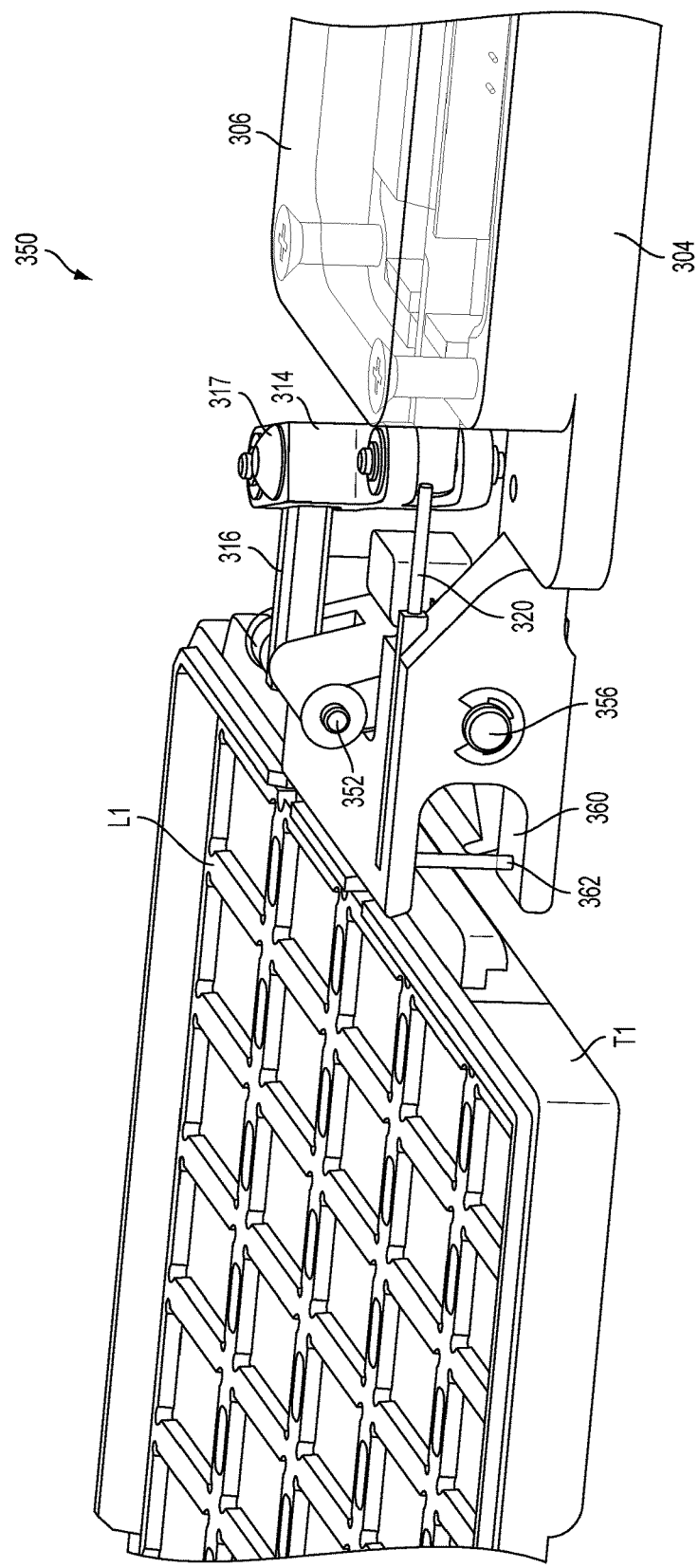

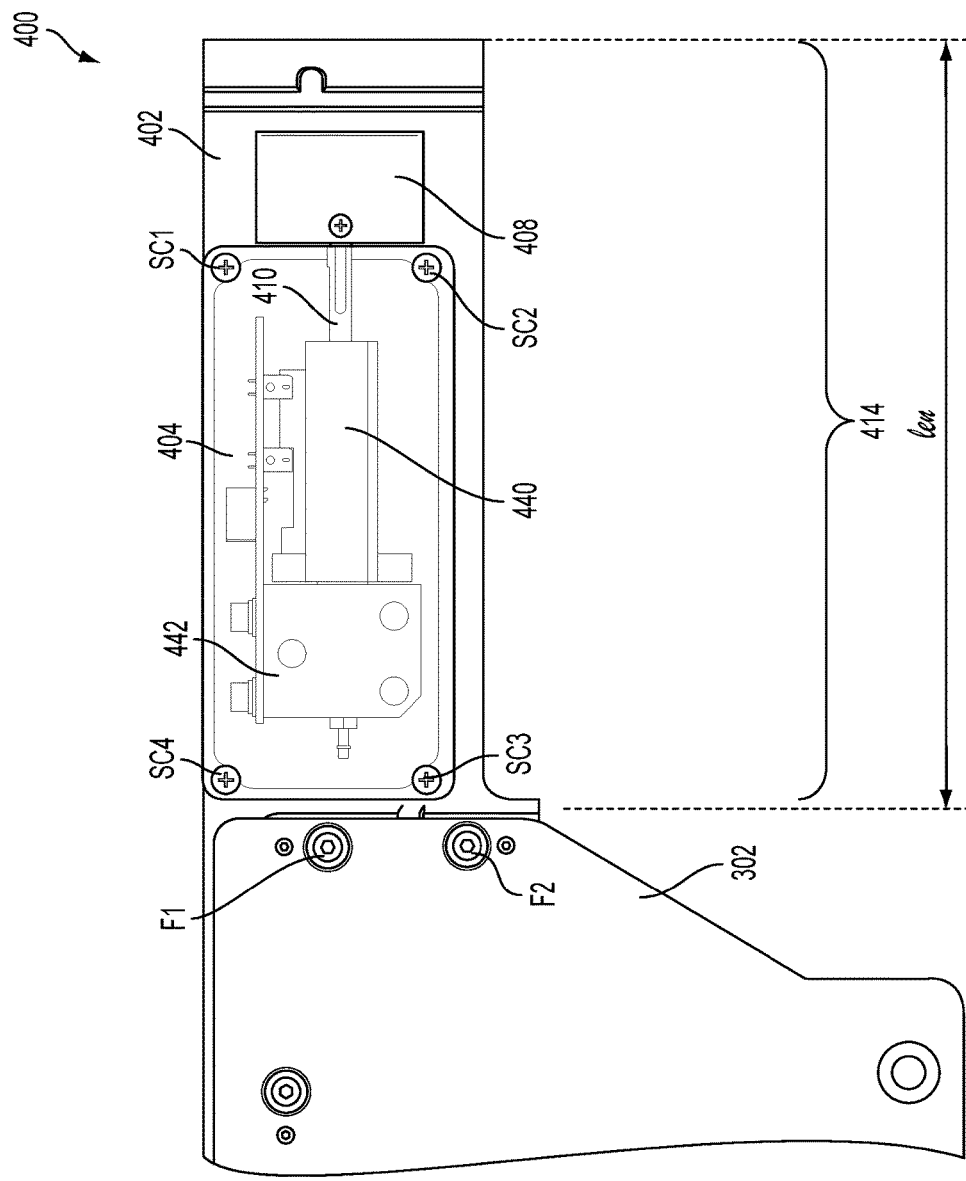

WAFER TRAY SORTER WITH DOOR COUPLED TO DETECTOR

CLAIM OF PRIORITY

This application is a divisional of and claims the benefit of and priority, under 35 U.S.C. § 120, to U.S. patent application Ser. No. 13/830,692, filed on Mar. 14, 2013 and titled "Tray Engine With Slide Attached to an End Effector Base", which is incorporated by reference herein in its entirety.

BACKGROUND

Trays are used to transport a number of devices and materials in fabrication facilities. For example, trays are used to transport a deoxyribonucleic acid (DNA) sample, a semiconductor wafer die, a pharmaceutical drug, etc. The trays may be transported within a building or across buildings.

Sometimes the trays are placed in tray stack supports to protect the trays from falling during transportation. Multiple such tray stack supports are used to transport the trays. Also, the trays are transferred between tray stack supports. For example, a tray stack support may be designated to be sent to an entity A and another tray stack support may be designated to be sent to an entity B. A tray that includes wafer die having specifications provided by the entity A is to be transferred in the tray stack support from a tray stack support to the tray stack support designated to be sent to entity A. Similarly, a tray that includes wafer die for the entity B is to be transferred in the tray stack support designated for the entity B.

However, such transfer of trays between tray stacks to send the trays to tray stacks designated for particular entities may not be available.

SUMMARY

In some embodiments, a sorter is provided to transfer trays between a cassette and an indexer. The sorter includes a tray engine that further includes a vertical drive mechanism. The vertical drive mechanism is rotatable using a motor. Also, the vertical drive mechanism is connected to an end effector. The end effector includes a grip assembly to grip a tray and to transfer the tray between the cassette and the indexer. The vertical drive mechanism is rotated to rotate the end effector to face the cassette or the indexer. For example, when a tray is to be retrieved or delivered to the indexer, the end effector is rotated to face the indexer and when a tray is to be retrieved or delivered to the cassette, the end effector is rotated to face the cassette. The grip assembly is linearly moved in a horizontal direction to grip a tray from the cassette or the indexer or to deliver the tray to the cassette or to the indexer.

In various embodiments, information identifying a tray is read when a tray is transferred between the indexer and the sorter or between the cassette and the sorter. The identification of information and the sorter allows sequencing, characterization, and sorting of trays for transfer of the tray to a cassette designated to be sent to a desired entity.

In various embodiments, a sorter for transferring trays is described. The sorter includes a load port side for loading or unloading a tray from a cassette, an indexer side for loading or unloading a tray from an indexer, and a tray engine for transferring a tray, when present, between the load port side and the indexer side. The indexer side and the load port side are located on opposite sides of the tray engine. The tray engine includes a rotation mechanism, a vertical drive column attached to the rotation mechanism, and an end effector attached to vertical drive column. The end effector includes an end effector base and a slide attached to the end effector base. The end effector further includes a linear drive mechanism coupled to the end effector base and a grip assembly attached to the linear drive mechanism. The linear drive mechanism is used for moving horizontally along the slide to move the grip assembly in a horizontal direction. The grip assembly moves in the horizontal direction to load or unload one or more trays, when present, at the load port side or at the indexer side.

In some embodiments, a tray engine is described. The tray engine may be part of the sorter, a tool, or an equipment front end module (EFEM). The tray engine includes a vertical drive column, a rotation mechanism for rotating the vertical drive column, and an end effector attached to the vertical drive column. The end effector includes an end effector base attached to the vertical drive column. The end effector further includes a slide attached to the end effector base to support a tray, when present. The slide enables the tray to slide along a length of the end effector base. The tray engine includes a drive mechanism attached to the end effector base for moving along the length of the end effector base to enable the tray, when present, to slide linearly along the length and load or unload the tray to or from the slide.

An end effector for transferring trays is described. The end effector may be a part of the tray engine. The end effector includes an end effector base, a slide base located within the end effector base, a linear drive mechanism slidable with respect to the end effector base via the slide base, and a slide attached to the end effector base to support a tray, when present. The linear drive mechanism is configured to move the tray on the slide.

Other aspects will become apparent from the following detailed description, taken in conjunction with the accompanying drawings.

BRIEF DESCRIPTION OF THE DRAWINGS

FIG. 5A is an isometric view of a tray engine of the sorter, in accordance with some embodiments described in the present disclosure.

FIG. 6A is an isometric view of a portion of the EFEM to illustrate use of cameras and sensors to obtain information regarding a tray, in accordance with various embodiments described in the present disclosure.

FIG. 6C is an isometric view of a portion of the EFEM to illustrate a use the cameras and sensors, in accordance with various embodiments described in the present disclosure.

FIG. 7A is a view of an indexer side of the EFEM to illustrate a transfer of trays between the EFEM and the indexer, in accordance with several embodiments described in the present disclosure.

FIG. 7F is a view of the indexer side of the EFEM to illustrate a transfer of trays between the EFEM and the indexer, in accordance with various embodiments described in the present disclosure.

FIG. 8D-2 is another side view of an embodiment of the portion of the grip assembly of FIG. 8A when the twist connector is at the position POS1, in accordance with some embodiments described in the present disclosure.

FIG. 8D-3 is a side view of an embodiment of the portion of the grip assembly of FIG. 8A when the twist connector is at a position POS2 and has gripped a tray, in accordance with several embodiments described in the present disclosure.

FIG. 8D-4 is a side view of an embodiment of the portion of the grip assembly of FIG. 8A when the twist connector is at a position POS3 and has missed gripping a tray, in accordance with some embodiments described in the present disclosure.

FIG. 8H is a view of the grip assembly of FIG. 8A, in accordance with various embodiments described in the present disclosure.

FIG. 10E is a view of the grip assembly of FIG. 10A, in accordance with various embodiments described in the present disclosure.

DETAILED DESCRIPTION

In the following description, numerous specific details are set forth in order to provide a thorough understanding of various embodiments described in the present disclosure. It will be apparent, however, to one skilled in the art that various embodiments described in the present disclosure may be practiced without some or all of these specific details. In other instances, well known process operations have not been described in detail in order not to unnecessarily obscure several embodiments described in the present disclosure.

Although various embodiments are described below as transferring trays between a cassette and an indexer, in several embodiments, trays may be unloaded from or loaded to a tool, may be unloaded from or loaded to a shelf, may be unloaded from or loaded to a box, may be unloaded from or loaded to a container, may be unloaded from or loaded to a robot, may be unloaded from or loaded to a conveyer belt, may be unloaded from or loaded to an overhead transport vehicle, or a combination thereof, etc.

Figure 8A:
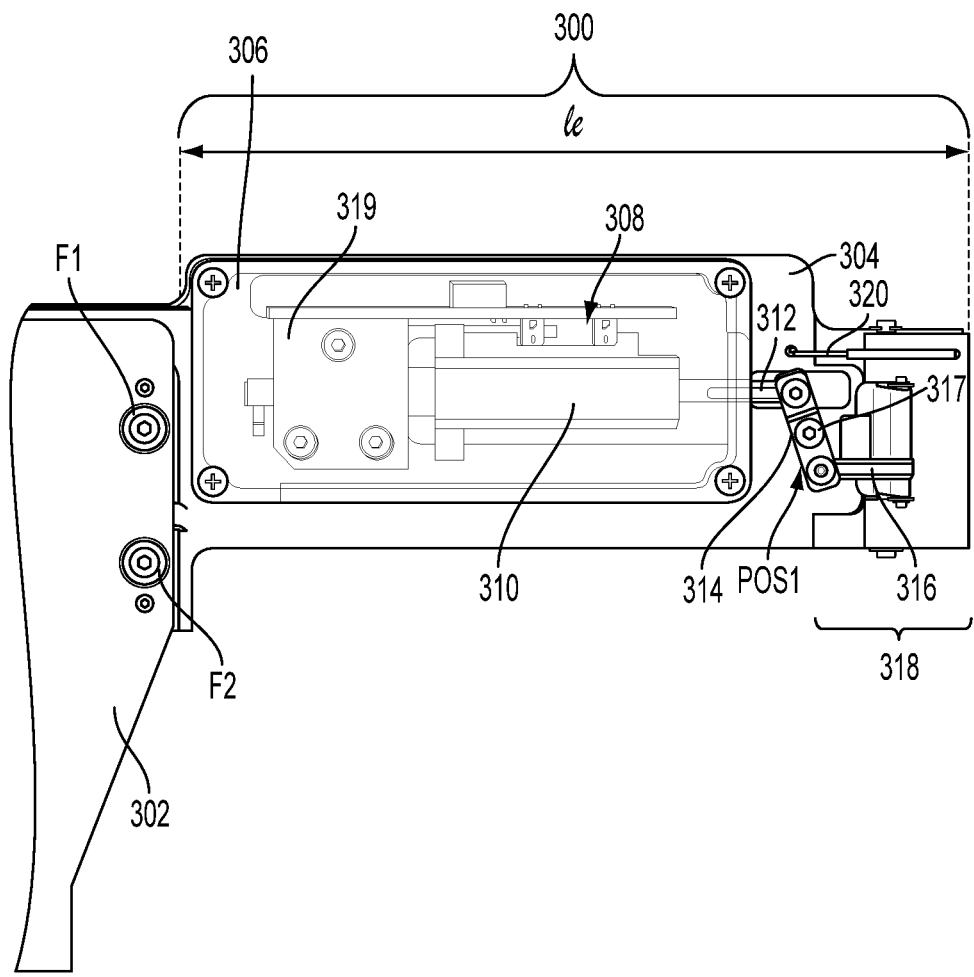
FIG. 8A is a view of a grip assembly that is a portion of an end effector located within the sorter, in accordance with various embodiments described in the present disclosure.
Figure 8B:
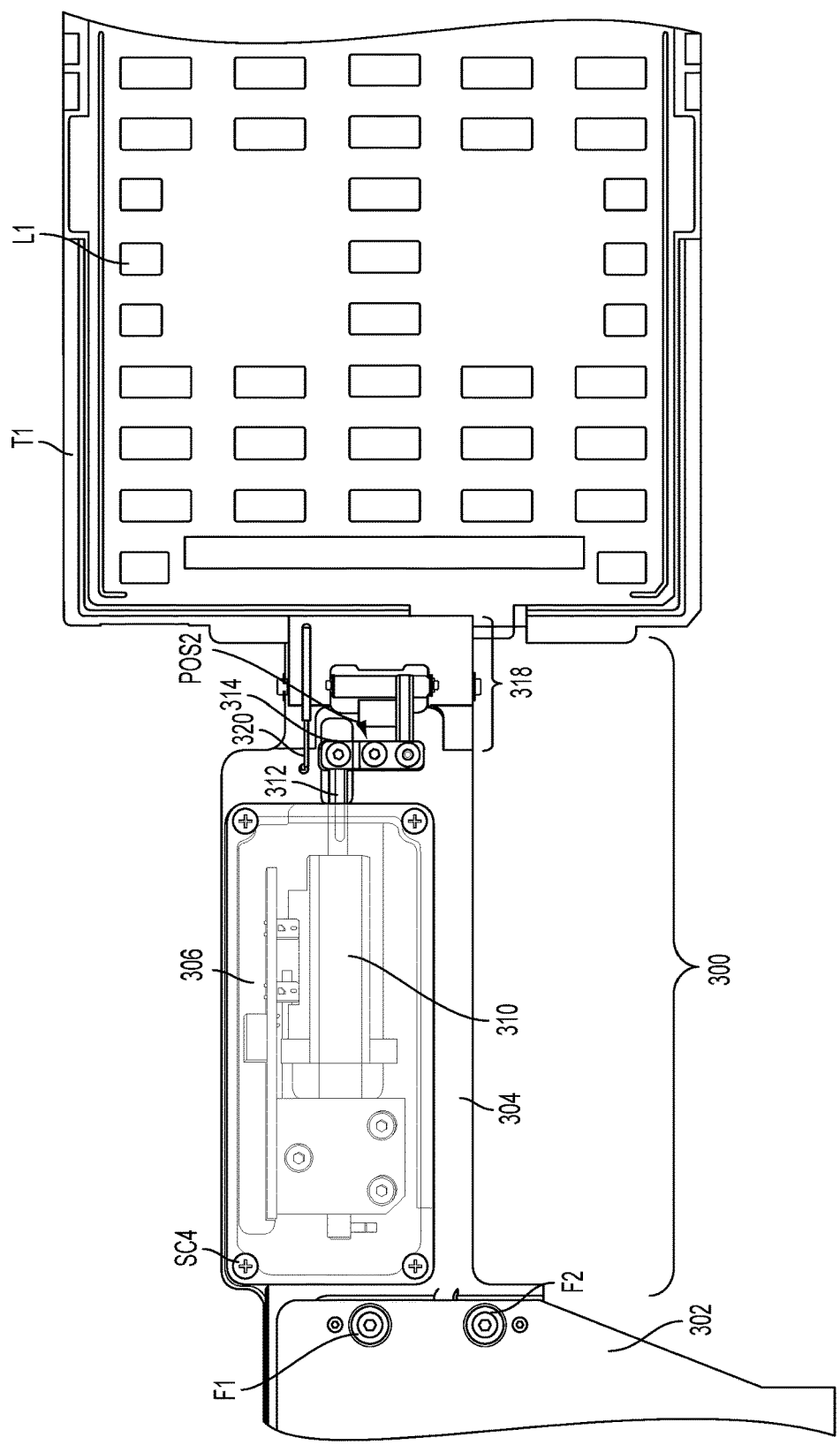
FIG. 8B is a view of the grip assembly of FIG. 8A, in accordance with some embodiments described in the present disclosure.
Figure 8C:
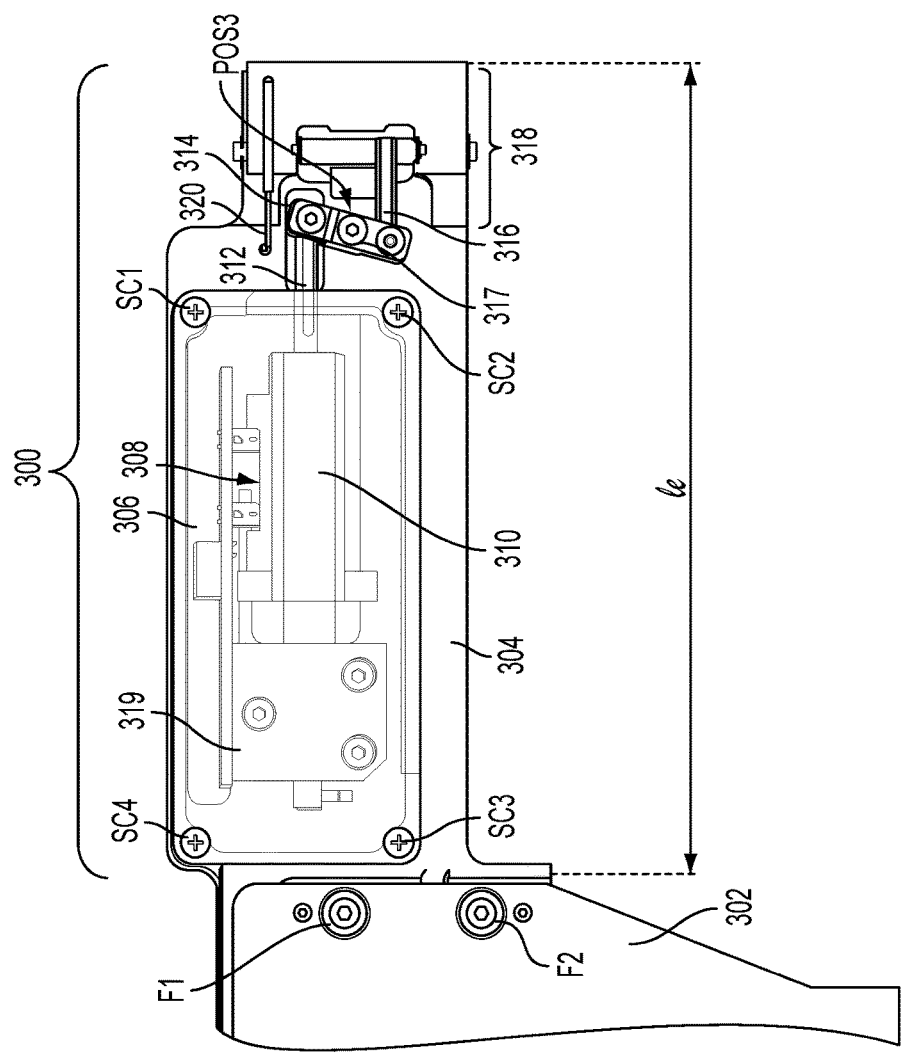
FIG. 8C is a view of the grip assembly of FIG. 8A, in accordance with several embodiments described in the present disclosure.
Figures 1, 8D:
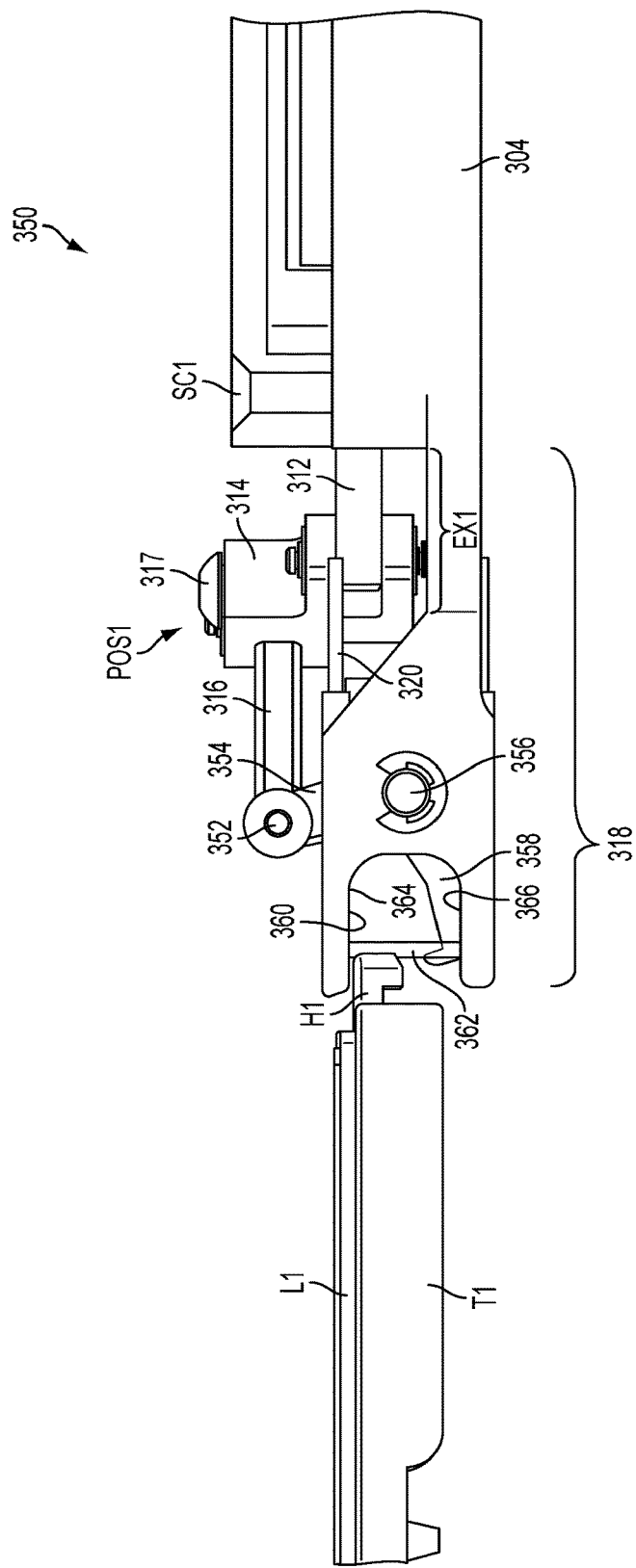
FIG. 8D-1 is a side view of an embodiment of a portion of the grip assembly of FIG. 8A when a twist connector is at a position POS1 to grip a tray or after a recent release of the tray, in accordance with various embodiments described in the present disclosure.
Figures 2, 8D:
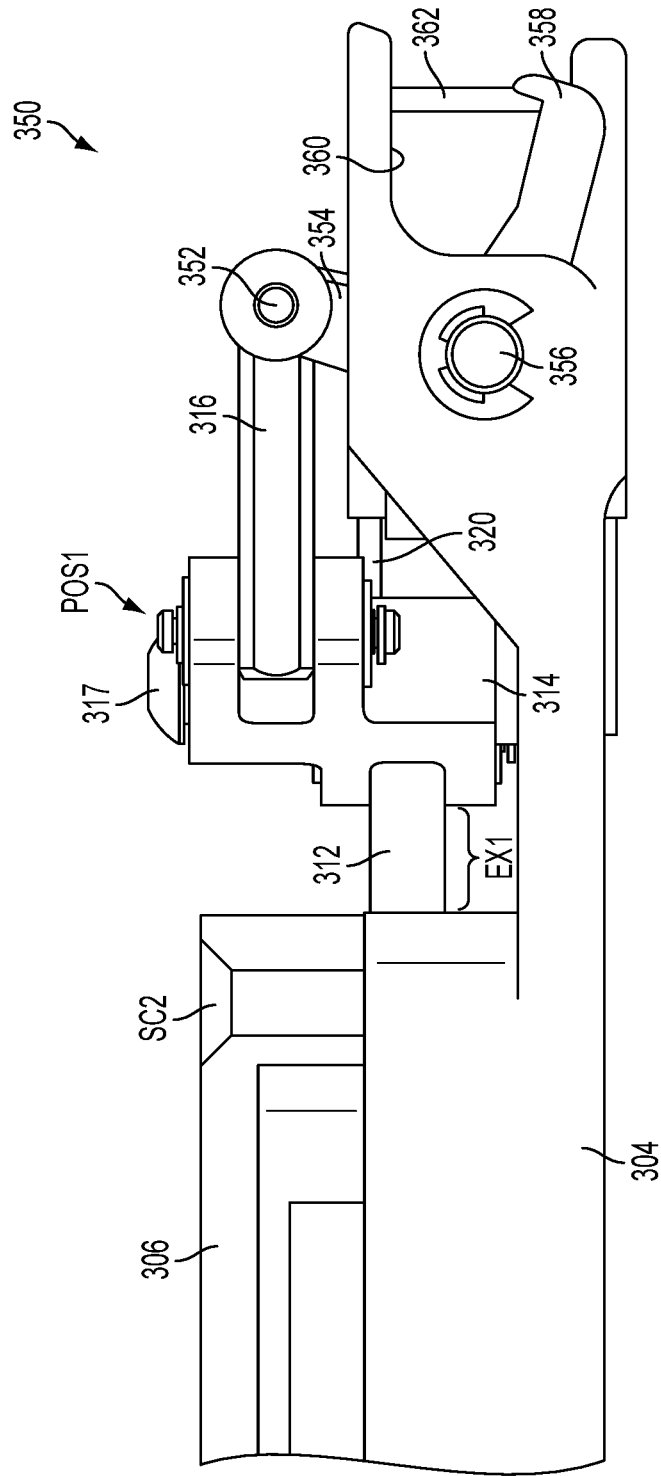
Figures 3, 8D:
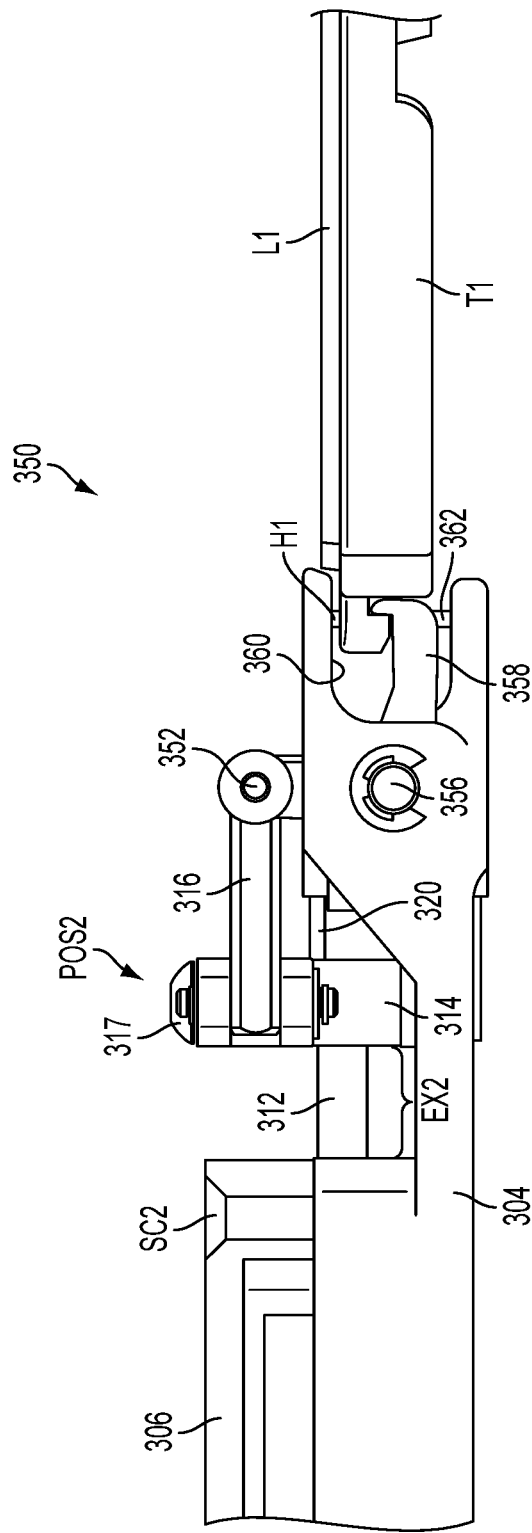

FIG. 1 is a diagram of an embodiment of a system 100 for transferring a tray between a cassette 102 and an indexer 104. The cassette 102 holds one or more trays, e.g., a tray T, a tray T5, etc., between supports. For example, the tray T2 is supported between supports CS21 and CS22 of the cassette 102.

In some embodiments, a tray, e.g., a carrier, etc., stores, within compartments, or within one single compartment within the tray, semiconductor wafer die. In various embodiments, a tray stores, within compartments, light emitting diodes (LEDs), pharmaceutical drugs, biological specimens, deoxyribonucleic acid (DNA) samples, microelectromechanical systems (MEMS), etc. In several embodiments, a tray does not includes compartments to store wafer die, LEDs, pharmaceutical drugs, biological specimens, DNA samples, MEMS, etc. but a gel is used on a tray to hold the wafer die, LEDs, pharmaceutical drugs, biological specimens, DNA samples, MEMS, etc.

In various embodiments, the cassette 102 includes one or more slots. For example, the cassette 102 includes two slots and each slot includes rows of supports that support trays. As another example, the cassette 102 includes three or more slots. A slot of the cassette 102 is separated from another slot of the cassette 102 by a wall within the cassette 102.

In some embodiments, each support of the cassette 102 extends along a side of the cassette 102. For example, the support CS21 is substantially parallel to and adjacent to a side of the cassette 102 and the support CS22 is substantially parallel to and adjacent to an opposite side of the cassette 102. The opposite side faces the side that is adjacent to the support CS21.

In some embodiments, two devices are substantially parallel to each other when an angle between the two devices ranges between −1 degrees and +1 degrees. In various embodiments, two devices are substantially parallel to each other when an angle between the two devices ranges between −2 degrees and +2 degrees.

In various embodiments, supports that support a tray are located parallel to each other. For example, the support CS21 is parallel to the support CS22.

In several embodiments, the supports of the cassette 102 that are substantially parallel to each other form a level within the cassette 102. For example, the supports CS21 and CS22 form a level.

In several embodiments, the cassette 102 lacks one or more covers, e.g., a front cover, a top cover, etc. A cover provides access to an inside of the cassette 102. One or more trays are supported within an inner region of the cassette 102. In various embodiments, the cassette 102 is not a closed container that is closed on all sides and may be accessed via a door on a front side.

The system 100 includes a sorter 106 that receives one or more trays from the cassette 102 that is placed on a shelf 107 of the sorter 106. The shelf 107 is located at a load port side of the sorter 106. In several embodiments, the sorter 106 simultaneously receives multiple trays from the cassette 102.

The sorter 106 includes a tray engine 108 that is fixed to a base 110 of the sorter 106. In one embodiment, as shown in FIG. 1B, the tray engine 108 is moveable along a track. The tray engine 108 includes a theta (θ) motor 112 that is connected to a vertical drive column 114 via a connecting mechanism, e.g., gears, belts, etc. The theta motor 112 operates to rotate the vertical drive column 114 by the angle θ. For example, the theta motor 112 rotates the vertical drive column 114 by an angle between zero and 360 degrees. The theta motor 112 is an example of a rotation mechanism.

In several embodiments, a motor may be a stepper motor or a continuous motor.

In some embodiments, when the theta motor 112 rotates the vertical drive column 114 to 180 degrees, an end effector, further described below, faces the load port side and when the theta motor 112 rotates the vertical drive column 114 to 0 degrees, the end effector faces the indexer side.

An end effector 116 is located within the sorter 106 and is connected to the vertical drive column 114. For example, the end effector 116 is attached to the vertical drive column 114 via an attachment mechanism, e.g., screws, fasteners, etc. The end effector 116 includes an end effector base 118 that is fixed substantially perpendicularly to the vertical drive column 114. For example, the end effector 118 is attached to the vertical drive column 114 via an attachment mechanism, examples of which are provided above. The end effector 116 further includes an upper slide 120 that supports and slides a tray. The end effector 116 also include a lower slide 122 that supports and slides a tray.

In various embodiments, two devices are substantially perpendicular to each other when an angle between the two devices range between 89 degrees and 91 degrees. In several embodiments, two devices are substantially perpendicular to each other when an angle between the two devices range between 88 degrees and 92 degrees.

In some embodiments, the slides 120 and 122 are made of a low friction material, e.g., metals, alloys of metals, etc.

In various embodiments, instead of the slides 120 and 122, a belt is used as a support surface for trays. The belt is driven by a motor to slide a tray supported on the belt. Moreover, motion of the belt is co-ordinated with motion of a grip assembly, which is further described below. For example, motion of the belt is co-ordinated with engaging and/or locking a tray. The engagement and locking are performed by the grip assembly and are further explained below.

In the embodiments in which the belt is used as the support surface, a gripper is used to grip a tray from the cassette 102 or the indexer 104 to the belt. In several embodiments, a top surface of the belt is attached to the gripper.

Both the slides 120 and 122 are located substantially parallel to the end effector base 118. For example, the slides 120 and 122 form an angle between −1 degrees and degree with respect to the end effector base 118. Example of each slide 120 and 122 includes a rail, a track, etc.

In some embodiments, the upper slide 120 is located vertically above the lower slide 122.

The slides 120 and 122 are attached to the end effector base 118 via an attachment mechanism.

The end effector 116 moves vertically up and down with vertical movement of the vertical drive column 114. For example, a vertical drive motor (not shown) is connected to the vertical drive column 114 via a connecting mechanism to drive the end effector 116 and the vertical drive column 114 up and down via the connecting mechanism.

In some embodiments, both the slides 120 and 122 simultaneously slide two trays along the end effector base 118.

In various embodiments, the end effector 116 includes any other number of slides to simultaneously slides any other number of trays. For example, the end effector 116 includes three or more slides to slide three or more trays.

The sorter 106 includes a door 124 that allows access to the sorter 106. The door 124 slides down along a side wall W1 of the sorter 106. The door 124 is driven by a door motor (not shown) that is located within the base 110 and a connecting mechanism that connects the door 124 to the door motor.

In some embodiments, the load port side includes the side wall W1 and the shelf 107.

In various embodiments, the sorter 106 includes any number of doors. For example, the sorter 106 includes two to six doors that are located along the side wall W1.

In some embodiments, instead of sliding down along the side wall W1, the door 124 slides up along the side wall W1. In the embodiments in which the door 124 slides up along the side wall W1 instead of down, one or more cameras are fixed to bottom of the door 124.

A camera CAM1, e.g., a digital camera, an image capture device, a Z-depth camera, etc., is located on top of the door 124. The camera CAM1 is fixed to the door 124 via an attachment mechanism, e.g., screws, fasteners, etc.

In various embodiments, any number of cameras are fixed on top of the door 124. For example, two or three cameras are attached to the top of the door 124.

In some embodiments, instead of a camera that captures images, a scanner, e.g., a barcode scanner, etc., that scans information, e.g., a code, a barcode, etc., located on a tray is used. Examples of a barcode scanner include a laser scanner, a charge-coupled device (CCD) reader, an omni-directional barcode scanner, a camera-based reader, etc.

In several embodiments, instead of a camera, an ultrasonic transducer may be used to capture ultrasonic images of information identifying a tray or a tray lid.

In various embodiments, a wave generating and capturing device may be a used instead of a camera for generating waves and capturing images of information identifying a tray or a tray lid.

In various embodiments, instead of a camera that captures an image, a radio frequency (RF) receiver is used to receive RF signals from an RFID tag that is on a tray to identify the tray. The information within the RF signals is transferred from the RF receiver to a computer system, which is further described below for analysis of the information.

In several embodiments, in addition to one or more cameras, one or more sensors are used to sense presence or absence of a tray in the cassette 102. The one or more sensors are fixed on top of the door 124. Examples of sensors include infrared sensors, optical sensors, air sensors, pneumatic sensors, beam-breaking sensors, retro-reflective optical sensors, ultrasonic sensors, etc.

In some embodiments, in addition to the sensors and the cameras, height measuring devices, e.g., encoders, decoders, etc., are attached to top or bottom surfaces of the door and are used to measure location, e.g., levels, etc., along a vertical axis of each tray within the cassette 102 or the indexer 104.

In various embodiments, the sensors, the cameras, and/or the height measuring devices are attached to top or bottom surfaces of the slides 120 and/or 122 instead of being attached to the door 124. In some embodiments, the sensors, the cameras, and/or the height measuring devices are attached to grip assemblies, which are further described below, instead of being attached to the door 124.

In several embodiments, the height measuring devices are used with the sensors to determine locations of absence of trays within the cassette 102 or the indexer 104.

In several embodiments, the locations measured of each tray or of levels that do not include trays is used to adjust a height of the vertical drive column 114. For example, the computer system receives the locations measured of each tray or of levels that do not include trays from the encoder and decoder and sends a signal to the vertical drive motor to adjust a height of the slides 120 and 122 to receive trays from levels that include trays or to deliver trays to levels that do not include trays.

In various embodiments in which the door 124 slides up along the side wall W1 instead of down, instead of being fixed on top of the door 124, the one or more sensors and/or the height measuring devices are fixed to bottom of the door 124.

The sorter 106 has a side wall W2 that is located opposite to the side wall W1. For example, the side walls W1 and W2 are located on opposite sides of the sorter 106. The side wall W2 includes a slot S1 for allowing passage of a tray.

In several embodiments, the side wall W2 includes any number of slots, e.g., two, three, fourth, five, etc. Each slot allows passage of a number, e.g., one, two, three, etc., of trays.

The indexer 104 holds a number of trays, e.g. a tray T1, a tray T3, and a tray T4, etc., between indexer columns. The trays stack on top of each other between the columns of the indexer 104.

The indexer columns that stack trays within the indexer 104 are located substantially parallel to each other.

In several embodiments, instead of indexer columns, the indexer 104 include substantially parallel supports similar to that of the supports CS11 and CS12 to support trays within the indexer 104.

The indexer 104 includes an indexer module 128 that is located on an indexer base 130. The indexer module 128 has a bottom surface 109 that is driven by an indexer motor via a connecting mechanism to move the bottom surface 109 vertically up and down. Any trays supported on the bottom surface 109 of the indexer module 128 move up and down with the bottom surface 109.

The indexer base 130 is placed on a shelf 132 of the sorter 106. The shelf 132 is located on an indexer side, which is a side located on an opposite side of the load port side.

In various embodiments, the indexer side includes the side wall W2 and the shelf 132.

The cassette 102 is placed on top of the shelf 107. For example, the cassette 102 is placed by a user on top of the shelf 107. As another example, the cassette 102 is placed on top of the shelf 107 via an automated mechanism, e.g., automated guided vehicle (AGV), robot arms, etc.

In various embodiments, the cassette 102 is moved close to the door 124. For example, the cassette 102 is moved to be within a pre-determined distance from the door 124.

The door motor is operated to open the door 124. As the door 124 moves down, the one or more sensors attached to the door 124 sense whether a tray is present between supports CS11 and CS12, then sense whether a tray is present between the supports CS21 and CS22, and so on until the one or more sensors sense all levels of supports in the cassette 102. For example, the one or more sensors determine that there is an absence of a tray between the supports CS11 and CS12 and that there is a presence of the tray T2 between the supports CS21 and CS22. It should be noted that the supports CS11 and CS12 are located at a level above the supports CS21 and CS22.

The sensors send data identifying levels of the cassette 102 at which presence of trays is sensed to the computer system. The computer system controls one or more cameras, e.g., CAM1, CAM2, etc, to capture images of information identifying trays at levels at which a presence of the trays is sensed.

As the door 124 moves down, for the levels within the cassette 102 that include the trays, one or more cameras CAM1, CAM2, etc., attached to the top of the door 124 capture an image of information identifying the trays within the cassette 102. For example, the one or more cameras attached to the top of the door 124 take a picture of a code on the tray T2 and then take a picture of a code of the tray T5. In this example, the one or more cameras do not capture an image of a space between the supports CS11 and CS12 as there is an absence of a tray between the supports CS11 and CS12.

In the embodiments in which the door 124 moves up instead of down, as the door 124 moves up, the one or more sensors at the bottom of the door 124 sense the presence or absence of trays within the cassette 102 and the one or more cameras at the bottom of the door 124 take an image of information on the trays for the levels that support the trays. For example, the one or more sensors sense presence of the tray T5 and then sense presence of the tray T2. As another example, the one or more cameras take a picture of information on the tray T5 and then take a picture of information on the tray T2.

The theta motor 112 operates to rotate the vertical drive column 114 at an angle theta to position the end effector 116 to extend substantially parallel to the supports of the cassette 102 at a level. For example, the theta motor 112 operates to rotate the vertical drive column 114 so that edges of the slides 120 and 122 face the side wall W1. As another example, the theta motor 112 operates to rotate the vertical drive column 114 so that the slides 120 and 122 are substantially perpendicular to the side wall W1.

The vertical drive motor operates to adjust a level of the end effector 116 vertically up or down to facilitate obtaining one or more trays from the cassette 102. For example, a level of the upper slide 120 is adjusted to substantially match a level of the tray supports CS21 and CS22 that support the tray T2 and a level of the lower slide 122 is adjusted to substantially match a level of the supports CS31 and CS32 of the cassette 102. The supports CS31 and CS32 lay at a level below the tray supports CS21 and CS22.

In some embodiments, a distance between the upper slide 120 and the lower slide 122 extends across one or more levels of the cassette 102. For example, a distance between the upper slide 120 and the lower slide 122 spans across three levels of the cassette 102. As another example, a distance between the upper slide 120 and the lower slide 122 is equal to one level of the cassette 102.

Grip assemblies of the end effector 116 extend substantially horizontally with the sliding of driving plates of the end effector 116 along the slides 120 and 122 to come close to and grip one or more edges of one or more trays within the cassette 102. For example, a grip assembly of the end effector 116 is extended horizontally when an upper driving plate of the end effector 116 slides along the upper slide 120 to facilitate gripping an edge E2 of the tray T2. The grip assemblies and the driving plates are further described below.

The driving plates and grip assemblies retract to slide a tray from supports at a level within the cassette 102 to a slide of the end effector 116. For example, an upper grip assembly retracts with retraction of the upper driving plate at a level of the upper slide 120 to slide the tray T2 from the supports CS21 and CS22 to bring the tray T2 between arms of the upper slide 120. Moreover, when another tray is present between the supports CS31 and CS32, a lower driving plate at a level of the lower slide 122 retracts to slide the tray from the supports CS31 and CS32 to bring the tray between arms of the lower slide 122.

In some embodiments, the trays may be extracted from the cassette 102 or from the indexer 104 to process, e.g., test, assemble, clean, etc., wafer die within the trays.

In several embodiments, both the upper and lower driving plates simultaneously retract to retrieve trays from the levels of the supports CS21 and CS22 and supports CS31 and CS32 to bring the trays between arms of the upper slide 120 and the lower slide 122.

The theta motor 112 rotates by the angle theta to rotate the end effector 116 towards the side wall W2 from the side wall W1. When the end effector 116 is rotated to face the side wall W2, edges of the end effector 116 face the side wall W2. The vertical drive motor moves the end effector 116 and the vertical drive column 114 up or down to position the slides 120 and 122 between levels of upper and lower edges of the slot S1.

The indexer 104 is placed close to the slot S1 to facilitate placement of a tray via the slot S1 into the indexer 104. The indexer motor also moves the indexer 104 up or down to level trays within the indexer 104 to position the indexer 104 to facilitate reception of one or more trays from the end effector 116. For example, a level of a tray within the indexer 104 is controlled with the indexer motor to place another tray on top of the tray level or to remove the tray at the level from the indexer 104.

The grip assembly of the end effector 116 extends through the slot S1 into the indexer 104 to slide the tray T2 that is received from the cassette 102 at a level within the indexer 104. The tray T2 slides onto another tray within the indexer 104 or on top of a bottom surface 109 of the indexer 104.

In various embodiments, the grip assemblies of the slides 120 and 122 extend through the slot S1 into the indexer 104 to simultaneously slide two trays at two levels within the indexer 104 on top of a tray within the indexer 104 or on top of the bottom surface 109 of the indexer 104.

In some embodiments, instead of delivering a tray from the cassette 102 via the sorter 106 to the indexer 104, a tray is delivered from the indexer 104 and sent to the cassette 102 via the sorter 106. For example, with the extension of the upper driving plate, the grip assembly of the end effector 116 extends via the slot S1 into the indexer 104 and grips a tray located within the indexer 104. With the retraction of the upper driving plate, the grip assembly then retracts to slide the tray that may be located on top of another tray within the indexer 104 or on top of the bottom surface 109 of the indexer 104 from the indexer 104 to the arms of the upper slide 120. The theta motor rotates to allow the edges of the end effector 116 to face an opening in the side wall W1 formed by opening the door 124. The opening in the side wall W1 is created when the door 124 moves up or down. Also, the end effector motor moves the end effector 116 vertically up or down to position the end effector 116 to facilitate delivery of the tray to the cassette 102. The grip assembly of the end effector 116 extends via the opening in the side wall W1 to deliver a tray from the arms of the upper slide 120 to supports at a level within the cassette 102.

In various embodiments, the cassette 102 lacks supports to support trays. In these embodiments, the cassette 102 includes a base that supports a bottom tray within the cassette 102 and any other trays are supported on the bottom tray and the base.

Figure 1A:
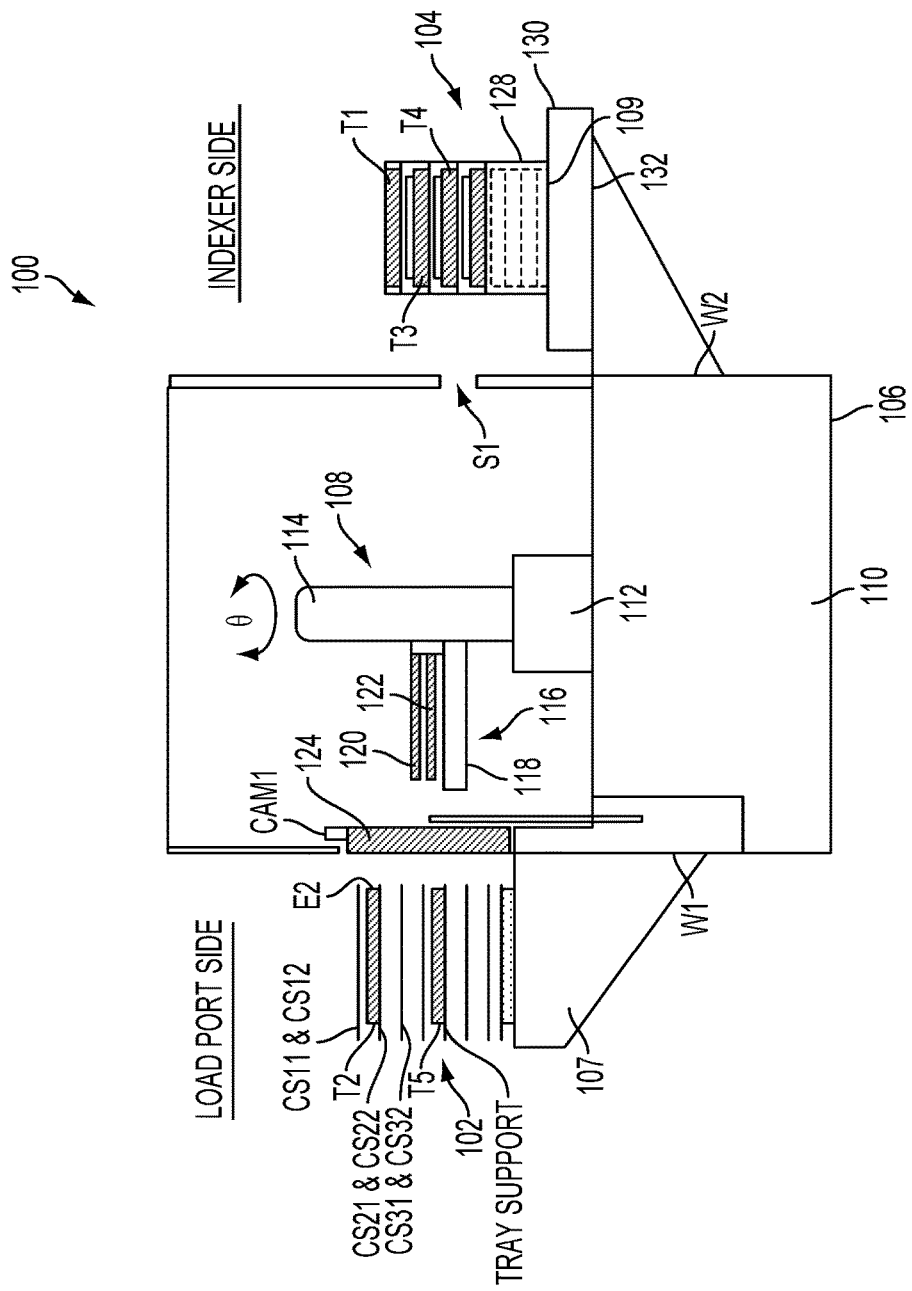
FIG. 1A is a diagram of a sorter for transferring a tray between a cassette and an indexer, in accordance with various embodiments described in the present disclosure.
Figure 1B:
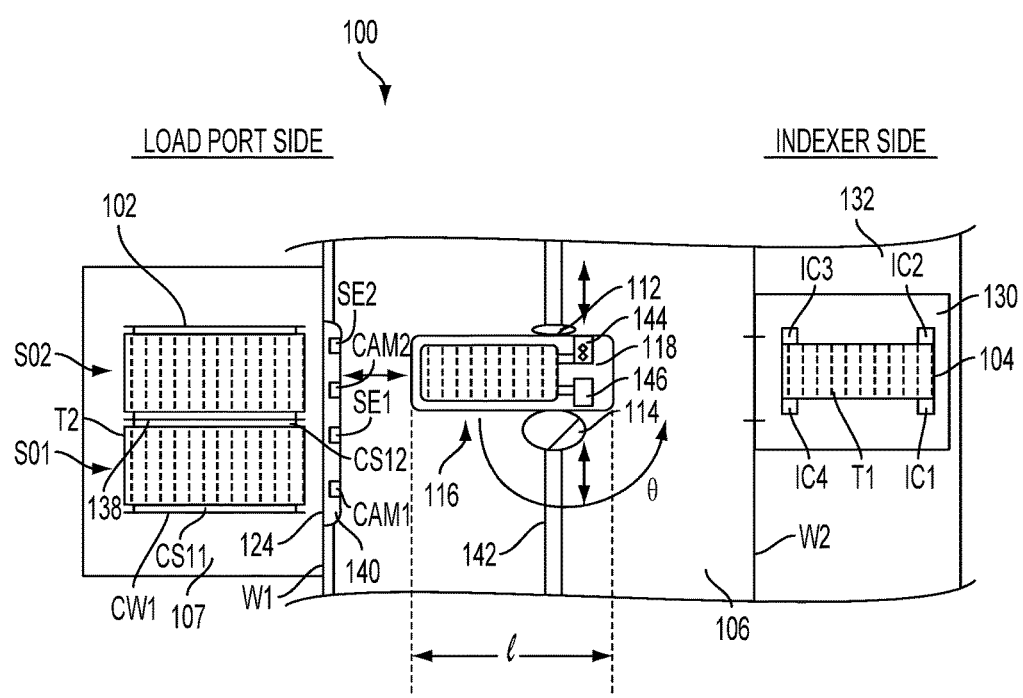
FIG. 1B is a top view of the sorter, in accordance with some embodiments described in the present disclosure.

FIG. 1B is a top view of the system 100 of FIG. 1A. In the FIG. 1B, two slots SO1 and SO2 are visible. The slots SO1 and SO2 are located adjacent to each other and are separate from each other by a common wall 138. As shown, the support CS11 extends along a cassette wall CW1 and the support CS12 extends along the common wall 138.

Also, as shown, the cassette 102 lacks a front door that provides access to the sorter 106 of the trays within the cassette 102.

The sensors SE1 and SE2 are attached to a top surface 140 of the door 124. The cameras CAM1 and CAM2 are also attached to the top surface 140. The sensor SE1 senses whether a tray is located within the slot SO1 and the sensor SE2 senses whether a tray is located within the slot SO2.

Similarly, when the sensor SE1 determines that a tray is present at a level within the slot SO1, the camera CAM1 captures an image of information on the tray. On the other hand, when the sensors SE1 determines that a tray is absent at a level within the slot SO1, the camera CAM1 does not capture an image at the level. Moreover, when the sensor SE2 determines that a tray is present at a level within the slot SO2, the camera CAM2 captures an image of information on the tray. On the other hand, when the sensor SE2 determines that a tray is absent at a level within the slot SO2, the camera CAM2 does not capture an image at the level.

The vertical drive column 114 moves along a rail 142 to move the end effector 116 (FIG. 1) along the rail 142 in a direction that is substantially parallel to the side walls W1 and W2. The vertical drive column 114 is driven along the rail 142 by a column motor (not shown). The column motor drives the vertical drive column 114 along the rail 142 via a connecting mechanism. The movement of vertical drive column 114 along the rail 142 allows the end effector 116 to retrieve trays via openings created by opening multiple doors at the side wall W1 of the sorter 116 and also deliver trays via multiple slots in the side wall W2 of the sorter 116.

The end effector 116 includes a top driving plate 144 and a bottom driving plate 146. The top driving plate 144 slides along the upper slide 120 (FIG. 1) to slide a tray supported between the arms of the upper slide 120. In some embodiments, a tray and the driving plates 144 and 146 slide along a length "l" of the end effector base 118 to slide in a linear direction.

Moreover, the end effector 116 includes a bottom driving plate 146 that is located below the top driving plate 144. The bottom driving plate 146 slides along the bottom slide 122 (FIG. 1) to slide a tray supported between the arms of the lower slide 122.

The indexer 104 includes multiple indexer columns IC1 thru IC4, e.g., bars, rods, etc., that extend vertically to stack trays within the indexer 104.

Figure 1C:
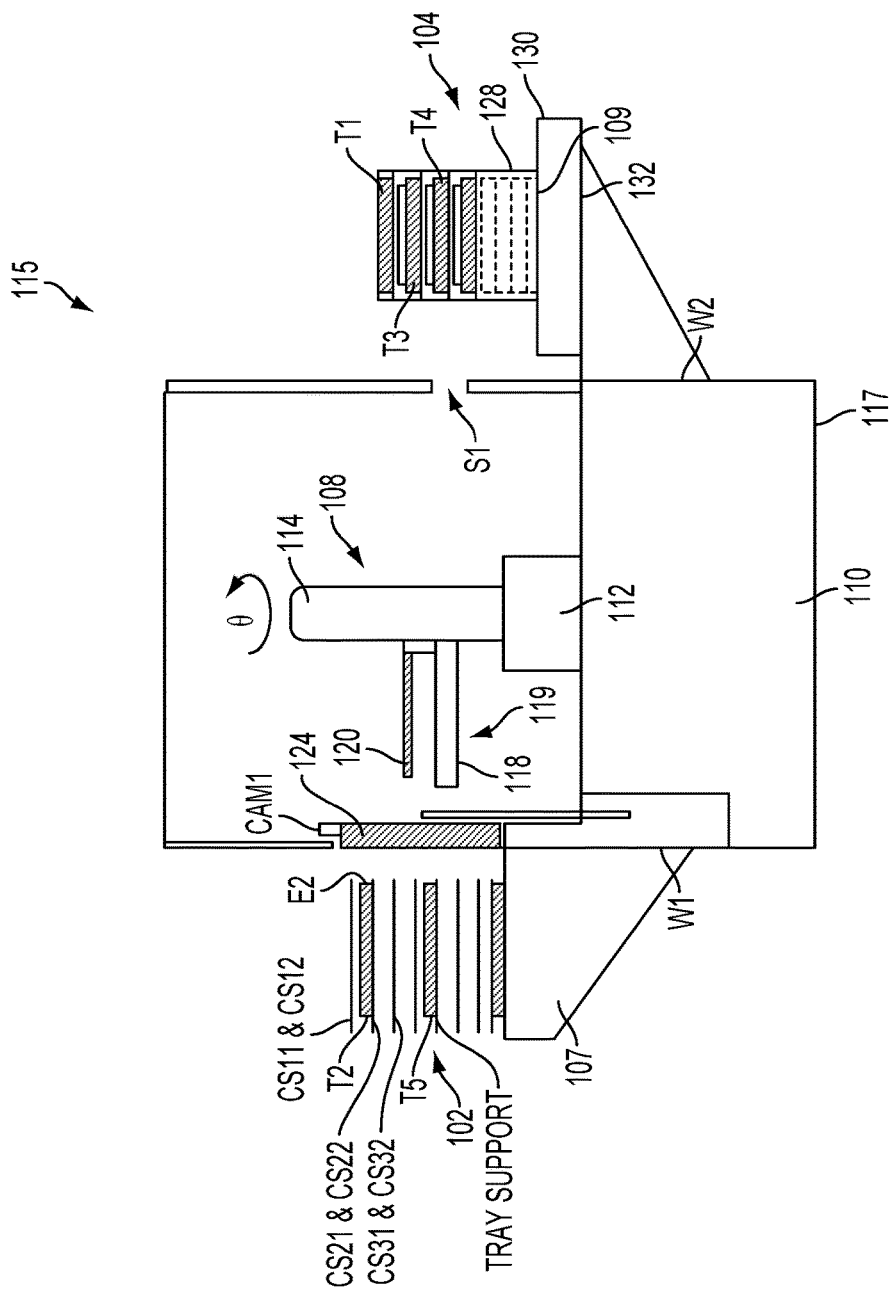
FIG. 1C is a diagram of a sorter having one slide for transferring a tray between a cassette and an indexer, in accordance with several embodiments described in the present disclosure.

FIG. 1C is a diagram of an embodiment of a system 115 for transferring a tray between the cassette 102 and the indexer 104. The system 115 includes a sorter 117, which is similar to the sorter 106 (FIG. 1A) except that the sorter 117 includes an end effector 119 instead of the end effector 116 (FIG. 1A). The end effector 119 includes the upper slide 120 and lacks the lower slide 122 (FIG. 1A). The end effector 119 functions in a similar manner as that of the end effector 116. For example, the upper slide 120 is used to load or unload trays between the cassette 102 and the indexer 104.

It should be noted that in some embodiments, any number of slides for simultaneously transferring any number of trays may be used.

Figure 2:
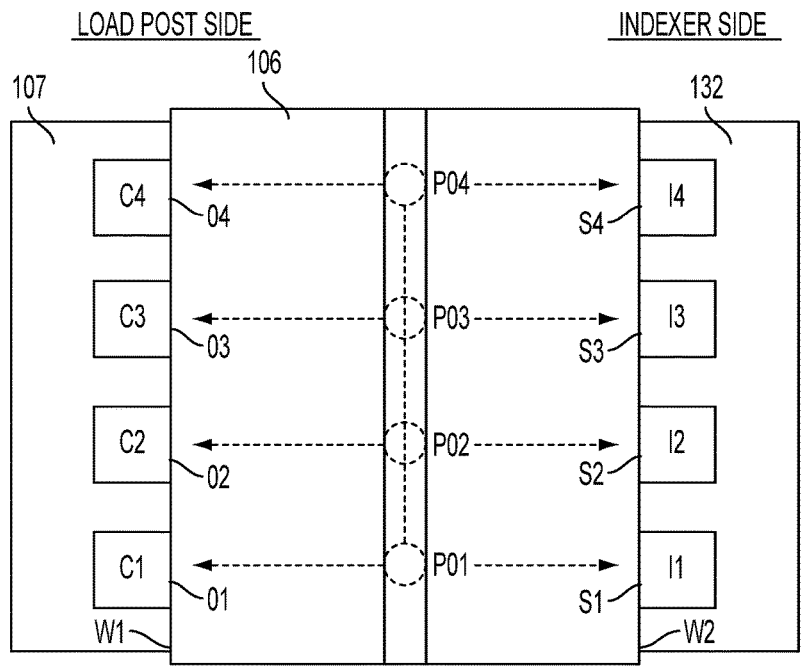
FIG. 2 is a top view of the sorter used to transfer trays between multiple cassettes and multiple indexers, in accordance with some embodiments described in the present disclosure.

FIG. 2 is a top view of an embodiment of the sorter 106. Four cassettes C1 thru C4 are placed on top of the shelf 107 and four indexers I1 thru I4 are placed on top of the shelf 132. Each cassette C1 thru C4 holds one or more trays and each indexer I1 thru I4 also holds one or more trays.

In several embodiments, one or more of the cassettes C1 thru C4 does not hold a tray and one or more of the indexers I1 thru I4 does not hold a tray.

The vertical driving column 114 (FIG. 1B) is driven by the column motor to be located at a position PO1, a position PO2, a position PO3, or a position PO4. The position PO1 is horizontally aligned with respect to the slot S1, the position PO2 is horizontally aligned with respect to a slot S2 within the side wall W2, the position PO3 is horizontally aligned with respect to a slot S3 within the side wall W2, and the position PO4 is horizontally aligned with respect to a slot S4 within the side wall W4.

Moreover, the position PO1 is horizontally aligned with respect to an opening O1 in the side wall W1, the position PO2 is horizontally aligned with respect to an opening O2 in the side wall W1, the position PO3 is horizontally aligned with respect to an opening O3 in the side wall W1, and the position PO4 is horizontally aligned with respect to an opening O4 in the side wall W1. The openings O1 thru O4 are created when doors of the sorter 106 open. For example, the opening O1 is formed when the door 124 (FIG. 1A) opens.

A tray can be transferred from the cassette C1 to any of the indexers I1 thru I4. For example, the vertical drive column 114 (FIG. 1B) is moved to the position PO1 to retrieve a tray from the cassette C1 and then moved from the position PO1 via the positions PO2 and PO3 to the position PO4 to deliver the tray to the indexer I4. In a number of embodiments, a tray can be transferred from the cassette C2 to any of the indexers I1 thru I4. For example, the vertical drive column 114 (FIG. 1B) is moved to the position PO2 to retrieve a tray from the cassette C2 and then moved from the position PO2 via the position PO3 to the position PO4 to deliver the tray to the indexer I4. In some embodiments, a tray can be transferred from the cassette C3 to any of the indexers I1 thru I4. In several embodiments, a tray can be transferred from the cassette C4 to any of the indexers I1 thru I4.

In some embodiments, a tray is transferred from the cassette C1 to any of the other cassettes C2 thru C4 by using one or more of the positions PO1 thru PO4. In several embodiments, a tray is transferred from the cassette C2 to any of the other cassettes C1, C3, and C4 by using one or more of the positions PO1 thru PO4. In various embodiments, a tray is transferred from the cassette C3 to any of the other cassettes C1, C2, and C4 by using one or more of the positions PO1 thru PO4. In several embodiments, a tray is transferred from the cassette C4 to any of the other cassettes C1, C2, and C3 by using one or more of the positions PO1 thru PO4.

Similarly, a tray is transferred from any of the indexers I1 thru I4 to any of the cassettes C1 thru C4. For example, the vertical drive column 114 (FIG. 1B) is moved to the position PO1 to retrieve a tray from the indexer I1 and then moved from the position PO1 via the positions PO2 and PO3 to the position PO4 to deliver the tray to the cassette C4. As another example, a tray is transferred from the indexer I2 to any of the cassettes C1 thru C4. As another example, a tray is transferred from the indexer I3 to any of the cassettes C1 thru C4. In several embodiments, a tray is transferred from the indexer I4 to any of the cassettes C1 thru C4.

In various embodiments, a tray is transferred from the indexer I1 to any of the other indexers I2 thru I4 by using one or more of the positions PO1 thru PO4. In various embodiments, a tray is transferred from the indexer I2 to any of the other indexers I1, I3, and I4 by using one or more of the positions PO1 thru PO4. In various embodiments, a tray is transferred from the indexer I3 to any of the other indexers I1, I2, and I4 by using one or more of the positions PO1 thru PO4. In several embodiments, a tray is transferred from the indexer I4 to any of the other indexers I1, I2, and I3 by using one or more of the positions PO1 thru PO4.

Figure 3:
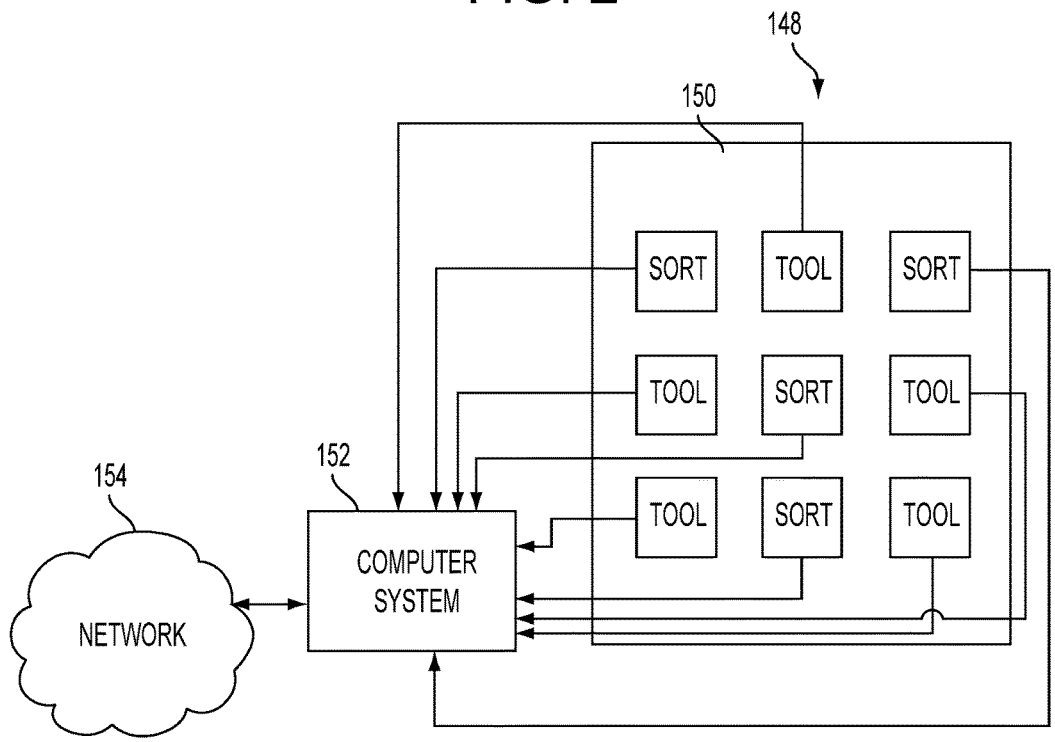
FIG. 3 is a top view of a system for identifying location of trays within a fabrication laboratory, in accordance with various embodiments described in the present disclosure.

FIG. 3 is a top view of an embodiment of a system 148 for identifying location of trays within a fabrication laboratory (fab) 150. The fab 150 includes multiple sorters and multiple tools, e.g., metrology tools, production tools, tools for processing wafers, tools for processing pharmaceutical drugs, tools for processing DNA samples, tools for processing light emitting diodes, tools for processing MEMS devices, etc. For example, the fab 150 includes a tool to clean a wafer die, a tool to retrieve a die from a tray, a tool to place a die into a compartment of a tray, a tool to clean a light emitting diode, etc.

The cameras, e.g., the cameras CAM1, CAM2 (FIG. 1B), etc., that are attached to doors of the sorter 106 (FIG. 2) capture images and transfer the images to a computer system 152. The computer system 152 includes one or more processors and one or more storage devices, which are computer-readable media. Examples of the computer system 152 include a desktop, a laptop, a workstation, etc.

As used herein, a processor may be an application specific integrated circuit (ASIC), a programmable logic device (PLD), a central processing unit (CPU), a microprocessor, etc.

Moreover, examples of a storage device include a read-only memory (ROM), a random access memory (RAM), or a combination thereof. For example, a storage device includes a flash memory, a redundant disk array, a hard disk, etc.

Cassettes and/or indexers are transferred between the sorters of the fab 150. In various embodiments, cassettes and/or indexers are transferred between the tools of the fab 150. In several embodiments, cassettes and/or indexers are transferred between the tools of the fab 150 and the sorters of the fab 150.

Identification of cassettes that are located within the fab 150 and that used to transfer trays within the fab 150 is stored in the storage device. For example, a code identifying a cassette and distinguishing the cassette within the fab 150 from another cassette within the fab 150 is stored in the storage device.

Moreover, identification of indexers that are located within the fab 150 and used to transfer trays within the fab 150 is stored in the storage device. For example, a code identifying an indexer and distinguishing the indexer within the fab 150 from another indexer within the fab 150 is stored in the storage device.

Also, information identifying the trays used within the fab 150 is stored in the storage device. For example, a barcode identifying a tray within the fab 150 and distinguishing the tray from another tray used within the fab 150 is stored in the storage device.

Moreover, identification of sorters that are located within the fab 150 and used to transfer trays within the fab 150 is stored in the storage device. For example, a code identifying a sorter and distinguishing the sorter within the fab 150 from another sorter within the fab 150 is stored in the storage device.

Furthermore, identification of tools that are located within the fab 150 and used to process trays within the fab 150 is stored in the storage device. For example, a code identifying a tool and distinguishing the tool within the fab 150 from another tool within the fab 150 is stored in the storage device.

Relationships between identification of cassettes and information identifying trays used within the fab 150 is also stored in the storage device. For example, a relationship indicating that a tray having an identification code aaaa is stored in a cassette having an identification code bbbb is stored in the storage device.

Moreover, relationships between identification of indexers and information identifying trays used within the fab 150 is also stored in the storage device. For example, a relationship indicating that a tray having the identification code aaaa is stored in an indexer having an identification code cccc is stored in the storage device.

Relationships between identification of sorters and information identifying trays used within the fab 150 is also stored in the storage device. For example, a relationship indicating that a tray having the identification code aaaa is being sorted in a sorter having an identification code dddd is stored in the storage device.

Moreover, relationships between identification of cameras and information identifying doors of sorters on which the cameras are located is also stored in the storage device. For example, a relationship indicating that a camera having an identification code eeee is located on a sorter door having an identification code ffff is stored in the storage device.

Also, relationships between identification of readers and information identifying indexers on which the readers are placed is also stored in the storage device. For example, a relationship indicating that a reader having an identification code gggg is located on an indexer having an identification code hhhh is stored in the storage device. Examples of a reader include a scanner, a camera, etc. The readers are further described below.

When a tray is transferred from a cassette to the sorter, a camera of the sorter captures an image of information identifying the tray from the tray and sends the image to the computer system 152. When the image is received, the processor of the computer system 152 determines that the tray identified by the information is no longer stored in the cassette and is transferred from the cassette to a sorter in which the camera is located.

Similarly, when a tray is transferred from a sorter to an indexer, a reader of the indexer reads information identifying the tray and sends the information to the computer system 152. Upon receiving the information identifying the tray, the processor of the computer system 152 determines that the tray is being stored in the indexer.

Information regarding a location of a tray within a sorter, within an indexer, a tool, within a cassette, etc. may be sent from the computer system 152 via a network 154 to another computer system (not shown). Examples of the network 154 include a local area network, a wide area network, etc. The network 154 and the computer system 152 may be a part of the Internet or an Intranet.

Figure 4A:
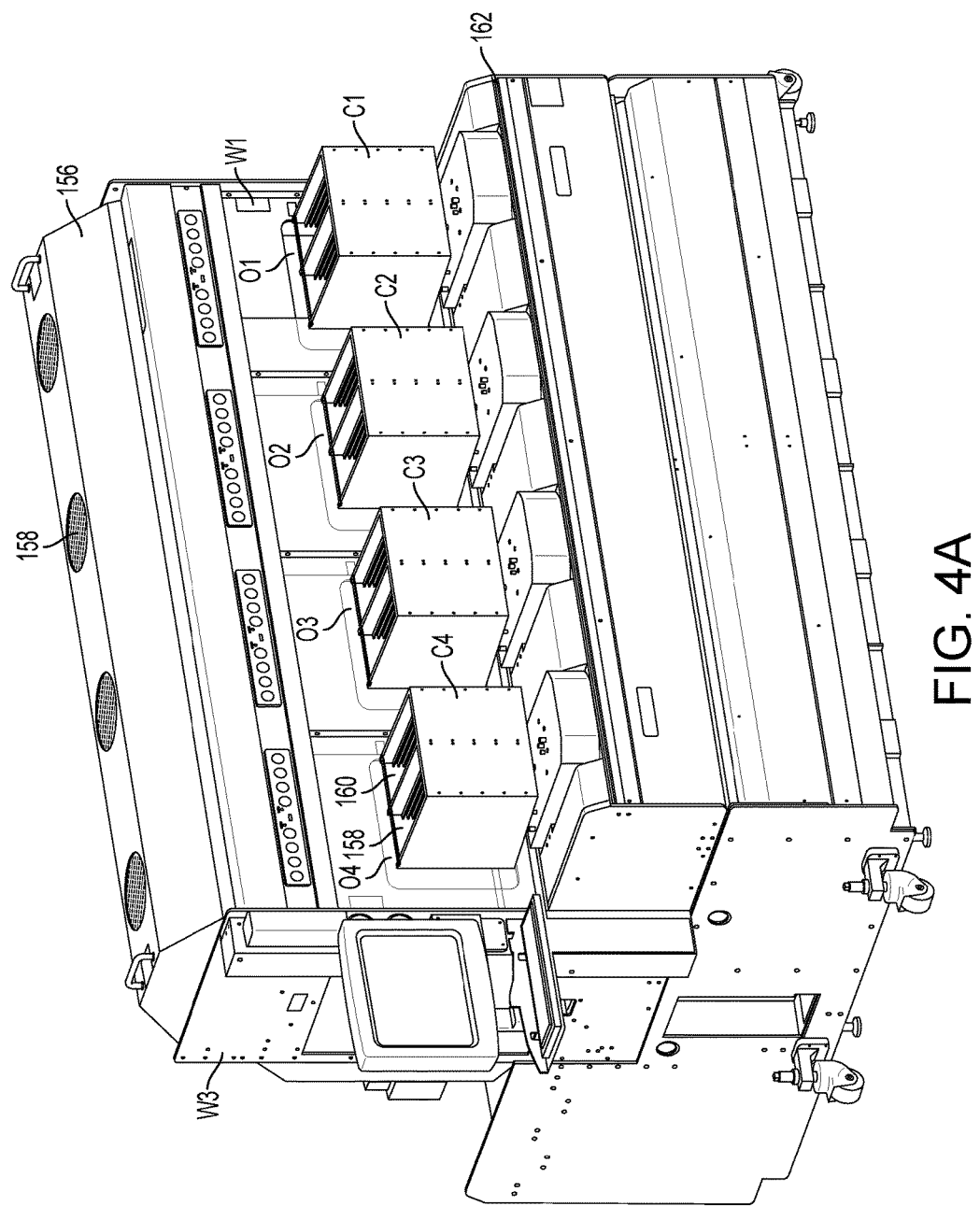
FIG. 4A is an isometric view of a side of an equipment front end module (EFEM), in accordance with several embodiments described in the present disclosure.

FIG. 4A is an isometric view of an embodiment of a load port side of an equipment front end module (EFEM) 156, which is an example of the sorter 106 (FIG. 1A) and of the sorter 117 (FIG. 1C). The EFEM 156 includes an air inlet 158 that allows air to flow into the EFEM 156. The air that flows into the EFEM 156 is filtered and used to remove contamination from trays and the air is blown to remove the contamination out of the EFEM 156. For example, the air is filtered using ultra-low particulate air (ULPA) filters. In some embodiments, the air that flows into the EFEM 156 is filtered to reduce chances of, e.g., prevent, etc., contamination of air within the EFEM 156.

As shown, doors of the EFEM 156 are lowered down to form the openings O1, O2, O3, and O4 in the wall W1. Trays are transferred between one or more of the cassettes C1 thru C4 and the EFEM 156 via one or more of the corresponding openings O1 thru O4.

In various embodiments, the EFEM 156 includes temperature and/or humidity controls. In some embodiments, the EFEM 156 includes provision of gases, e.g., argon, helium, nitrogen, etc., to protect the die within the EFEM 156. In a variety of embodiments, the gases may be employed using a recirculation approach.

The cassette C4 includes two slots 159 and 160 and is supported on a shelf 162, which is an example of the shelf 107 (FIG. 1A). Similarly, the cassettes C1 thru C3 include two slots and are supported on the shelf 162.

In some embodiments, each cassette C1 thru C4 includes any other number of slots, e.g., one slot, three slots, etc.

A wall W3 of the EFEM 156 is substantially perpendicular to the wall W1 and to the wall W2 (FIG. 1A).

Figure 4B:
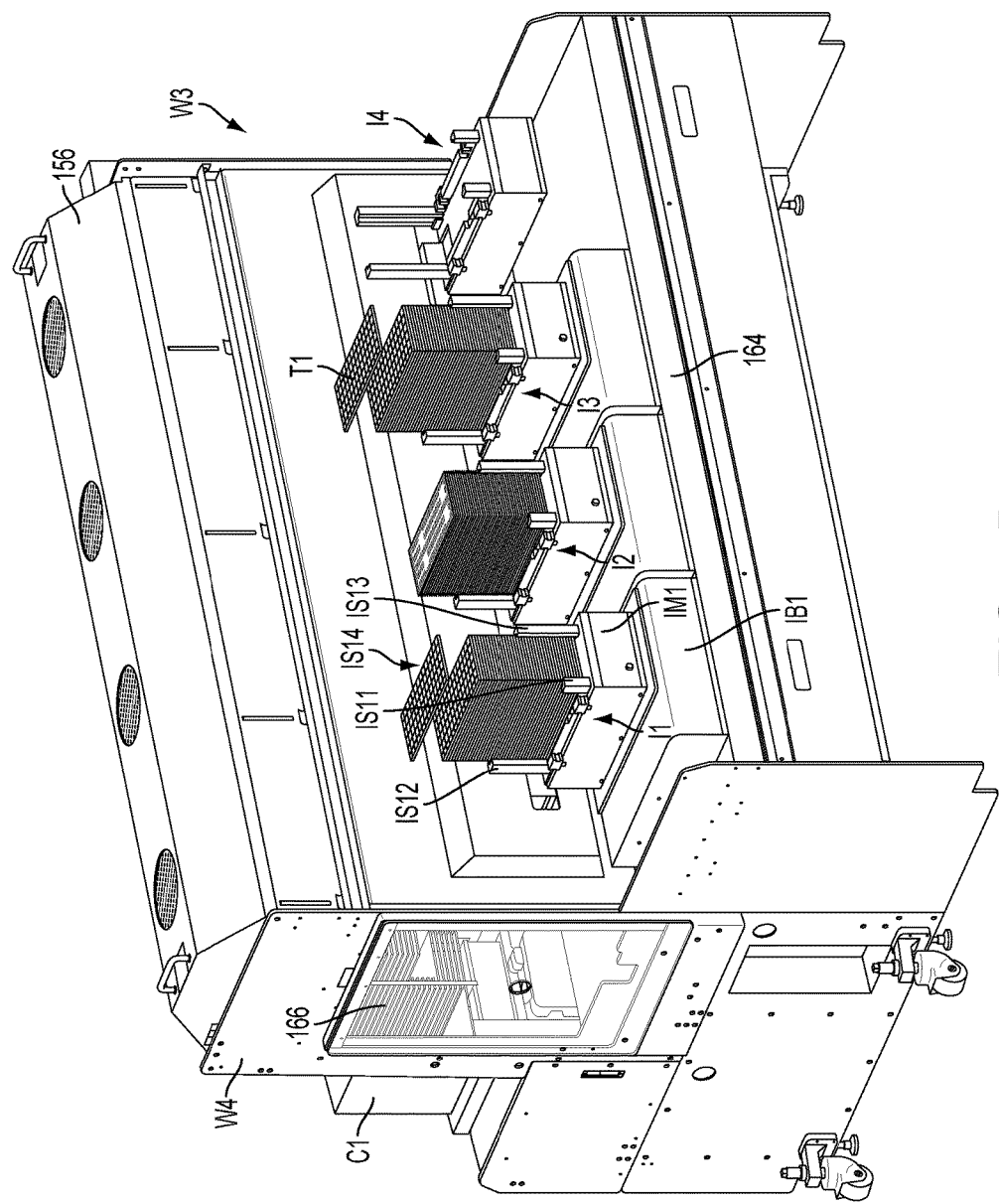
FIG. 4B is an isometric view of another side of the EFEM, in accordance with some embodiments described in the present disclosure.

FIG. 4B is an isometric view of an embodiment of an indexer side of the EFEM 156. The indexers I1 thru I4 are supported on a shelf 164, which is an example of the shelf 132 (FIG. 1A).

As shown, trays are stacked on top of the indexer I1. For example, trays are stacked on top of an indexer module IM1, which is located on top of an indexer base IB1. The stack of trays on top of the indexer I1 is supported by indexer supports IS11, IS12, IS13, and IS14, which is not visible in FIG. 4B. For example, the indexer supports IS11, IS12, IS13, and IS14 reduce chances of the stack of trays from falling off the indexer module IM1. The indexer supports IS11, IS12, IS13, and IS14 are supports of the indexer 104.

In some embodiments, the terms indexer columns and indexer supports are used interchangeably herein.

In several embodiments, an indexer may include any other number of supports. For example, the indexer I1 includes three, five, or six supports to support a stack of trays on top of the indexer module IM1.

A view window 166 is located on a wall W4 of the EFEM 156. The wall W4 is substantially parallel to the wall W3 and is substantially perpendicular to the wall W1 and to the wall W2 (FIG. 1A). The view window 166 provides a view of the cassette C1 that is supported on the shelf 162.

In some embodiments, the EFEM 156 does not include the view window 166.

Figure 4C:
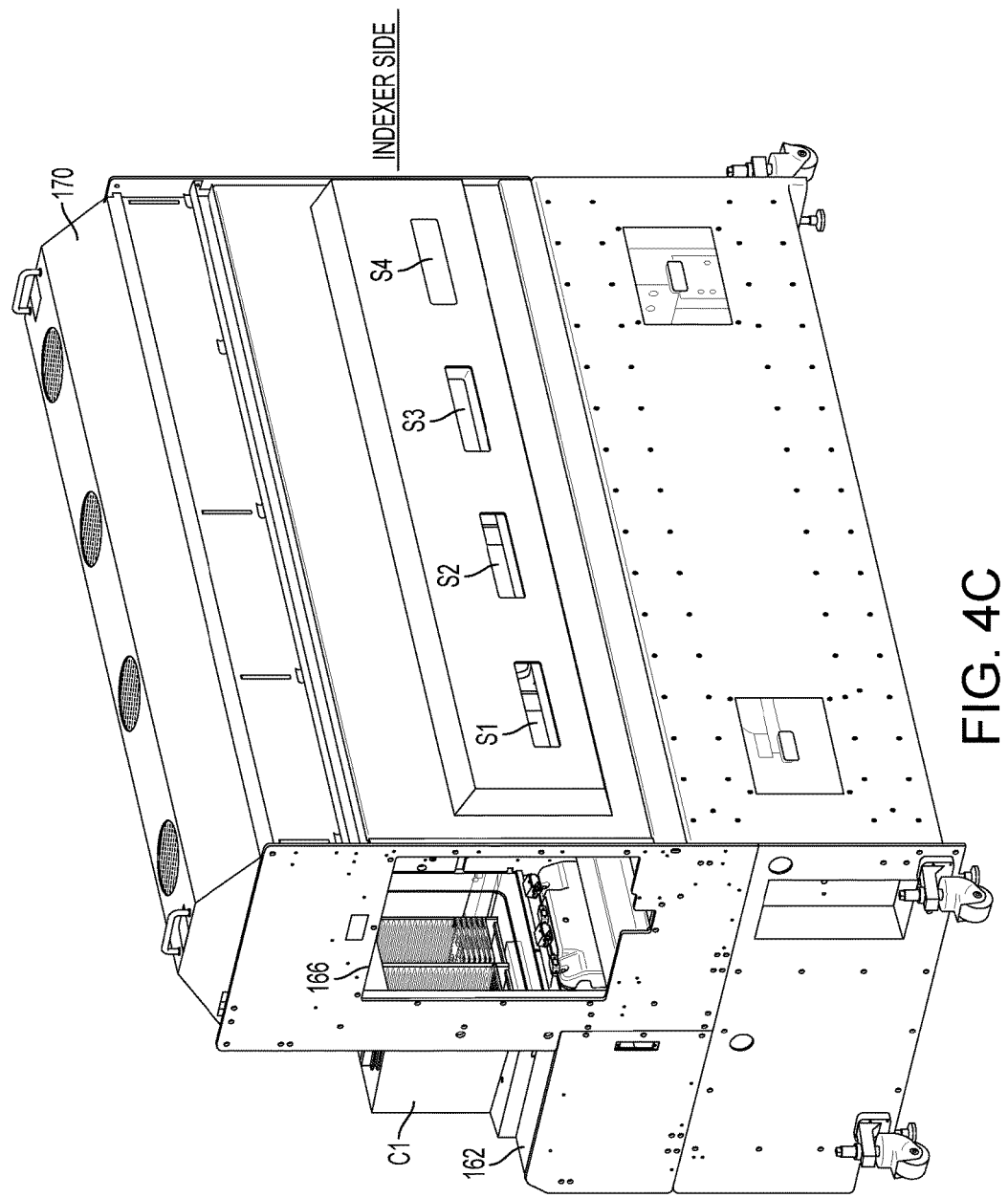
FIG. 4C is an isometric view of a side of the EFEM, in accordance with various embodiments described in the present disclosure.

FIG. 4C is an isometric view of an EFEM 170 that excludes a shelf on the indexer side. As shown, the four slots S1 thru S4 allow passage of trays between the EFEM 170 and indexers I1 thru I4 (FIG. 4B).

FIG. 5A is an isometric view of an embodiment of a system 174 for transferring trays between the tray engine 108 and the cassette 102. The vertical drive assembly is fixed to the end effector base 118. A top slider block 176 of the end effector 116 is slidably attached to an edge of the end effector base 118. For example, the top slider block 176 slides with respect to a slide base 188 within the end effector base 118. Examples of the slide base 188 include a rail, a track, a base with a slot for sliding, etc. The slide base 188 is located within and attached to the end effector base 118. In some embodiments, the top slider block 176 may be attached to or may include rollers to allow the top slider block 176 to slide on the slide base 188.

Similarly, a bottom slider block (not visible in FIG. 5A) of the end effector 116 is slidably attached to an opposite edge of the end effector base 118 via a bottom slider block (not visible in FIG. 5A). The opposite edge is opposite to an edge of the end effector base 118 at which the top slider block 176 is located. In some embodiments, the bottom slider block may be attached to or may include rollers to allow the bottom slider block to slide on a slide base located on a side of the end effector base 118 opposite to a side on which the slide base 188 is located.

In some embodiments, the top slider block 176 and the bottom slider block slide along the length 1 of the end effector base 118 to slide in a linear direction.

A top connector block 178 of the end effector 116 is fixed on top of the top slider block 176 and a bottom connector block (not visible in FIG. 5A) of the end effector 116 is attached on top of the bottom slider block.

The top driving plate 144 is attached, e.g., via one or more screws, etc., to top of the top connector block 178. Similarly, the bottom driving plate 146 is attached, e.g., via one or more screws, etc., to top of the bottom connector block. The top driving plate 144 is located on top of the bottom driving plate 146.

The top slider block 176, the top connector block 178, and the top driving plate 144 are examples of a linear drive mechanism and slide in a linear direction. For example, the top slider block 176 and the connector block 178 slide towards or away from the load port side or towards or away from the indexer side.

Similarly, the bottom slider block, the bottom connector block, and the bottom driving plate 146 are examples of a linear drive mechanism and slide in a linear direction. For example, the bottom slider block and the bottom connector block slide towards or away from the load port side or towards or away from the indexer side.

In some embodiments, instead of using two blocks, e.g., the top slider block 176 and the connector block 178, to connect the slide base 188 to the top driving plate 144, any other number of connector blocks are used. Similarly, instead of using two blocks, e.g., the bottom slider block and the bottom connector block to connect the other slide base to the bottom driving plate 146, any other number of connector blocks are used.

An upper grip assembly 180 is attached to the top driving plate 144 and a lower grip assembly 182 is attached to the bottom driving plate.

In some embodiments, the upper grip assembly 180 is coplanar with the upper slide 120 and the lower grip assembly 182 is coplanar with the lower slide 122.

Multiple slide supports SS1, SS2, SS3, and SS4 are attached on top of the end effector base 118. The slide support SS4 is located on an opposite side of the end effector base 118 compared to the side of the end effector base 118 to which the slide supports SS1, SS2, and SS3 are attached. The slides supports SS1 thru SS4 facilitate constraining movement of trays moving on the slides 120 and 122 to a linear motion to prevent the trays from falling off the slides 120 and 122.

The slides 120 and 122 are attached to the slide supports SS1, SS2, SS3, and SS4. The slide supports SS1, SS2, SS3, and SS4 provide support to trays that slide between arms A11 and A12 of the upper slide 120 and that slide between arms A21 and A22 (shown in FIG. 5B) of the lower slide 122.

Also, attached at a bottom of the end effector base 118 is an end effector drive motor 184.

The vertical drive column 114 is driven by the vertical drive motor (not shown) that drives the vertical column 114 up and down with respect to a base (not shown) of the tray engine 108. With the movement of the vertical drive column 114, the end effector 116 moves up and down vertically.

When a tray is supported between arms A21 and A22 of the lower slide 122 and the tray is to be transferred to the cassette 102, the lower slide 122 is vertically positioned at a level of a pair of supports of the cassette 102 and the pair of supports lacks a tray between the supports. Also, when a tray is supported between the arms A11 and A12 of the upper slide 120 and the tray is to be transferred to the cassette 102, the upper slide 120 is vertically positioned at a level of a pair of supports of the cassette 102 and the pair lacks a tray between the supports.

Moreover, when a tray is to be received from the cassette 102, the lower slide 122 is vertically positioned at a level of a pair of supports of the cassette 102 and the pair supports the tray between the supports. Also, when a tray is to be received from the cassette 102, the upper slide 120 is vertically positioned at a level of a pair of supports of the cassette 102 and the pair supports the tray between the supports.

Also, the theta motor 112 rotates the end effector 116 with the vertical drive column 114 to position an edge E11 of the arm A11 and an edge E12 of the arm A12 to face the slot SO1 and to position an edge E21 of the arm A21 and an edge E22 of the arm A22 to face the slot SO1.

The top slider block 176 slides along the slide base 188, via a slide mechanism, e.g., rollers, roller balls, etc., within the end effector base 118 to slide the top driving plate 144 towards or away from the slot SO1. Similarly, the bottom slider block slides along the slide base on an opposite side of the end effector base 118 to slide the bottom driving plate 146 towards or away from the slot SO1.

When the top driving plate 144 moves linearly and horizontally towards a level within the slot SO1, the upper grip assembly 180 also moves linearly in a horizontal direction towards the level within the slot SO1 to slide a tray supported between the arms A11 and A12 towards the level within the slot SO1. Moreover, when the bottom driving plate 146 moves linearly and horizontally towards a level within the slot SO1, the lower grip assembly 182 also moves linearly in a horizontal direction towards the level within the slot SO1 to slide a tray supported between the arms A21 and A22 towards the level within the slot SO1.

Similarly, when the top driving plate 144 moves linearly and horizontally away from a level within the slot SO1, the upper grip assembly 180 also moves linearly and horizontally away from the level within the slot SO1 to slide a tray to be supported between the arms A11 and A12 away from the level within the slot SO1. Moreover, when the bottom driving plate 146 moves linearly and horizontally away from a level within the slot SO1, the lower grip assembly 182 also moves linearly and horizontally away from the level within the slot SO1 to slide a tray to be supported between the arms A21 and A22 away from the level within the slot SO1.

In some embodiments, when a tray slides with respect to the upper slide 120, the tray is supported by the supports SS1, SS2, SS3, and SS4 until the tray is supported by supports within the cassette 102. Similarly, when a tray slides with respect to the lower slide 122, the tray is supported by the supports SS1, SS2, SS3, and SS4 until the tray is supported by supports within the cassette 102.

It should be noted that the top slider block 176 and the bottom slider block are in a retracted position P1.

Figure 5B:
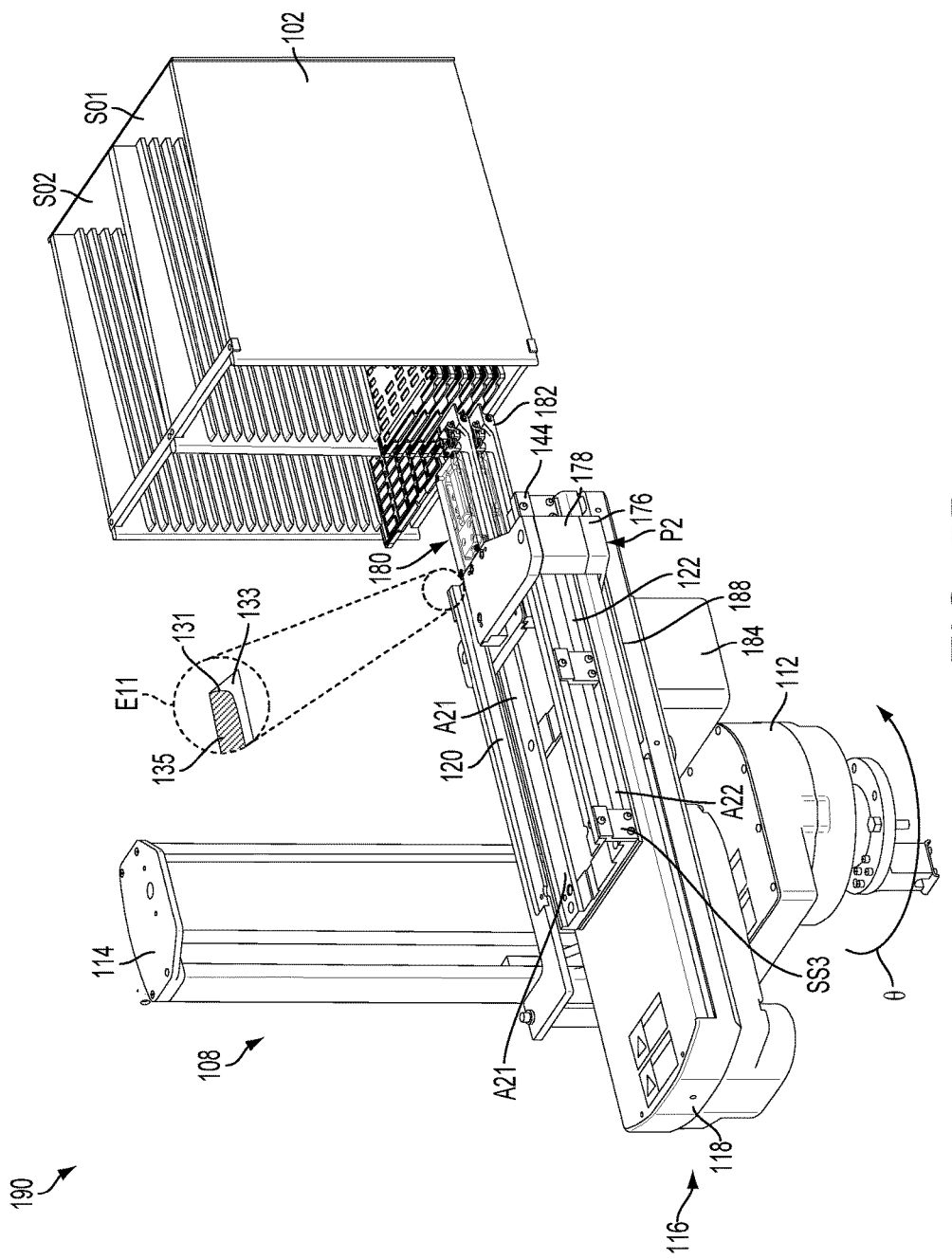
FIG. 5B is an isometric view of the tray engine, in accordance with various embodiments described in the present disclosure.

FIG. 5B is an isometric view of an embodiment of a system 190 that illustrate use of the tray engine 108 to insert a tray within the cassette 102. As shown, the top driving plate 144 and the bottom driving plate 146 slide to an extended position P2 from the retracted position P1. When the plates 144 and 146 are at the extended position P2, the plates 144 and 146 are closer to the edges E11, E12, E21, and E22 (FIG. 5A) of the arms A11, A12, A21, and A22 compared to when the plates 144 and 146 are at the retracted position P1.

When the plates 144 and 146 are at the extended position P2, the upper grip assembly 180 and the lower grip assembly 182 are extended towards a level within the slot SO1 at which a tray is to be placed or from which a tray is to be retracted.

As shown in a zoom-in window, the edge E11 is tapered to form a slide taper 131 to facilitate reception of a tray from the indexer 104. For example, the edge E11 is curved at the slide taper 131 to allow smooth reception of a tray. When a tray is received via the edge E11, the tray is supported on a slide surface 133 of the upper slide 120.

In several embodiments, the other edges E12, E21, and E22 are also tapered in a manner similar to that the edge E11.

In some embodiments, the slides 120 and 122 have upper retention surfaces in addition to side and lower retention surfaces. For example, in addition to the slide surface 133 and a side surface 135, the slide 120 has an upper surface that facilitates retention of a tray or retention of the tray and a tray lid between the upper surface and the slide surface 133. The upper surface may be substantially perpendicular to the side surface 135 and substantially parallel to the slide surface 133.

FIG. 6A is an isometric view of an embodiment of a portion 202 of the EFEM 156 (FIG. 4A) to illustrate use of the cameras CAM1 and CAM2 and sensors SE1 and SE2. The portion 202 includes the opening O4.

As shown, the cameras CAM1, CAM2, and the sensors SE1 and SE2 are attached via an attachment mechanism to the top surface 140 of the door 124.

When the cassette C1 approaches the door 124, the door 124 is driven down by the door motor to form the opening O4. Simultaneous with the formation of the opening O4, the sensor SE1 senses whether a tray is present or absent at all levels of the slot SO1 and the sensor SE2 senses whether a tray is present or absent at all levels of the slot SO2.

In some embodiments, a level of a slot is a horizontal level of two supports, e.g., supports SU131 and SU132, of the slot.

The sensor SE2 sends an indication that a tray is sensed at a level of the slot SO2 to the computer system 152 (FIG. 3). The computer system 152 sends a signal to the camera CAM2 to take an image of the tray that is sensed.

Upon receiving a signal indicating that a tray, e.g., the tray T1, is present at a level within the slot SO2, the camera CAM2 takes an image of information identifying the tray. The camera CAM2 sends the image to the computer system 152 for storage and further execution.

Figure 6B:
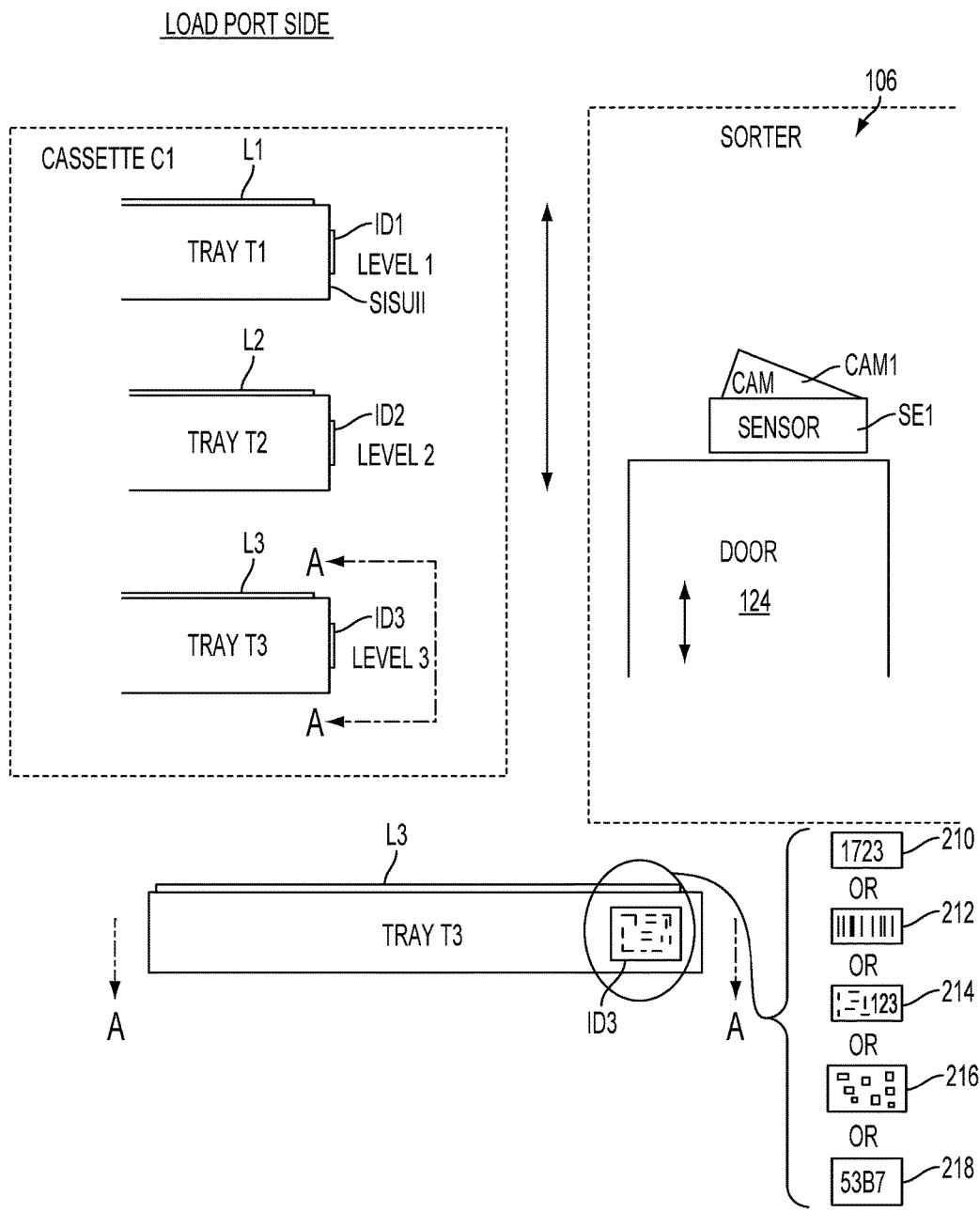
FIG. 6B is a diagram of a load port side of the EFEM to illustrate different types of information identifying marks that are used to identify a tray, in accordance with some embodiments described in the present disclosure.

FIG. 6B is a diagram of an embodiment of the load port side to illustrate different types of information identifying marks that are used to identify a tray. As shown, the sensor SE1 senses presence or absence of the tray T2 at a level 2 within the cassette C1. When the sensor SE1 senses the presence or absence of the tray T2 at the level 2, the camera CAM1 captures an image of an identification mark ID1 on a side surface SISU11 of the tray T1 at a level 1.

In some embodiments, an identification mark is attached to a top surface of a tray instead of a side surface of the tray.

In various embodiments, an identification mark is attached to a bottom surface of a tray instead of the top or side of the tray.

In several embodiments, an identification mark is imprinted on a surface of a tray. In various embodiments, an identification mark is imprinted on a tag that is attached to a surface of a tray.

As the door 124 moves vertically down, the sensor SE1 senses presence or absence of the tray T2 and of the tray T3. Moreover, as the door 124 moves vertically down, the camera CAM1 takes an image of an identification mark ID2 attached to a side surface of the tray T2 and of an identification mark ID3 attached to a side surface of the tray T3 at a level 3.

As shown, the camera CAM1 is angled with respect to the sensor SE1 to allow the camera CAM1 to capture an image of the identification mark ID1 at the level 1 at a time the sensor SE1 senses presence or absence of the tray T2 at the level 2.

In various embodiments, the camera CAM1 forms an angle with respect to the sensor SE1 to capture an image at a level that is above any number of levels from a level at which the sensor SE1 detects. For example, the camera CAM1 is angled with respect to the sensor SE1 to allow camera CAM1 to capture at image of the identification mark ID1 at the level 1 at a time the sense SE1 senses presence or absence of the tray T3 at the level 3. As another example, the camera CAM2 forms an angle between zero and eighty-nine degrees with respect to the sensor SE1.

The identification marks ID3 may be a numeric identification mark, e.g., an identification mark 210 that includes numbers, or a barcode, e.g., a barcode 212, or a combination of a barcode and numbers, e.g., an identification mark 214, or an EZ code, e.g., a two-dimensional code 216, or an alphanumeric code, e.g., a code 218. Other types of barcodes include an Aztec symbol, a high capacity color barcode, a quick response (QR) code, a MaxiCode, a ShotCode, etc.

FIG. 6C is an isometric view of an embodiment of a portion 217 of the EFEM 156 (FIG. 4A) to illustrate a close-up of the cameras CAM1 and CAM2 and sensors SE1 and SE2.

Figure 6D:
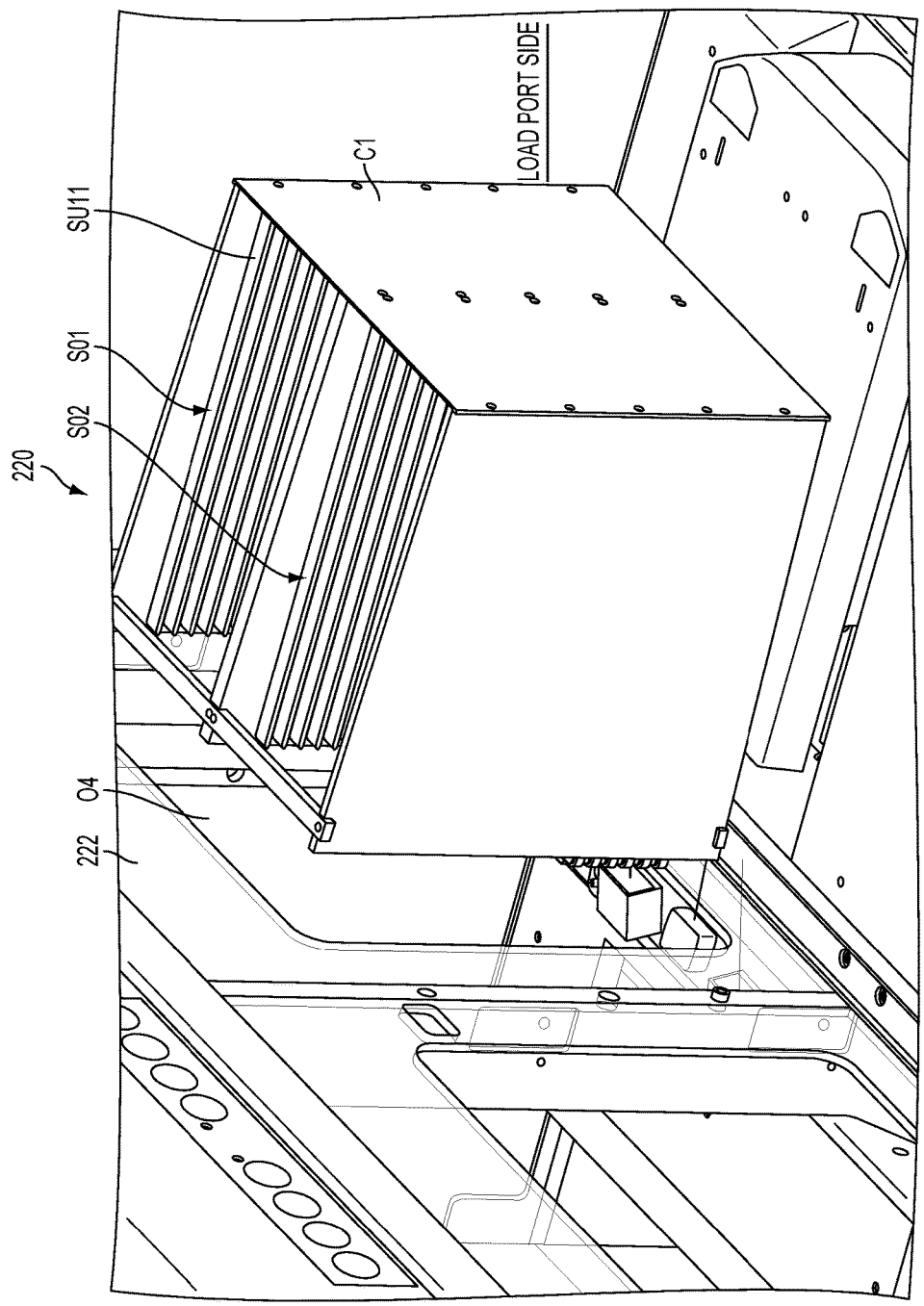
FIG. 6D is an isometric view of a portion of the EFEM to illustrate a use the cameras and sensors, in accordance with various embodiments described in the present disclosure.

FIG. 6D is an isometric view of an embodiment of the load port side of a portion 220 of the EFEM 156 (FIG. 4A). The cassette C1 includes a top support SU11 that supports a tray. As shown, the cassette C1 is positioned close to the opening O4 to facilitate unloading of a tray from the cassette C1 or loading of a tray to the cassette C1. In some embodiments, the cassette C1 is placed within a pre-determined distance of a film 222 that surrounds the opening O4. The film 222 is made of a flexible material, e.g., polyethylene, nylon, synthetic material, thermoplastics, thermosetting polymers, a combination thereof, etc.

In various embodiments, the EFEM 156 excludes a film at an opening that is formed by opening a door of the EFEM 156.

FIG. 7A is a top view of an embodiment of a portion 230 of the indexer side when the plates 144 and 146 are in the retracted position P1. The portion 230 is used to illustrate a transfer of a tray between the EFEM 156 and the indexer 104. The indexer 104 rests on the indexer base IB1.

The theta motor 112 (FIG. 1A) rotates the vertical drive column 114 so that the edges E11 and E12 face the indexer 104 via the slot S1 on the indexer side of the EFEM 156. Also, the vertical drive motor drives the vertical drive column 114 to position the edges E11 and E12 at a level of the slot S1. The driving plates 144 and 146 are driven by the end effector drive motor 184 (FIG. 5A) to slide the top slider block 176 (FIG. 5A) and the bottom slider block along the slide base 188 and another slide located opposite to the slide base 188. The top and bottom slider blocks slide towards the indexer 104. The slides 120 and 122 extend through the slot S1. The upper grip assembly 180 grips the tray T2 that is covered with a tray lid L2.

Figure 7B:
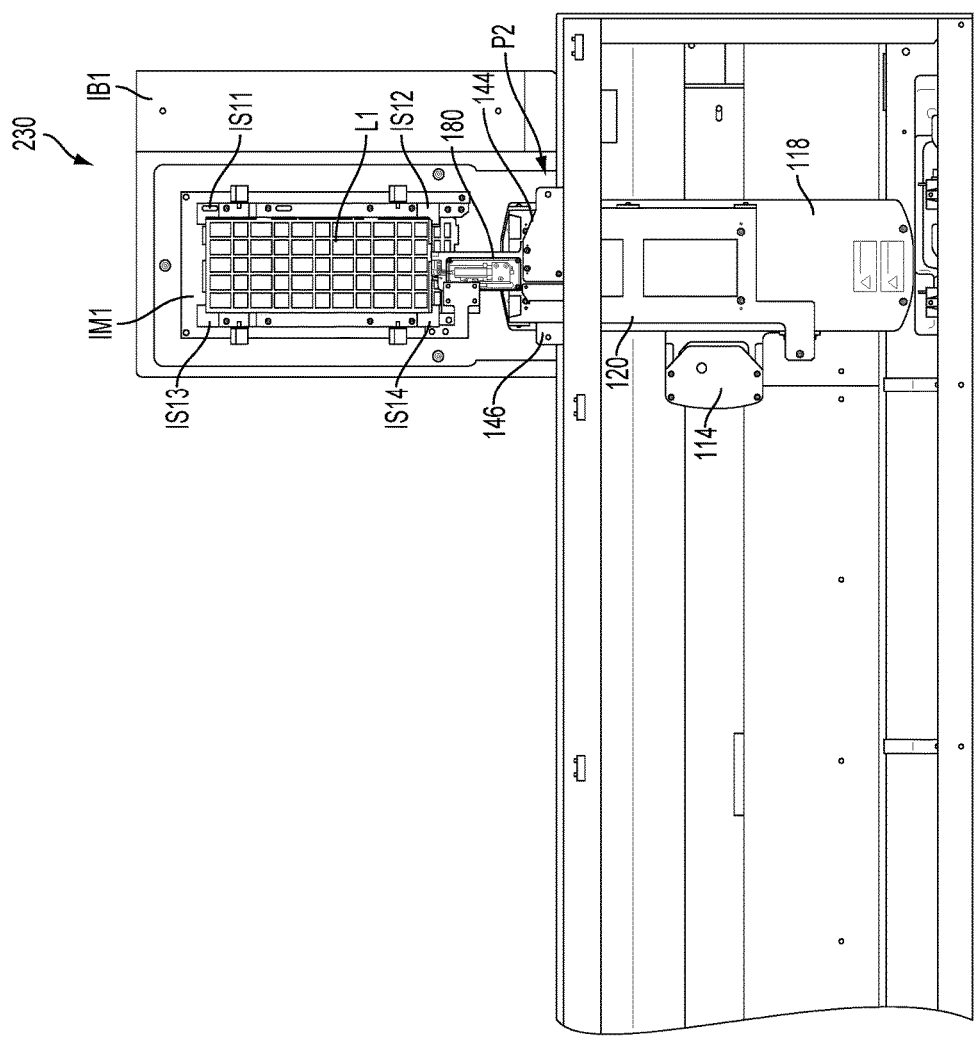
FIG. 7B is a view of the indexer side of the EFEM to illustrate a transfer of trays between the EFEM and the indexer, in accordance with some embodiments described in the present disclosure.

When the driving plates 144 and 146 move towards the indexer from the retracted position P1, the tray T2 and the tray lid L2 slide towards the indexer 104 via the slot S1 until the driving plates 144 and 146 reach the extended position P2, which is shown in FIG. 7B. The tray T2 may slide on top of another tray in the indexer 104. Also, the grip assemblies 180 and 182 (FIG. 5A) pass through the slot S1 when the driving plates 144 and 146 move from the retracted position P1 to the extended position P2.

FIG. 7B is a top view of an embodiment of the portion 230 when the plates 144 and 146 are in the extended position P2. In the extended position P2, grip assemblies 180 and 182 (FIG. 5A) have extended through the slot S1 to reach the indexer 104. When the plates reach the extended position P2 from the retracted position P1, the tray T1 slides from the upper slide 120 to the indexer 104 to be placed on top of the tray lid L1 in the indexer 104 or on top of the base of the indexer module IM1.

Similarly, in some embodiments, the tray T2 is retrieved from the indexer 104 and placed in the EFEM 156. For example, the vertical drive column 114 is driven by the vertical drive motor to change a level of the grip assemblies 180 and 182 (FIG. 5A) to obtain one or two trays from the indexer 104. The grip assemblies 180 and 182 grip trays from between the indexer supports IS11, IS12, IS13, and IS14. The end effector drive motor 184 (FIG. 5A) drives the top slider block 176 and the bottom slider block and the gripped trays slide from the indexer 104 towards the EFEM 156 via the slot S1 to facilitate the driving plates 144 and 146 to reach the retracted position P1 from the extended position P2. Also, the grip assemblies 180 and 182 pass via the slot S1 when the top slider block 176 and the bottom slider block slide towards the EFEM 156. The gripped trays slide from the indexer 104 towards the slides 120 and 122 (FIG. 5A). For example, the gripped trays slide from being on top of another tray in the indexer 104 towards the slides 120 and 122. The edges E11, E12, E21, and E22 facilitate reception of the gripped trays from the indexer 104 onto the slides 120 and 122. The driving plates 144 and 146 reach the retracted position P1 from the extended position P2.

Figure 7C:
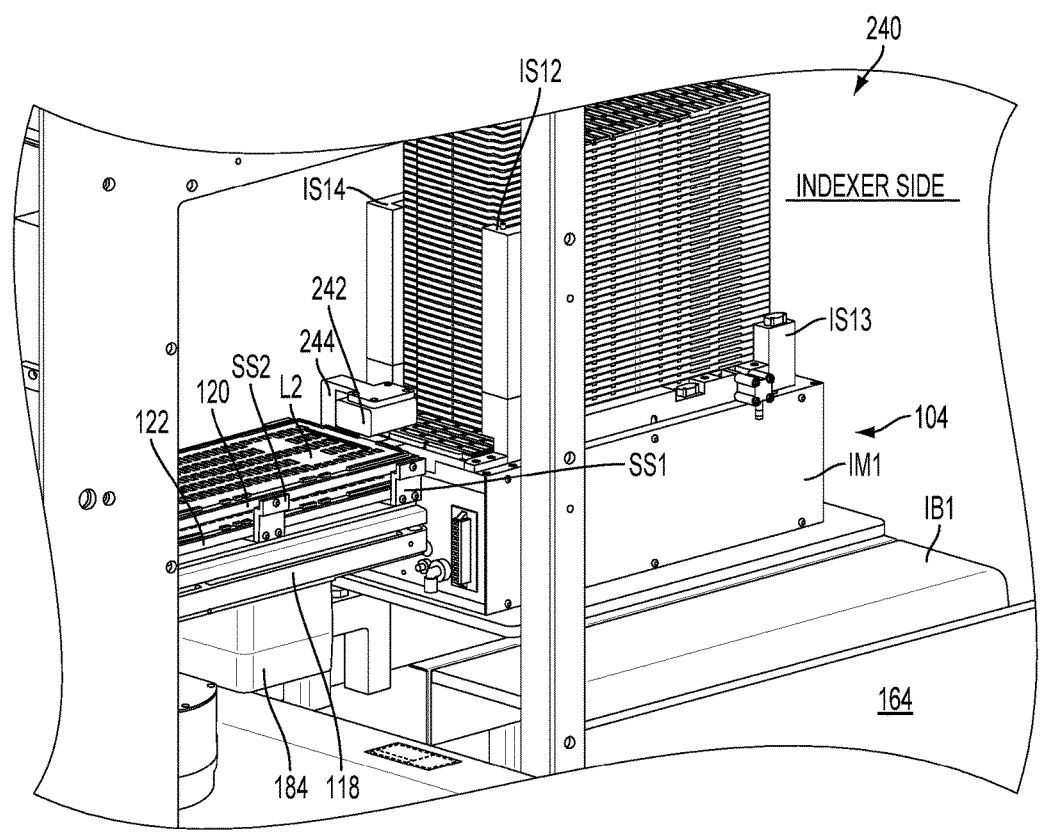
FIG. 7C is a view of the indexer side of the EFEM to illustrate a transfer of trays between the EFEM and the indexer, in accordance with various embodiments described in the present disclosure.

FIG. 7C is an isometric view of an embodiment of a portion 240 of the indexer side to illustrate use of a reader 242 between the EFEM 156 (FIG. 4A) and the indexer 104. The reader 242 is attached via a connector 244 to the indexer 104. For example, the connector 244 is attached to the indexer module IM1 and the reader 242 is attached, via an attachment mechanism to the connector 244.

When a tray is transferred between the indexer 104 and the EFEM 156, e.g., unloaded from the EFEM 156 to the indexer 104, loaded from the indexer 104 to the EFEM 156, etc., the reader 242 reads the information identifying the tray. The reader 242 sends the information to the computer system 152 (FIG. 3) to facilitate determination of a location of the tray, e.g., whether the tray is in the indexer 104 or in the EFEM 156.

As shown, a tray is to be loaded into the indexer 104 from the slides 120 and 122.

Figure 7D:
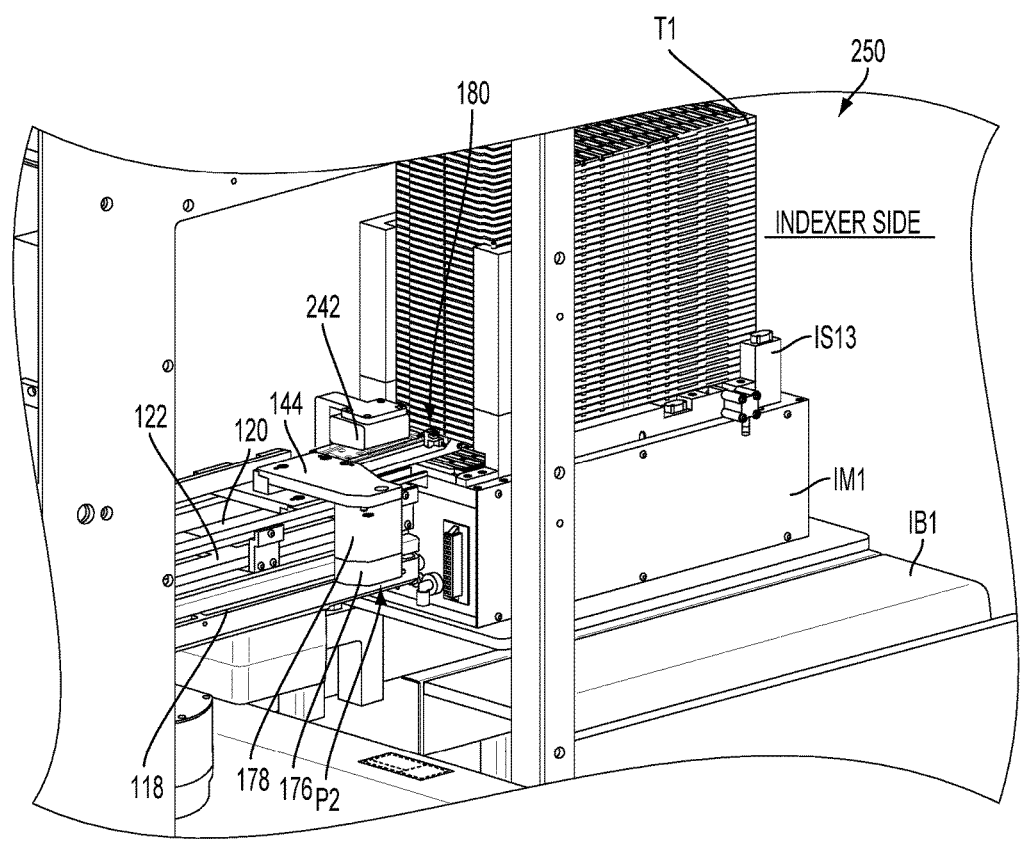
FIG. 7D is a view of the indexer side of the EFEM to illustrate a transfer of trays between the EFEM and the indexer, in accordance with several embodiments described in the present disclosure.

FIG. 7D is an isometric view of an embodiment of a portion 250 of the indexer side to illustrate use of the reader 242 between the EFEM 156 (FIG. 4A) and the indexer 104 and to illustrate the extended position P2 of the driving plates 144 and 146 during loading a tray into the indexer 104 or unloading a tray from the indexer 104. As shown, the top driving plate 144 is in the position P2 and a tray is loaded into the indexer 104.

In some embodiments, when the top driving plate 144 is in the position P2, a tray is to be retrieved from the indexer 104.

Figure 7E:
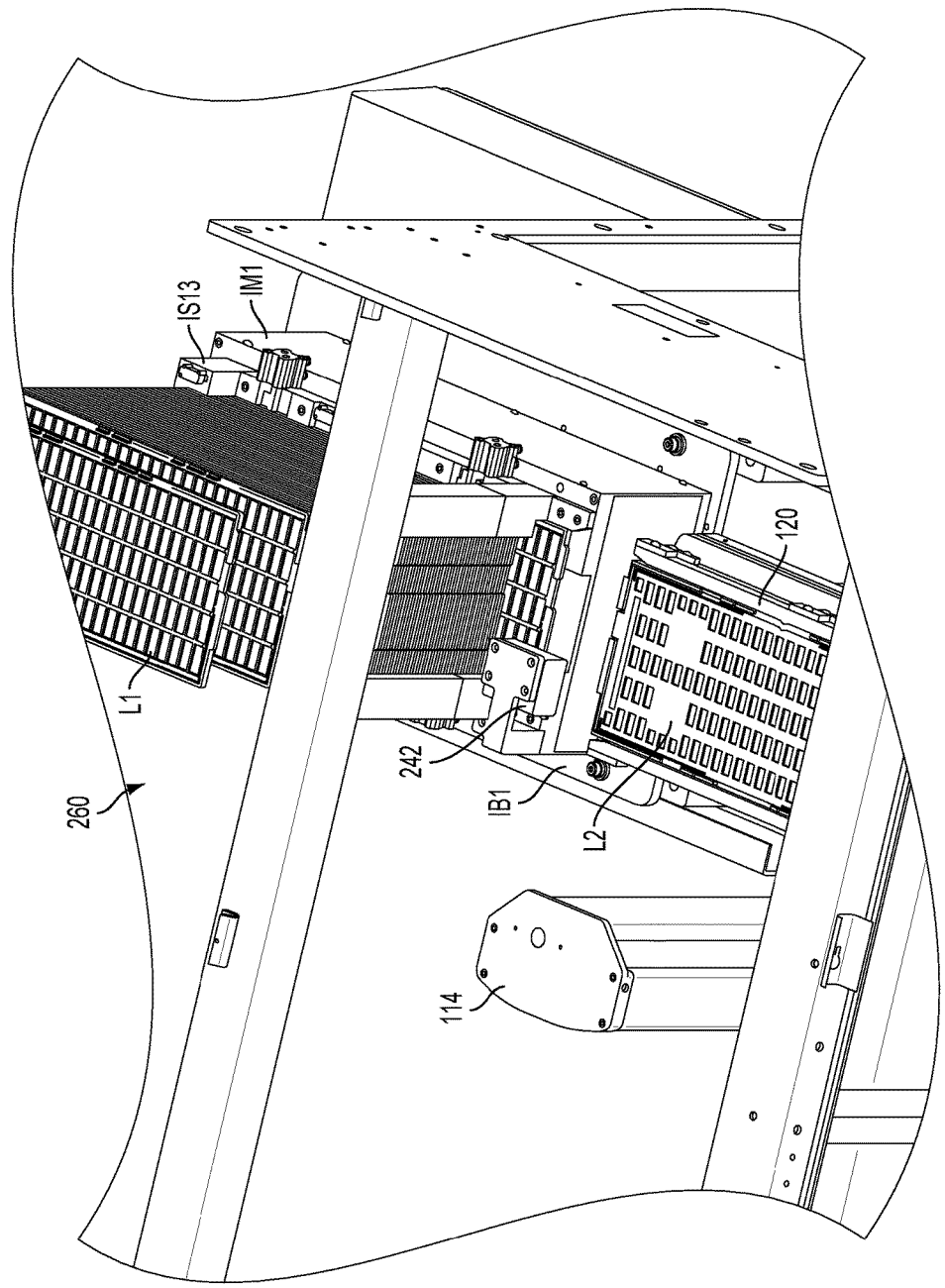
FIG. 7E is a view of the indexer side of the EFEM to illustrate a transfer of trays between the EFEM and the indexer, in accordance with some embodiments described in the present disclosure.

FIG. 7E is a top isometric view of an embodiment of a portion 260 of the indexer side to illustrate use of the reader 242 between the EFEM 156 (FIG. 4A) and the indexer 104.

FIG. 7F is a top isometric view of an embodiment of a portion 270 of the indexer side to illustrate use of the reader 242 between the EFEM 156 (FIG. 4A) and the indexer 104 and to illustrate a position of the driving plates 144 and 146 during loading a tray into the indexer 104 or unloading a tray from the indexer.

Figure 7G:
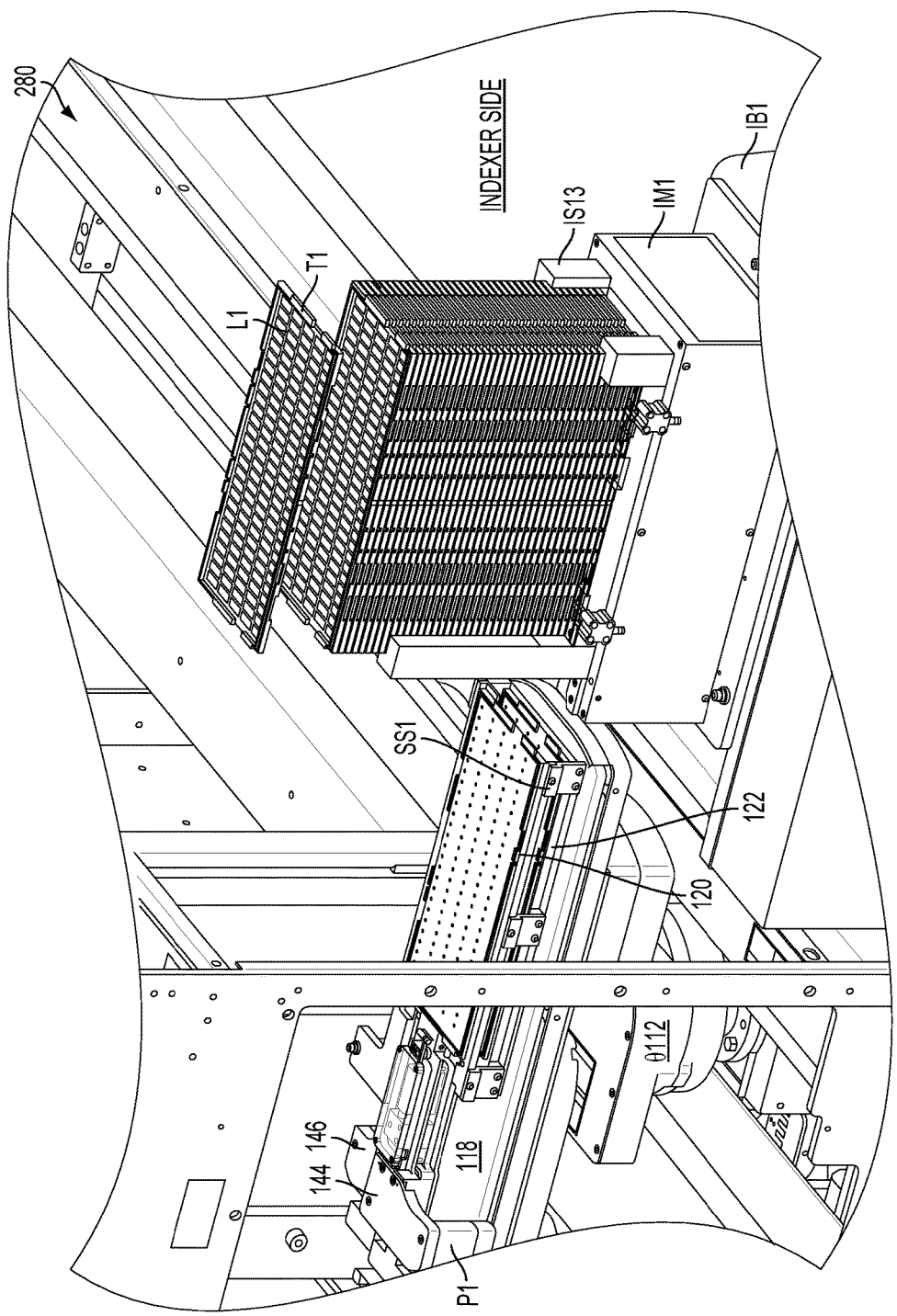
FIG. 7G is a view of the indexer side of the EFEM to illustrate a transfer of trays between the EFEM and the indexer, in accordance with several embodiments described in the present disclosure.

FIG. 7G is a side isometric view of an embodiment of a portion 280 of the indexer side to illustrate use of the reader 242 between the EFEM 156 (FIG. 4A) and the indexer 104 and to illustrate a position of the driving plates 144 and 146 before loading a tray into the indexer 104.

Figure 7H:
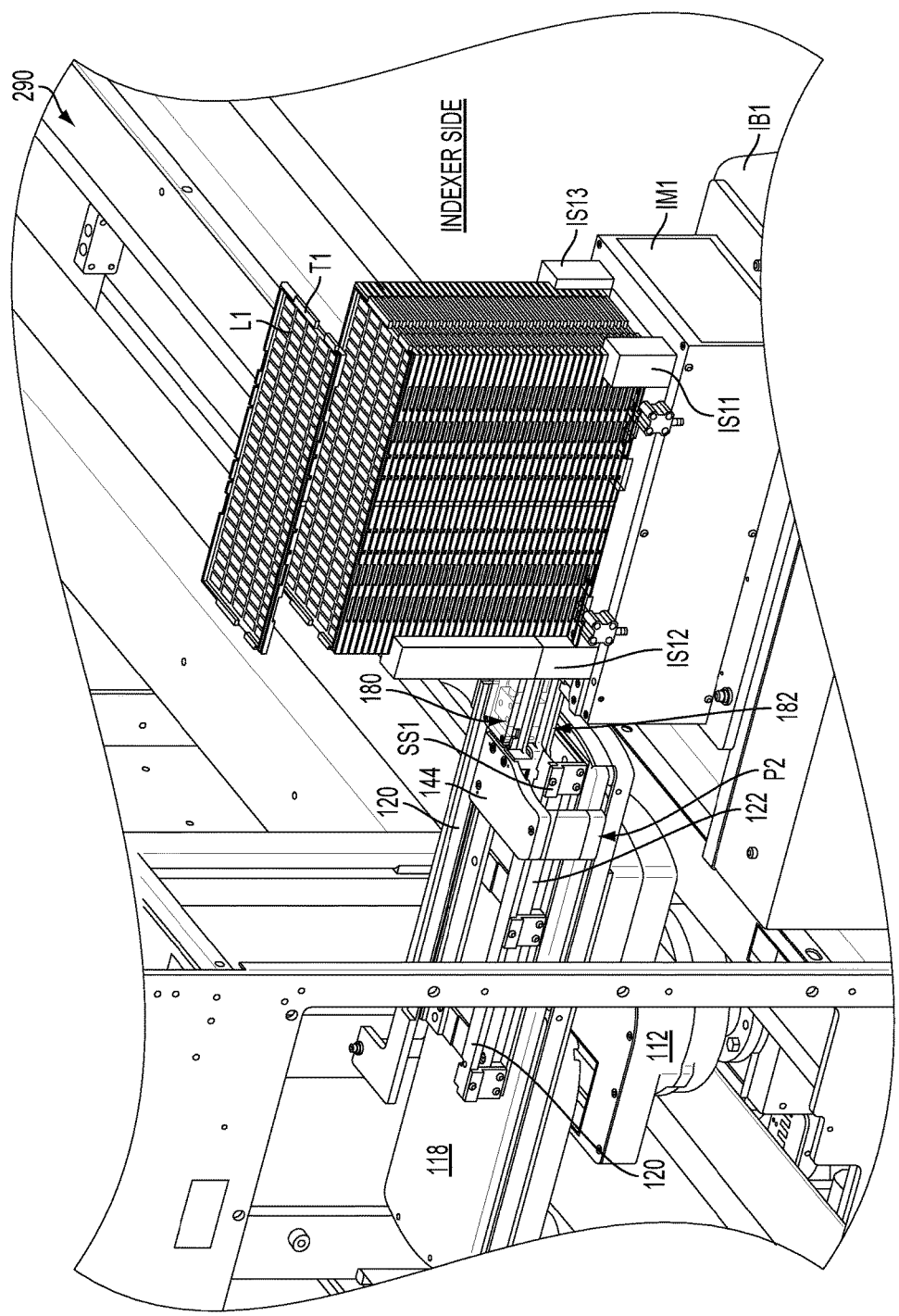
FIG. 7H is a view of the indexer side of the EFEM to illustrate a transfer of trays between the EFEM and the indexer, in accordance with various embodiments described in the present disclosure.

FIG. 7H is a side isometric view of an embodiment of a portion 290 of the indexer side to illustrate use of the reader 242 between the EFEM 156 (FIG. 4A) and the indexer 104 and to illustrate a position of the driving plates 144 and 146 during loading a tray into the indexer 104 or unloading a tray from the indexer 104.

FIG. 8A is a top view of an embodiment of a grip assembly 300 when the grip assembly 300 is about to grip a tray or has released a tray. The grip assembly 300 is used for gripping a tray and transferring the tray between the cassette 102 (FIG. 1A) and the indexer 104 (FIG. 1A). The grip assembly 300 is an example of the grip assembly 180 or the grip assembly 182 (FIG. 5A).

The grip assembly 300 is attached to a driving plate 302 via fasteners F1 and F2. The driving plate 302 is an example of the top driving plate 144 or the bottom driving plate 146 (FIG. 5A). In some embodiments, another other number of fasteners are used to attach the grip assembly 300 to the driving plate 302.

The grip assembly 300 includes grip body 304, a portion of which is covered by a cover 306. For example, the cover 306 is attached to the portion via one or more screws, e.g., screws SC1, SC2, SC3, and SC4. The grip body 304 is attached to the driving plate 302 via the fasteners F1 and F2.

In some embodiments, the portion of the grip body 304 is not covered by any cover.

The cover 306 covers a piston mechanism 308, which is attached to the grip body 304. The piston mechanism 308 includes a piston housing 310 and a piston 312 that slides in and out of the piston housing 310 to move along a length "le" of the grip body 304.

The piston 312 is attached to a twist connector 314, which is connected to an arm 316. The twist connector 314 is rotatably attached to the grip body 304 via a pivot mechanism 317 and rotates with respect to the grip body 304 via the pivot mechanism 317. For example, the pivot mechanism 317 pivots with respect to the grip body 304 to rotate the twist connector 314 with respect to the grip body 304.

The arm 316 is connected via multiple pivot mechanisms and a clamp to a grip clamp located within a grip mouth of the grip assembly 300. The pivot mechanisms, the clamp, the grip clamp, and the grip mouth are described below. The arm 316, the pivot mechanisms, the clamp, the grip clamp, and a portion of the grip body 304 including the grip mouth form a grip mechanism 318.

When the twist connector 314 is in a position Pos1, the grip clamp has released or is about to grip a tray.

A fiber cable 320 is used to facilitate guidance of a light, e.g., an optical beam, etc., generated by a light source and sensor within the grip assembly 300 to a space between jaws of the grip mouth of the grip mechanism 318.

The piston housing 310 is covered by the cover 306 and is connected to a block connector 319. The block connector 319 is connected via an attachment mechanism to the grip body 304.

FIG. 8B is a top view of an embodiment of the grip assembly 300 when the grip assembly 300 grips a tray. When the piston 312 extends from the piston housing 310 towards the grip mechanism 318 along the length le, the twist connector 314 pivots with respect to the grip body 304 and twists to a position POS2 from the position POS1 (FIG. 8A).

In some embodiments, when the twist connector 314 is at the position POS2, the twist connector is substantially perpendicular to the length le. In these embodiments, when the twist connector 314 is at the position POS1, the twist connector is angled and is not substantially perpendicular with respect to the length le.

The tray T1 is gripped when the twist connector 314 is at the position POS2.

FIG. 8C is a top view of an embodiment of the grip assembly 300 when the grip assembly 300 misses gripping a tray. When the piston 312 extends within the piston housing 310 away towards the grip mechanism 318 along the length le, the twist connector 314 pivots with respect to the grip body 304 and twists to a position POS3 from the position POS2 (FIG. 8B).

Similarly, the twist connector 314 changes from the position POS3 to the position POS1. For example, the piston 312 retracts within the piston housing 310 to change a position of the twist connector 314 from the position POS3 to the position POS1.

In some embodiments, when the twist connector 314 is at the position POS3, the twist connector is angled and is not substantially perpendicular with respect to the length le.

In various embodiments, the angle formed by the twist connector 314 in the position POS3 with respect to the length le may be the same as that of the angle formed when the twist connector 314 is in the position POS1 except that the angle formed in the position POS1 is opposite to the angle formed when the twist connector 314 is in the position POS3. In several embodiments, the angle formed by the twist connector 314 in the position POS3 with respect to the length le may be different from the angled formed when the twist connector 314 is in the position POS1 except that the angle formed in the position POS1 is opposite to the angle formed when the twist connector 314 is in the position POS3.

Gripping of the tray T1 is missed when the twist connector 314 is at the position POS3.

FIG. 8D-1 is a side view of an embodiment of a portion 350 of the grip assembly 300 when the twist connector 314 is at the position POS1 to grip a tray or after a recent release of the tray. When the piston 312 is extended to an extent EX1 from the piston housing 310 (FIG. 8A), the twist connector 314 is at the position POS1. The twist connector 314 is attached via the arm 316 to a pivot mechanism 352. The pivot mechanism 352 is attached to a clamp 354, which is attached to another pivot mechanism 356. Examples of a pivot mechanism include a rod, a bar, a cylinder, etc. The pivot mechanism 356 is at an opposite end of the clamp 354 compared to the pivot mechanism 352.

A grip clamp 358 is attached to the pivot mechanism 356 and extends into a grip mouth 360 of the grip body 304. In some embodiments, the grip clamp 358 is referred to herein as a gripper. The grip clamp 358 moves up and down within the grip mouth 360 with the rotation of the pivot mechanism 356. The grip mouth 360 is formed at an edge of the grip body 304.

In some embodiments, the grip mouth 360 has a C shape or a nearly C shape.

The piston 312 slides horizontally in an out of the piston housing 310 (FIG. 8A) to change positions of the twist connector 314 between POS1, POS2, and POS3. When the twist connector 314 pivots using the pivot mechanism 317, the arm 316 moves in and out, e.g., extends and retracts, etc., horizontally to rotate the pivot mechanism 356 via forward and backward movement of the clamp 354. As the pivot mechanism 356 rotates, the grip clamp 358 moves vertically up and down.

The fiber cable 320 facilitates formation of a sensor beam 362 between two opposite jaws 364 and 366 of the grip mouth 360. The sensor beam 362 is generated when the light source and sensor generates light that is guided into a beam by the fiber cable 320 towards the grip mouth 360. A tray hook H1 attached to the tray T1 is about to intercept the sensor beam 362 or has just finished intercepting the sensor beam 362 when the twist connector 314 is in the position POS1.

In various embodiments, the grip assembly 300 excludes the fiber cable 320 and the light sensor and source.

In some embodiments, when the sensor beam 362 is intercepted by an edge of a tray, e.g., by a tray hook, etc., a sensor within the grip body 304 sends a signal to an encoder and decoder within the end effector drive motor 184 (FIG. 5A). The encoder and decoder determines a horizontal location of the grip mechanism 318 at which the sensor beam 362 is intercepted and sends a stop signal to the end effector drive motor 184 (FIG. 5A). Upon receiving the stop signal, the end effector drive motor 184 stops driving the grip assembly 300 via the driving plates 144 and 146 (FIG. 5A). The stopping facilitates engagement of the tray hook H1 with the grip clamp 358.

In some embodiments, the end effector drive motor 184 moves the grip assembly 300 at a faster speed until the sensor beam 362 is intercepted and slows and/or stops the movement after the sensor beam 362 is intercepted.

FIG. 8D-2 is another side view of an embodiment of the portion 350 of the grip assembly 300 when the twist connector 314 is at the position POS1 to grip a tray or after a recent release of the tray.

FIG. 8D-3 is a side view of an embodiment of the portion 350 of the grip assembly 300 when the twist connector 314 is at the position POS2 and has gripped the tray T1. When the piston 312 has extended to an extent EX2 from the piston housing 310 (FIG. 3A), the twist connector 314 is at the position POS2. In some embodiments, the extent EX2 is greater than the extent EX1 (FIG. 8D-2).

When the twist connector 314 is at the position POS2, the grip clamp 358 grips, e.g., forms a hook connection, etc., with the tray hook H1 to engage the tray T1. As the twist connector 314 moves horizontally from the position POS1 to the position POS2, the grip clamp 358 moves vertically up to grip the tray hook H1. Also, the sensor beam 362 is intercepted by the tray hook H1. When the sensor beam 362 is intercepted by the tray hook H1, the sensor within the grip assembly 300 (FIG. 8A) senses that a tray is about to be gripped.

In some embodiments, the piston 312 retracts from the extent EX2 to the extend EX1 (FIG. 8D-1) to release a tray from the grip of the grip clamp 358.

After the tray hook H1 engages with the grip clamp 358, the end effector drive motor 184 operates to drive the plates 144 and 146 (FIG. 5A) by driving the top slider block 176 and the bottom slider block along the slide base 188 (FIG. 5A) to retract the grip assembly 300 towards the slides 120 and 122. The tray T1 slides from the cassette 102 or the indexer 104 to the upper slide 120 or to the lower slide 122 as the plates 144 and 146 slide from the position P2 (FIG. 5B) to the position P1 (FIG. 5A).

Similarly, as the piston 312 retracts from the extent EX2 to the extent EX1 (FIG. 8D-1), the twist connector 314 pivots with respect to the pivot mechanism 317 from the position POS2 to the position POS1. As the twist connector 314 pivots from the position POS2 to the position POS1, the grip clamp 358 moves vertically down to release the tray hook H1 to release the tray T1.

Figures 4, 8D:
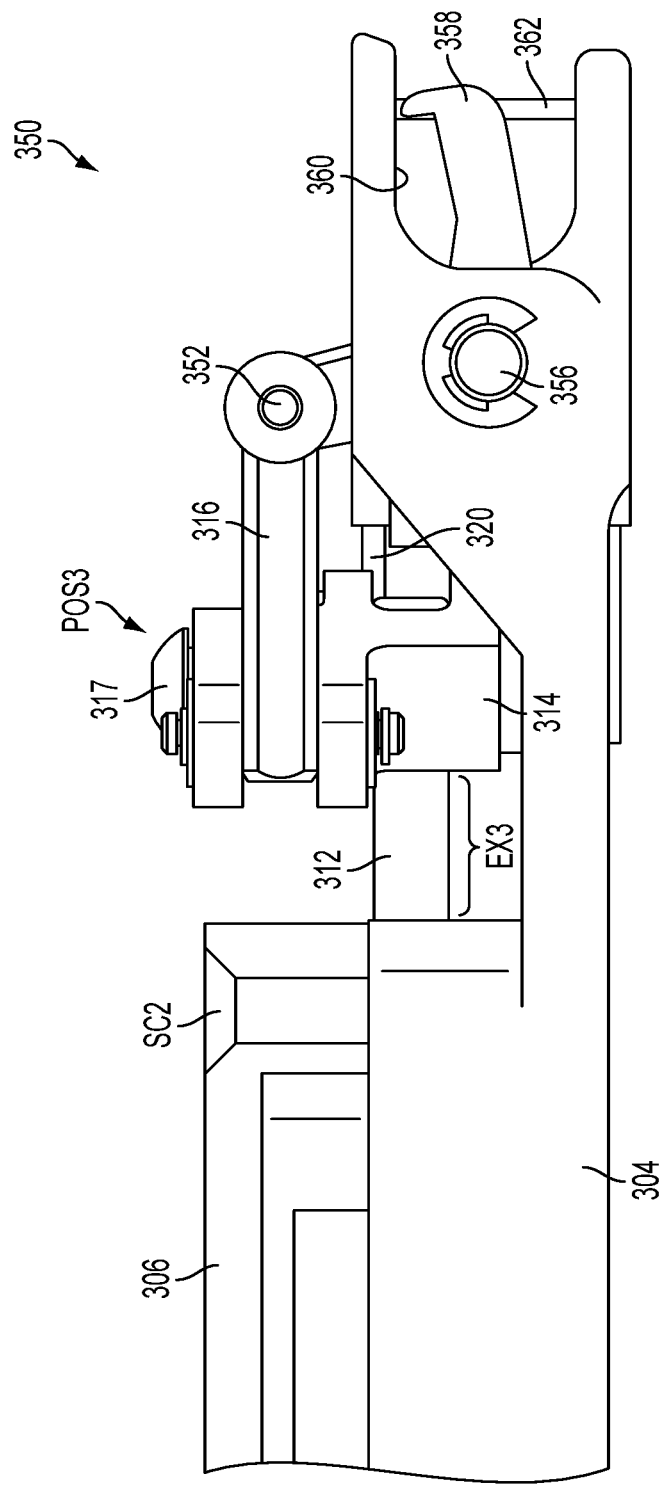

FIG. 8D-4 is a side view of an embodiment of the portion 350 of the grip assembly 300 when the twist connector 314 is at the position POS3 and has missed gripping a tray. When the piston 312 has extended to an extent EX3 from the piston housing 310 (FIG. 3A), the twist connector 314 is at the position POS3. In some embodiments, the extent EX3 is greater than the extent EX2 (FIG. 8D-3).

When the twist connector 314 is at the position POS3, the grip clamp 358 has missed gripping a tray hook to miss engaging a tray.

Figure 8E:
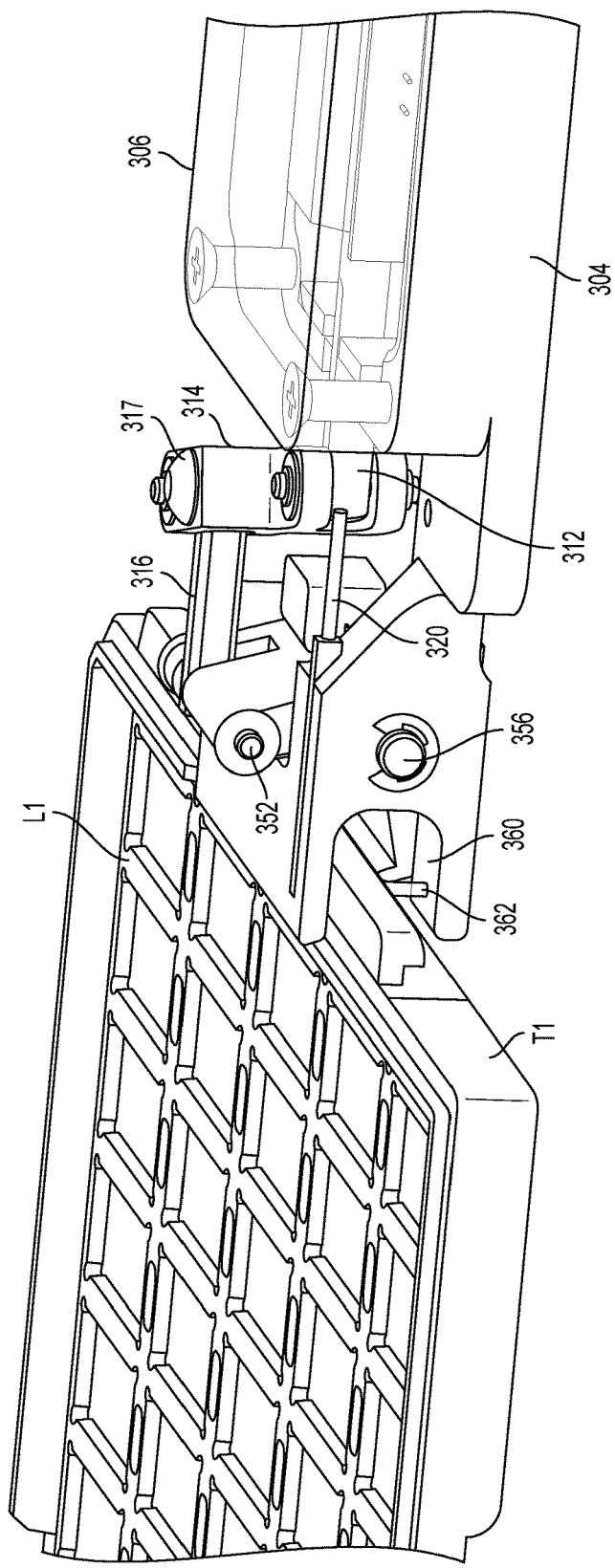
FIG. 8E is a view of the grip assembly of FIG. 8A, in accordance with various embodiments described in the present disclosure.

FIG. 8E is an isometric view of an embodiment of the portion 350 when the twist connector 314 is at the position POS1 and the grip assembly 300 is about to or has just released the tray T1.

Figure 8F:
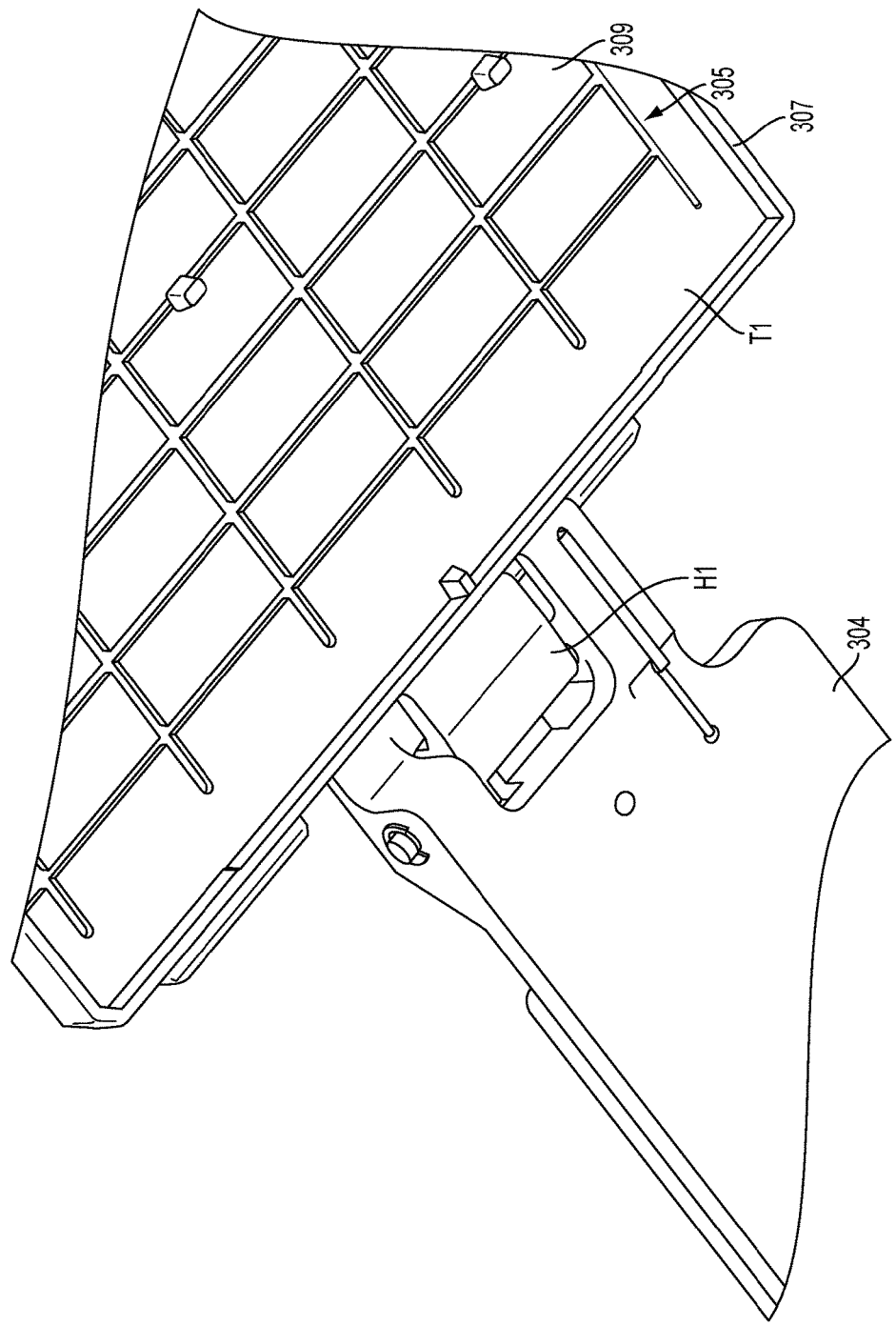
FIG. 8F is a view of the grip assembly of FIG. 8A, in accordance with several embodiments described in the present disclosure.

FIG. 8F is an isometric bottom view of an embodiment of the grip body 304 when the grip assembly 300 has gripped the tray T1 via the tray hook H1. As shown, the tray T1 has a slot 305 that extends from an edge 307 of the tray T1 to a bottom surface 309 of the tray T1 in a vertical direction.

Figure 8G:
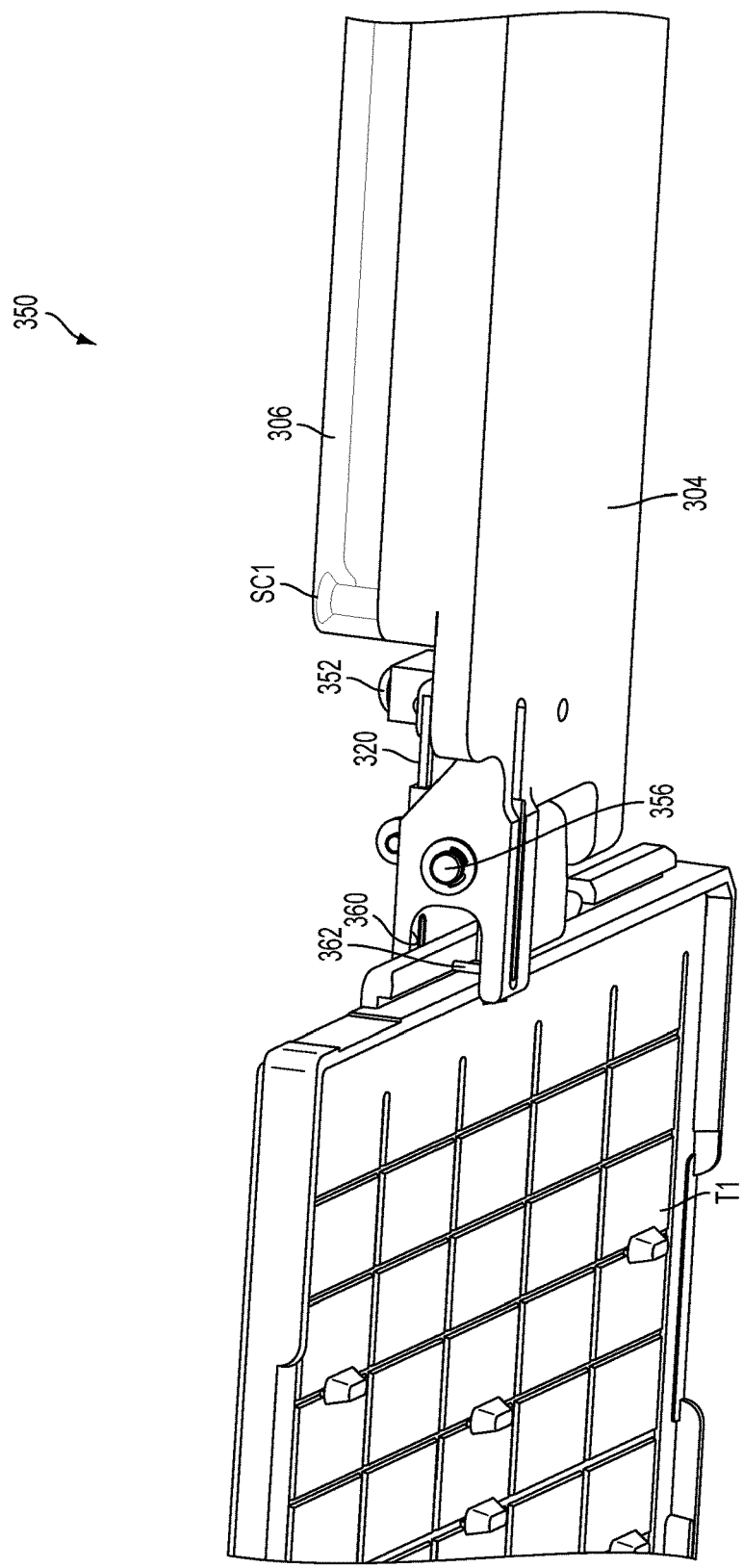
FIG. 8G is a view of the grip assembly of FIG. 8A, in accordance with several embodiments described in the present disclosure.

FIG. 8G is an isometric view of an embodiment of the portion 350 that has gripped the tray T1.

FIG. 8H is another isometric view of an embodiment of the portion 350 that is about to grip the tray T1 or has just released the tray T1.

Figure 9A:
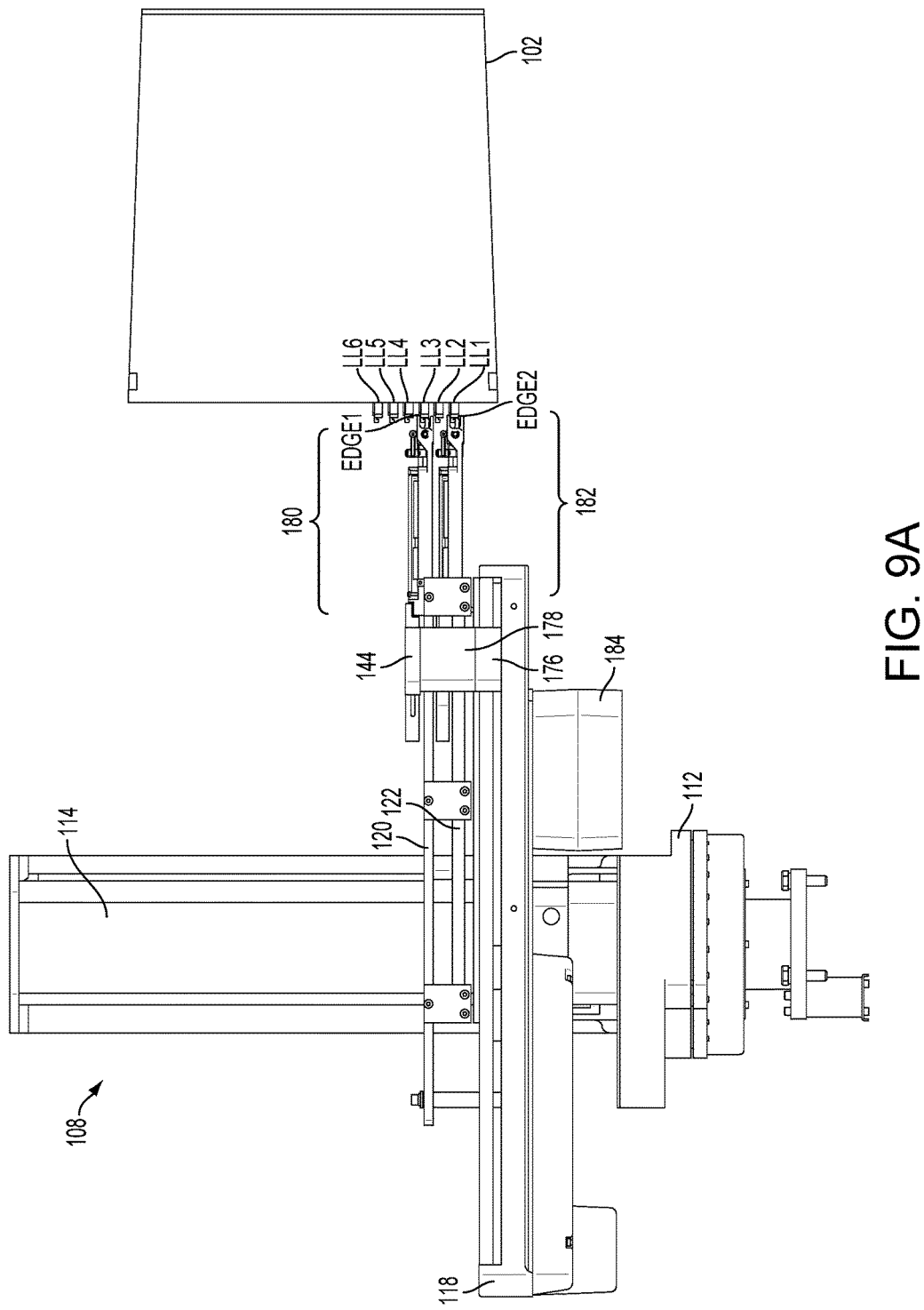
FIG. 9A is a view to illustrate a transfer of trays between the grip assembly of FIGS. 8A-8H and a storage device, in accordance with some embodiments described in the present disclosure.

FIG. 9A is a side view of an embodiment of the tray engine 108 that includes two grip assemblies 300 as examples of the upper and lower grip assemblies 180 and 182. The grip assemblies 180 and 182 have gripped trays. As shown, the trays are gripped at alternate levels within the cassette 102. For example, a tray is gripped at a level LL1 by the lower grip assembly 182 and another tray is gripped at a level LL3 by the upper grip assembly 182. A level LL2 lies between the levels LL1 and LL3.

Also, when the trays are gripped, the vertical column 114 is rotated by the theta motor 112 to facilitate edges 1 and 2 of the grip assemblies 180 and 182 to face the cassette 102.

Figure 9B:
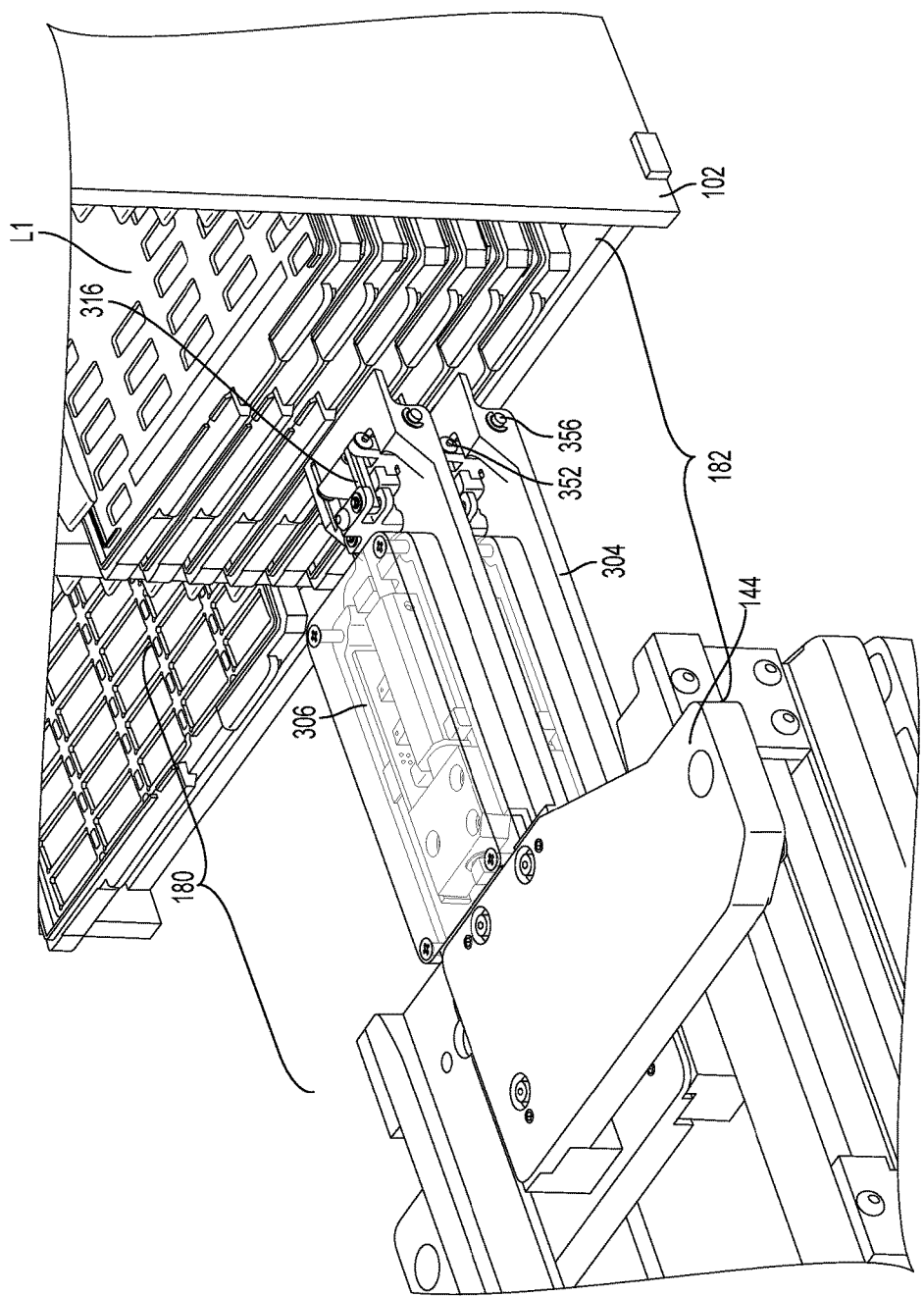
FIG. 9B is a view to illustrate a transfer of trays between the grip assembly of FIGS. 8A-8H and the storage device, in accordance with various embodiments described in the present disclosure.

FIG. 9B is an isometric view of an embodiment of the grip assemblies 180 and 182 in a gripping position of gripping trays from the cassette 102.

Figure 9C:
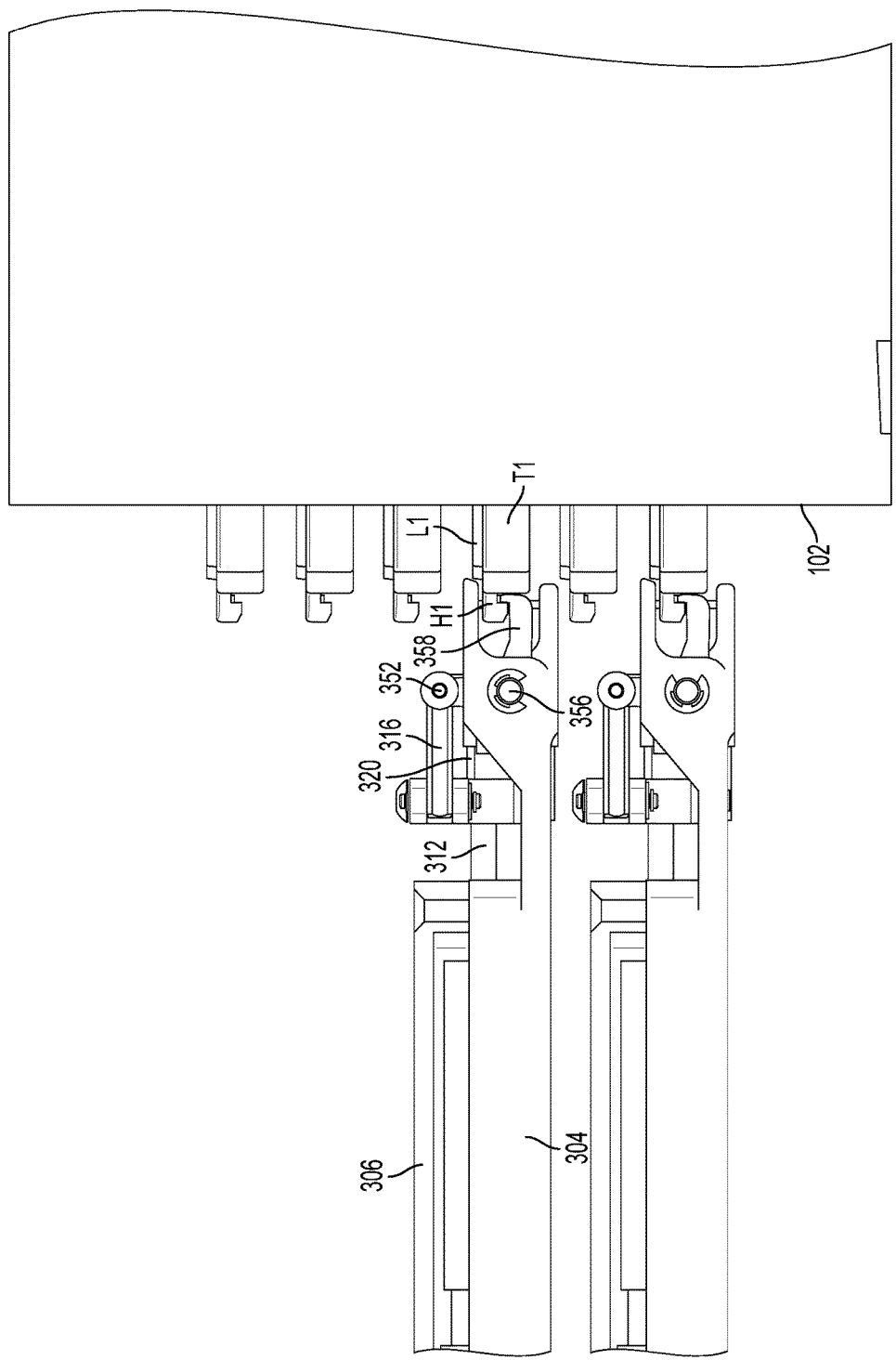
FIG. 9C is a view to illustrate a transfer of trays between the grip assembly of FIGS. 8A-8H and the storage device, in accordance with several embodiments described in the present disclosure.

FIG. 9C is a side view of an embodiment of portions of the grip assemblies 180 and 182 to illustrate gripping trays from the cassette 102.

Figure 9D:
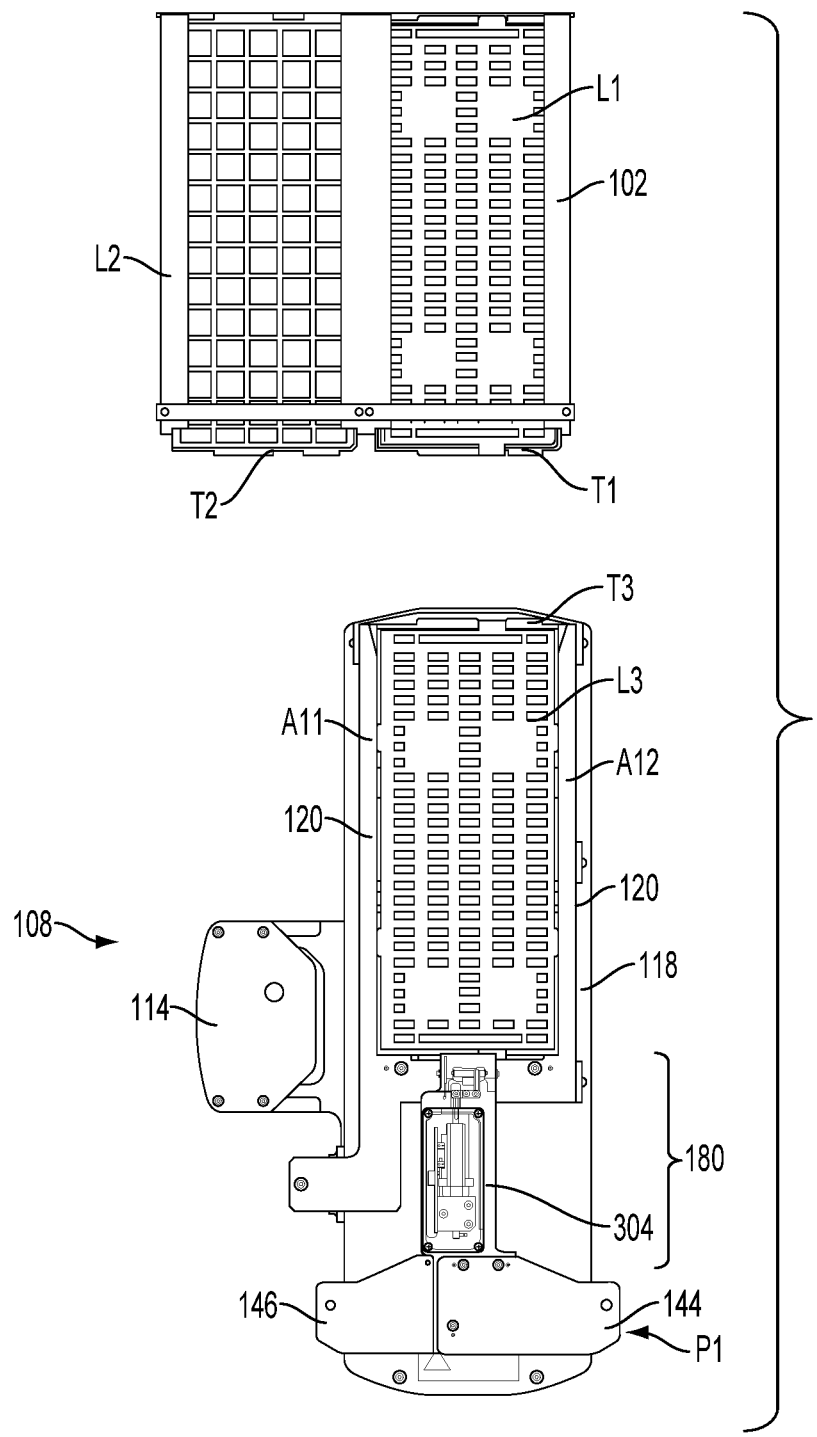
FIG. 9D is a view to illustrate a transfer of trays between the grip assembly of FIGS. 8A-8H and the storage device, in accordance with various embodiments described in the present disclosure.

FIG. 9D is a top view of an embodiment of the tray engine 108 to illustrate the retracted position P1 of the driving plates 144 and 146. The driving plates are in the retracted position P1 before gripping a tray from the cassette 102 or after gripping the tray T3 from the cassette 102.

Figure 9E:
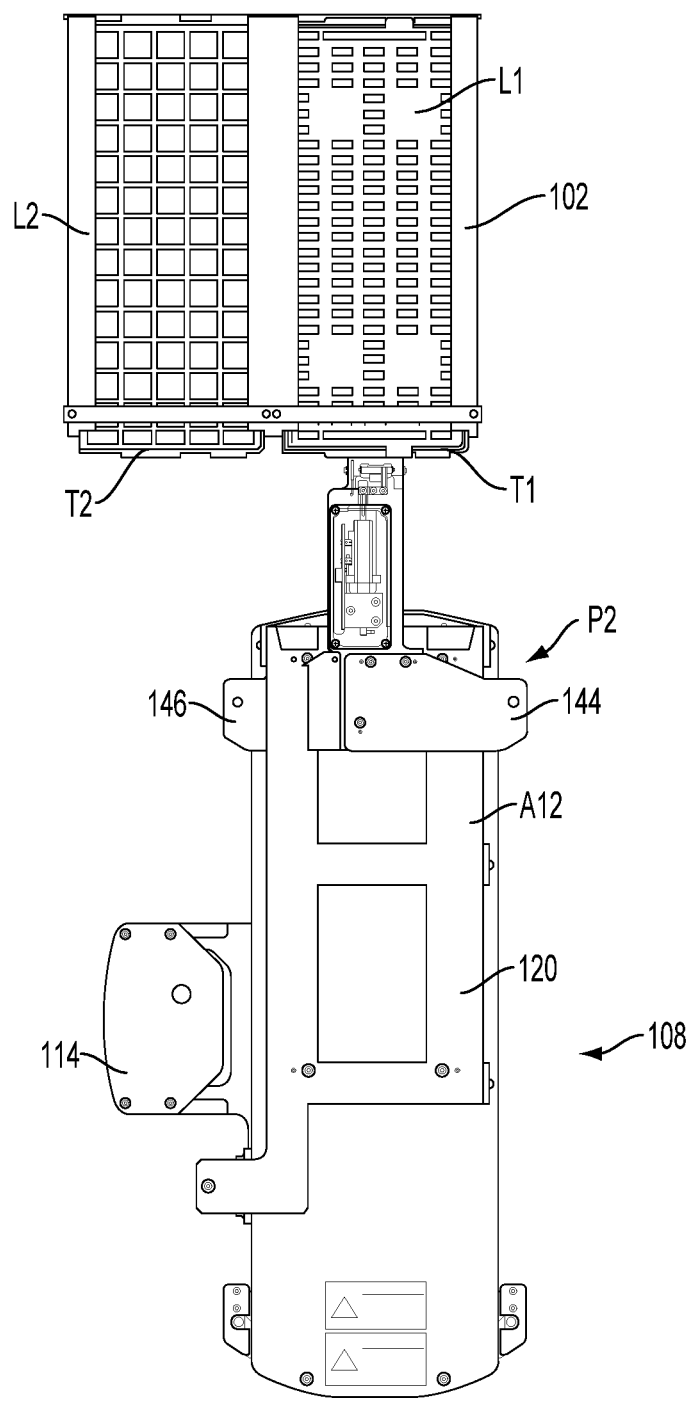
FIG. 9E is a view to illustrate a transfer of trays between the grip assembly of FIGS. 8A-8H and the storage device, in accordance with some embodiments described in the present disclosure.

FIG. 9E is a top view of an embodiment of the tray engine 108 to illustrate the extended position P2 of the driving plates 144 and 146. The driving plates are in the extended position P2 during gripping of the tray T1 from the cassette 102.

Figure 9F:
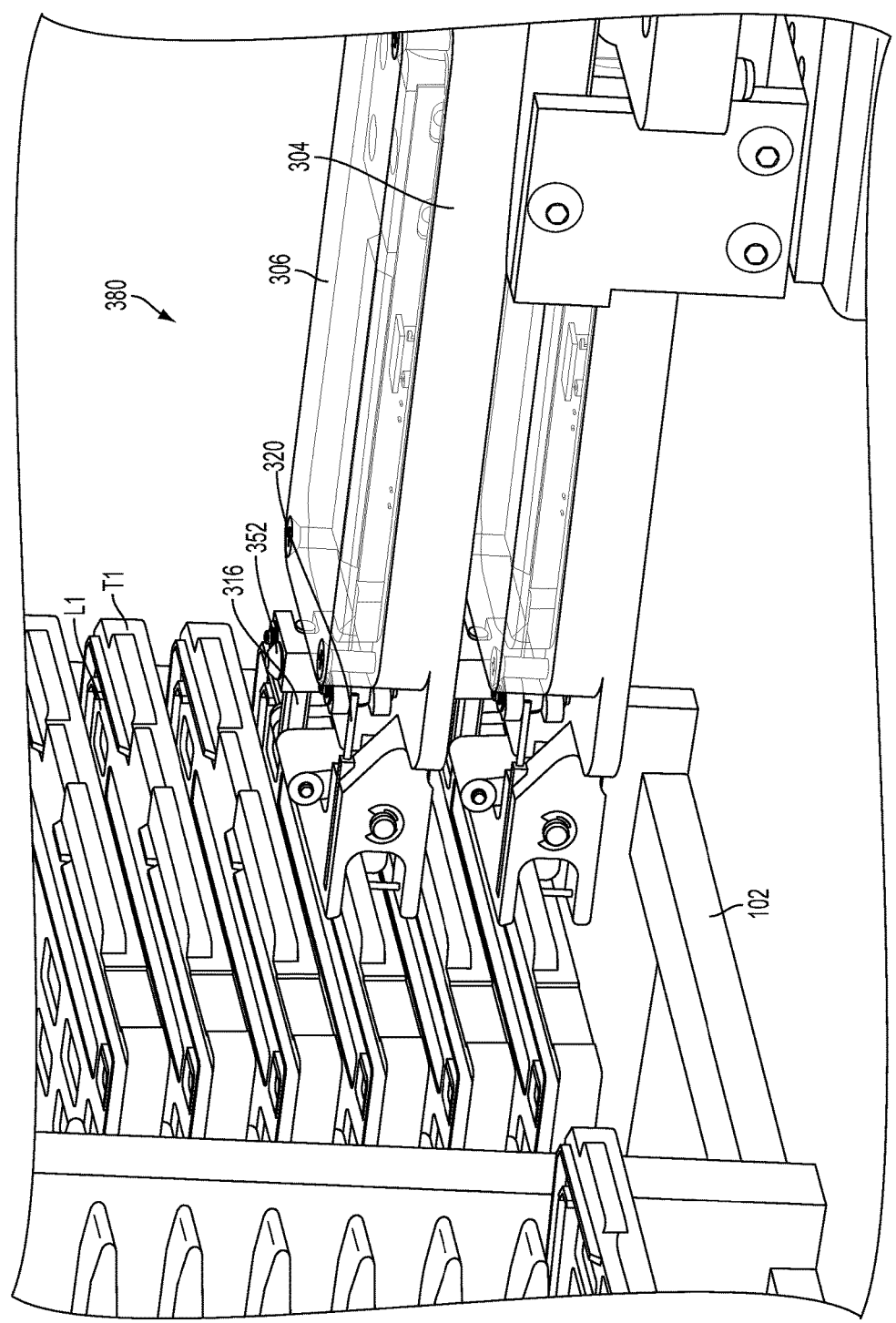
FIG. 9F is a view to illustrate a transfer of trays between the grip assembly of FIGS. 8A-8H and the storage device, in accordance with several embodiments described in the present disclosure.

FIG. 9F is an isometric view of an embodiment of a portion of the grip assembly 300 (FIG. 8A).

In various embodiments, the grip assembly 300 includes sensors to determine whether a tray is gripped or released.

Figure 10A:
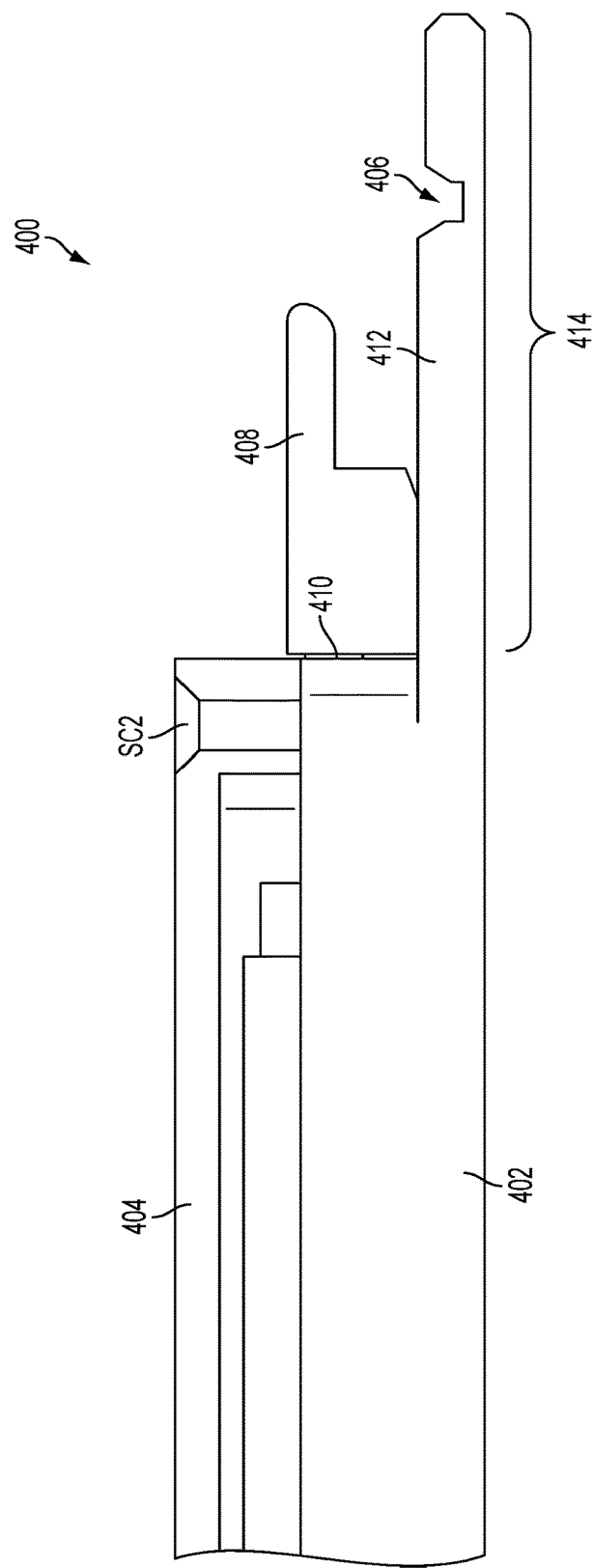
FIG. 10A is a view of a grip assembly that is a part of an end effector located within the sorter, in accordance with various embodiments described in the present disclosure.

FIG. 10A is a side view of an embodiment of a grip assembly 400 that is used to grip a tray. The grip assembly 400 is an example of the grip assembly 180 or the grip assembly 182 (FIG. 5A).

In some embodiments, the grip assembly 400 is used to retrieve a tray from the cassette 102 (FIG. 1A) or the indexer 104 (FIG. 1A) to the slides 120 and 122 (FIG. 1A). In various embodiments, the grip assembly 400 is used to slide trays from the slides 120 and 122 to the cassette 102 or the indexer 104.

The grip assembly 400 includes a grip body 402 that is attached to the driving plate 302 via the fasteners F1 and F2 (see FIG. 10E).

A cover 404 is attached to a portion via an attachment mechanism, e.g., screws SC1, SC2, SC3, and SC4, etc., of the grip body 402 to cover the portion of the grip body 402.

In some embodiments, the cover 404 is attached to the portion of the grip body 402 via any number of screws.

In various embodiments, the portion of the grip body 402 is not covered by any cover.

A portion of the grip body 402 includes a slot 406 on a top surface 412 of the grip body 402. A slide tab 408 is fitted with a piston 410 and the piston 410 slides in and out of the grip body 402 to slide on top of the surface 412.

The grip assembly 400 includes a grip mechanism 414, which includes the slide tab 406, a portion of the grip body 402 having the surface 412, and the slot 406.

Figure 10B:
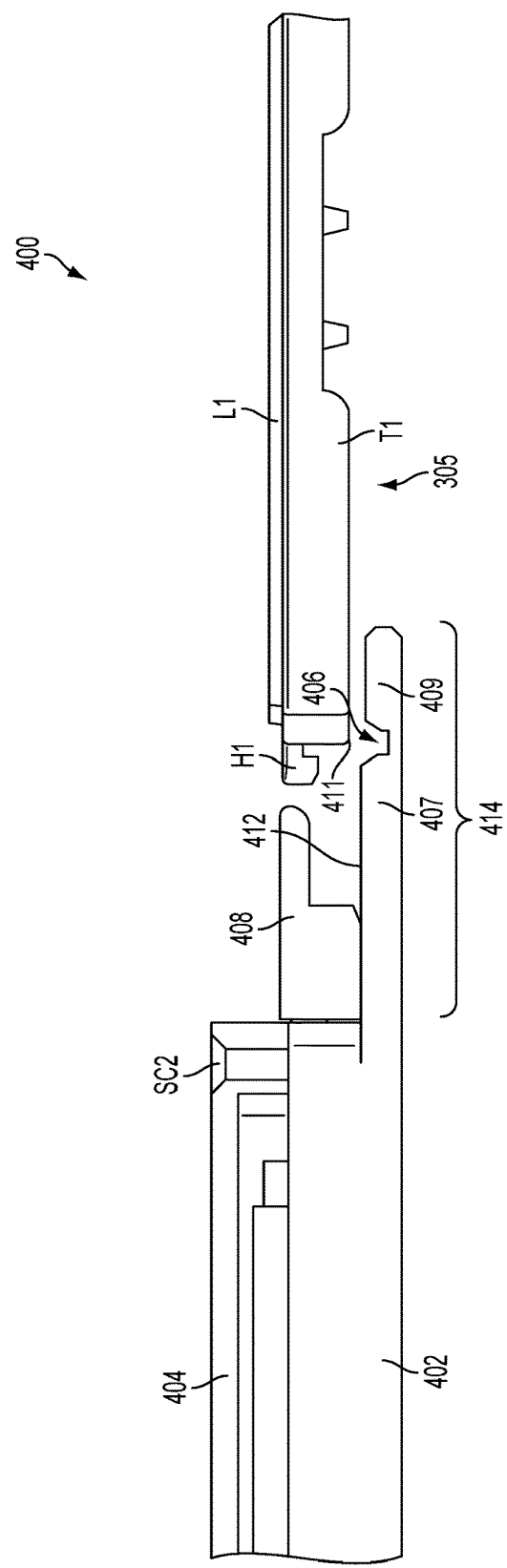
FIG. 10B is a view of the grip assembly of FIG. 10A, in accordance with some embodiments described in the present disclosure.

FIG. 10B is a side view of an embodiment of the grip assembly 400 about to grip the tray T1. As the slider block 176 (FIG. 5A) slides along the slide base 188 (FIG. 5A), the driving plate 302 (FIG. 10E) slides with the slider block 176 from the position P1 (FIG. 5A) to the position P2 (FIG. 5A). The grip assembly 400 slides with the driving plate 302 to reach the tray T1 that may be within the cassette 102 (FIG. 1A) or the indexer 104 (FIG. 1A). The tray T1 has an edge 411 that forms a border of the slot 305 (FIG. 8F) of the tray T1. The grip assembly 400 slides until the edge 411 is received within the slot 406.

The slot 406 is formed between two horizontally extended portions 407 and 409 of the grip body 402. The extended portion 407 has the top surface 412.

Figure 10C:
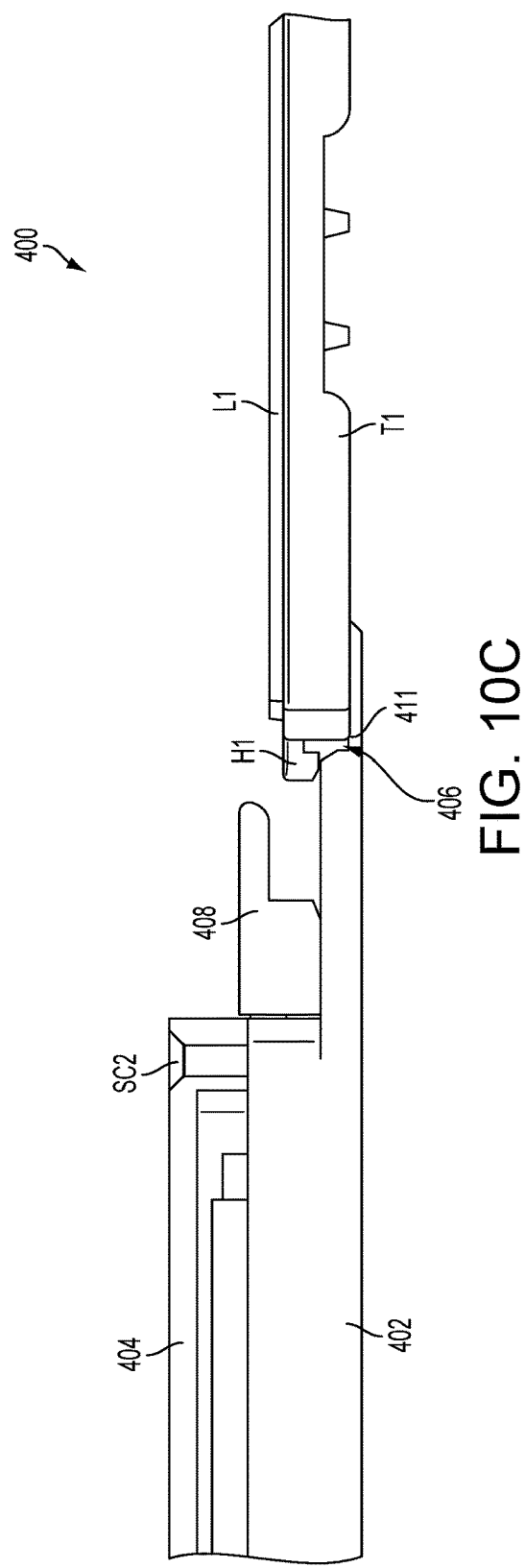
FIG. 10C is a view of the grip assembly of FIG. 10A, in accordance with various embodiments described in the present disclosure.

FIG. 10C is a side view of an embodiment of the grip assembly 400 that has gripped the tray T1. The slot 305 at the bottom surface 309 (FIG. 8F) of the tray T1 comes in contact with the extended portion 409 to engage the extended portion 409. When the extended portion 409 has engaged the slot 305 and the edge 411 of the tray T1 is received within the slot 406, the tray T1 is gripped by the grip assembly 400.

In various embodiments, the fiber cable 320 is implemented within the grip assembly 400 in a similar manner as that of the grip assembly 300 (FIG. 8A). Moreover, interception of the sensor beam 362 (FIG. 8A) is determined in a similar manner as that described above.

Also, in some embodiments, the end effector drive motor 184 (FIG. 4A) moves grip assembly 400 via the plates 144 and 146 (FIG. 5A) at a faster speed until the sensor beam 362 is intercepted and slows or stops the grip assembly 400 after the sensor beam 362 is intercepted to facilitate reception of an edge of a tray into the slot 406.

In some embodiments, the terms grip and engage are used interchangeably herein.

Figure 10D:
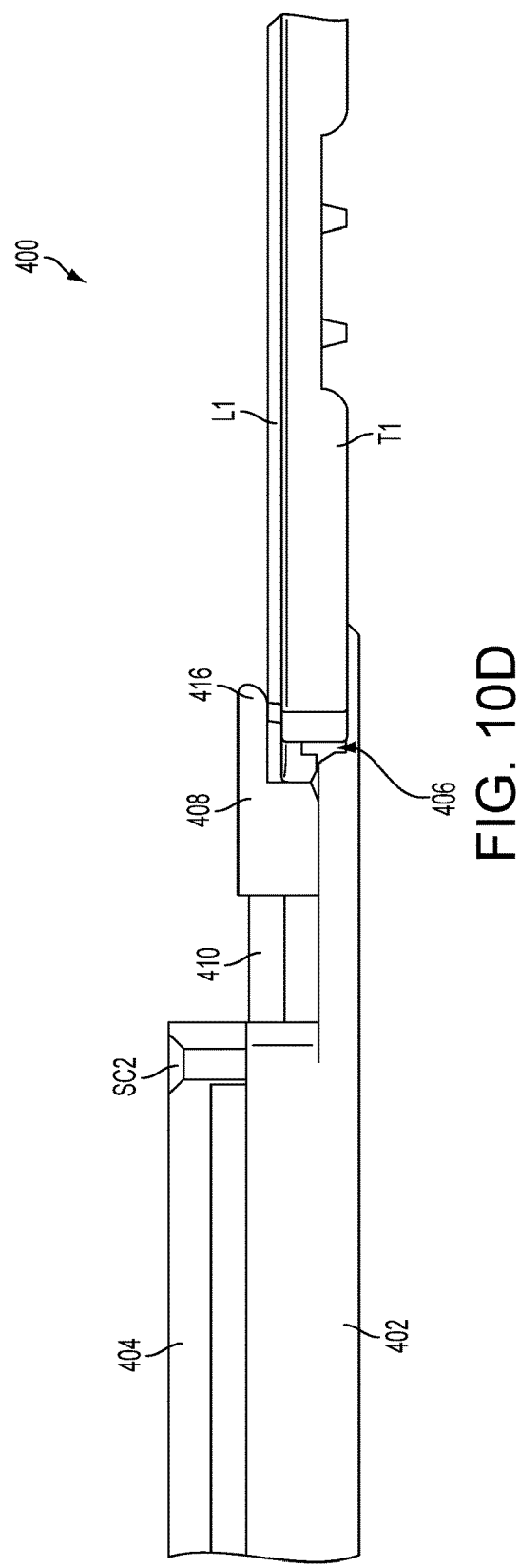
FIG. 10D is a view of the grip assembly of FIG. 10A, in accordance with several embodiments described in the present disclosure.

FIG. 10D is a side view of an embodiment of the grip assembly 400 in which the slide tab 408 extends over the tray lid L1 to lock the tray T1 with the grip body 402. The piston 410 extends from a retracted position that is shown in FIG. 10A thru 10C to an extended position along a length "len" (shown in FIG. 10E) of the grip body 402 to allow a protruding portion 416 of the slide tab 408 to contact the tray lid L1 to lock the tray T1. It should be noted that the tray T1 is engaged with the extended portion 409 when the protruding portion 416 extends over the tray lid L1 to lock the tray T1 with the grip body 402.

After the tray T1 is locked with the grip body 402, the end effector drive motor operates to drive the plates 144 and 146 (FIG. 5A) by driving the top slider block 176 and the bottom slider block along the slide base 188 (FIG. 5A) to retract the grip assembly 400 towards the slides 120 and 122 (FIG. 5A). The tray T1 slides from the cassette 102 or the indexer 104 to the upper slide 120 or to the lower slide 122 as the plates 144 and 146 slide from the position P2 (FIG. 5B) to the position P1 (FIG. 5A).

FIG. 10E is a top view of an embodiment of the grip assembly 400. The piston 410 is connected in a sliding position to a piston housing 440. The piston housing 440 is covered by the cover 404 and is connected to a block connector 442. The block connector 442 is connected via an attachment mechanism to the grip body 402. As shown, the slide tab 408 is in a retracted position.

Figure 10F:
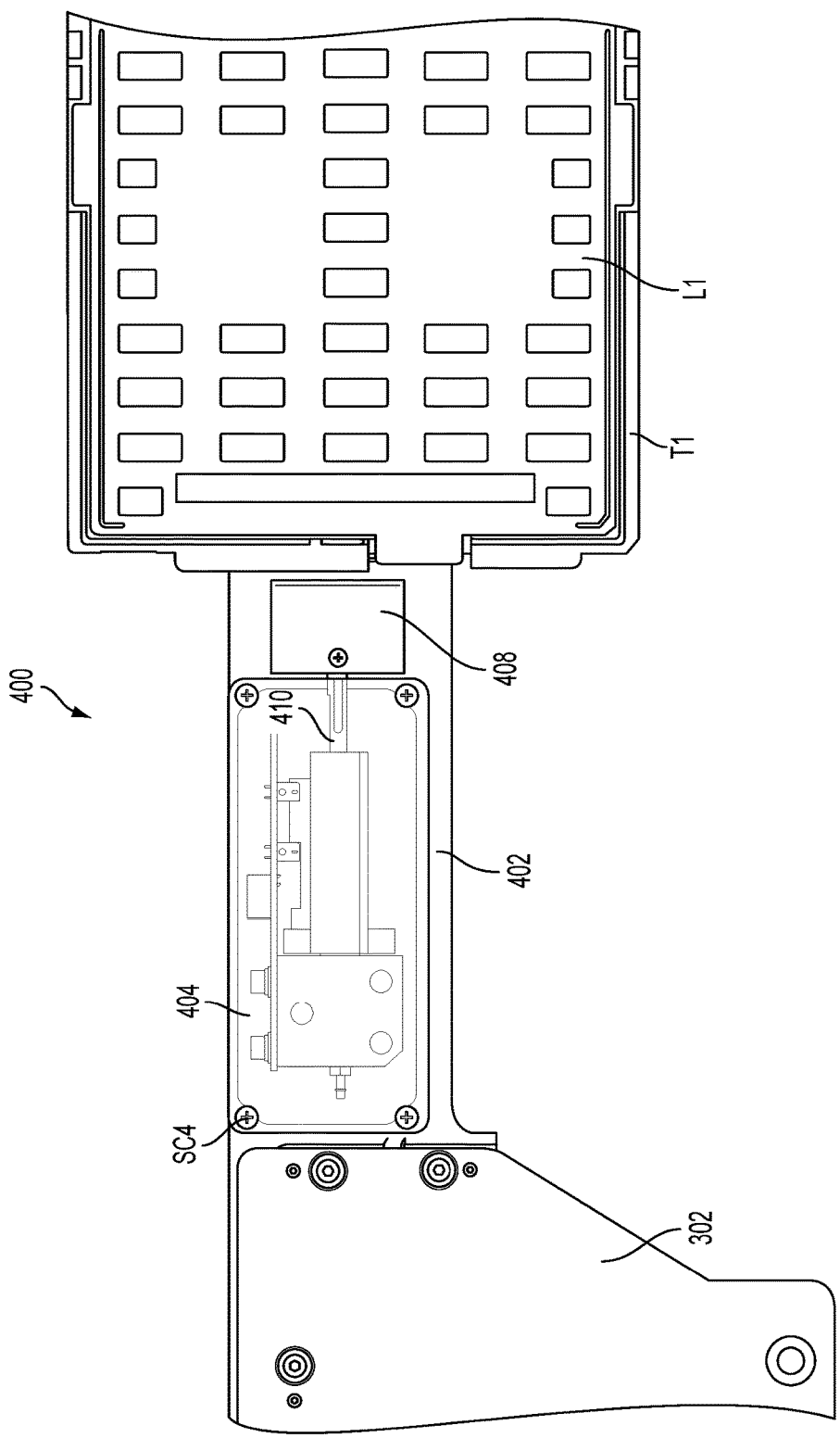
FIG. 10F is a view of the grip assembly of FIG. 10A, in accordance with several embodiments described in the present disclosure.

FIG. 10F is a top view of an embodiment of the grip assembly 400 when the extended portion 409 (FIG. 10B) of the grip body 402 has engaged the tray T1. As shown, when the extended portion 409 has engaged the tray T1, the piston 410 is in the retracted position and the slide tab 408 has not locked the tray T1.

Figure 10G:
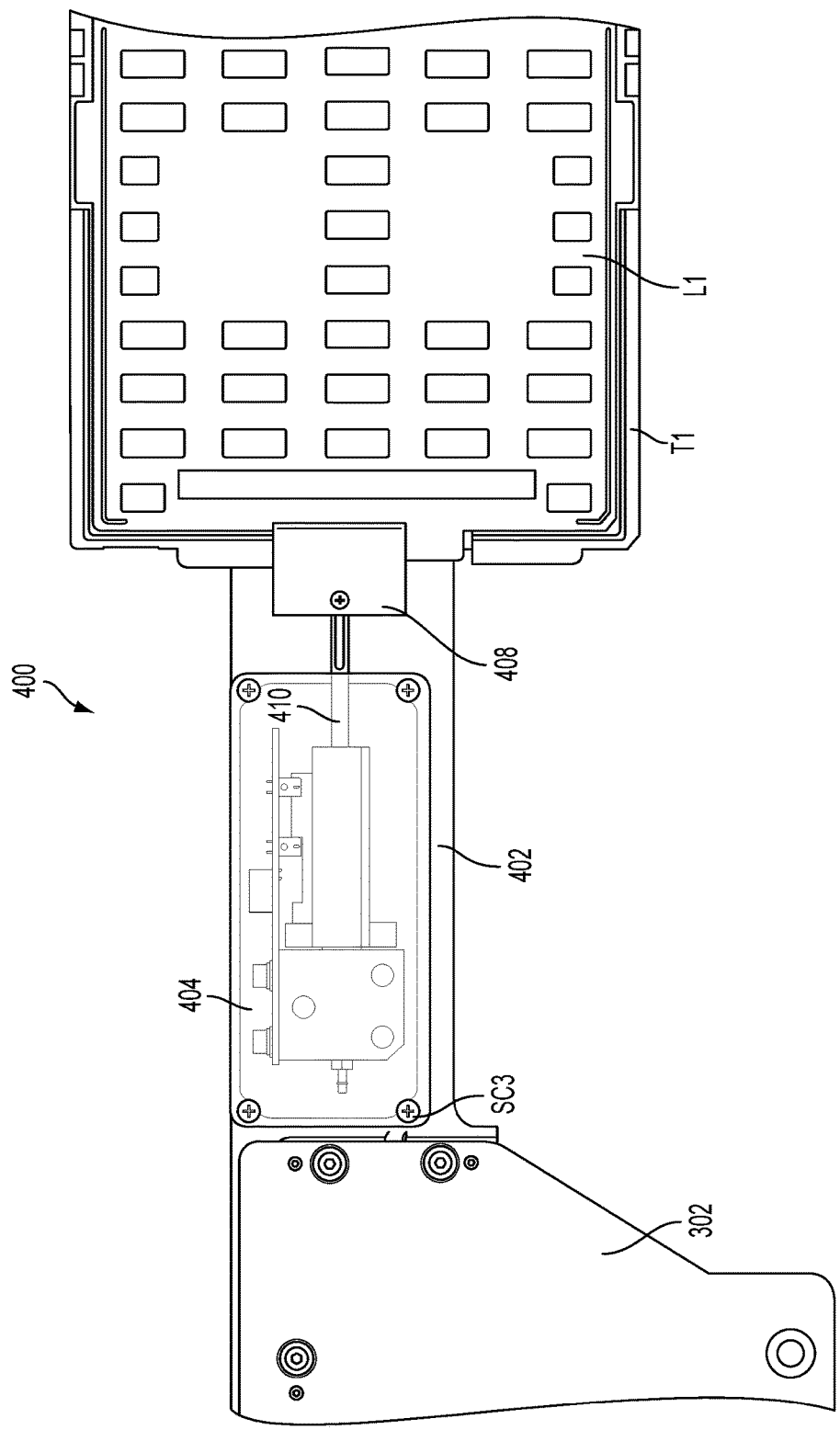
FIG. 10G is a view of the grip assembly of FIG. 10A, in accordance with various embodiments described in the present disclosure.

FIG. 10G is a top view of an embodiment of the grip assembly 400 when the extended portion 409 (FIG. 10B) of the grip body 402 has engaged the tray T1 and the slide tab 408 extends over the tray lid L1 to lock the tray T1.

Figure 11A:
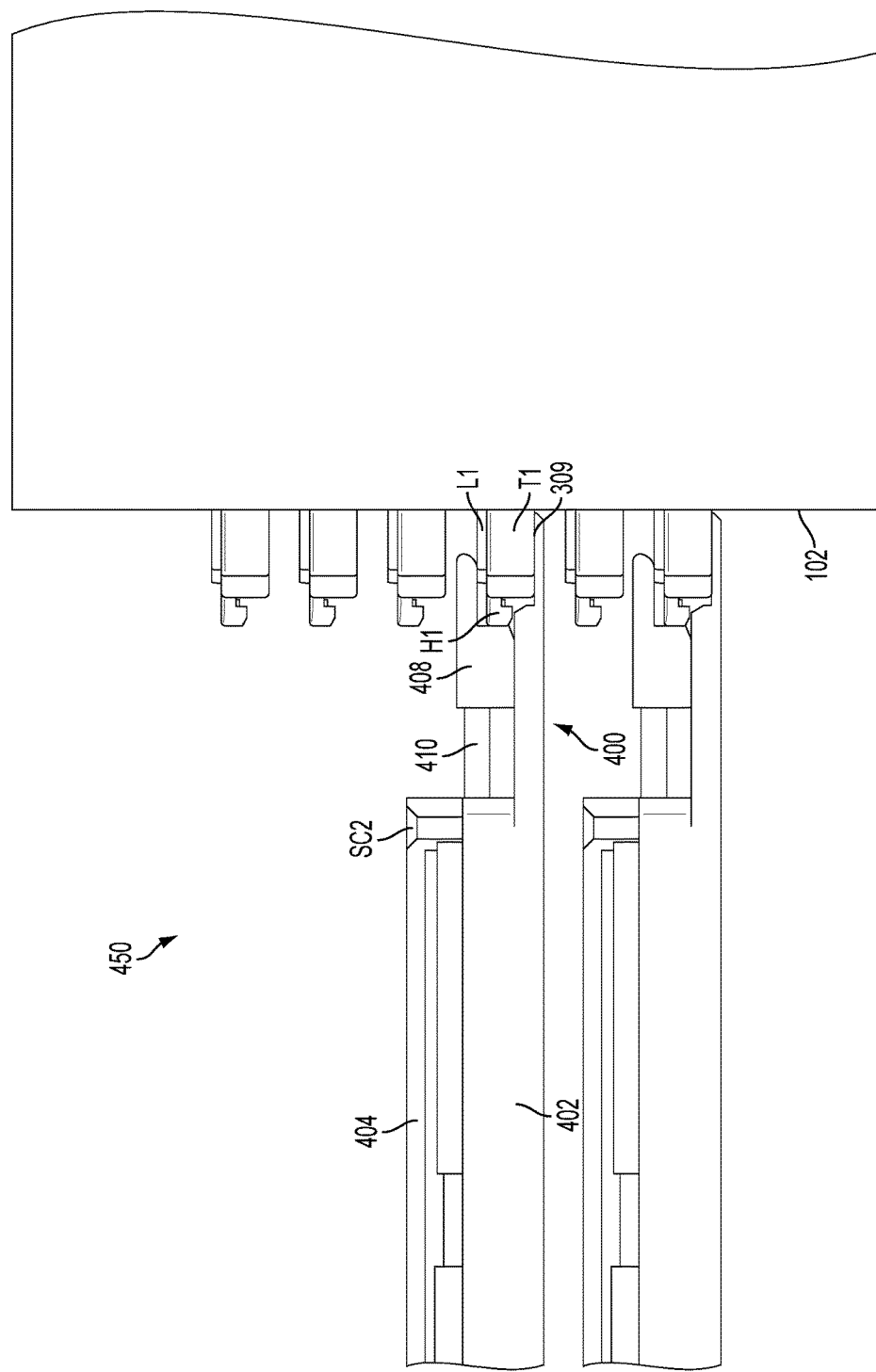
FIG. 11A is a view to illustrate a transfer of trays between the grip assembly of FIGS. 10A-10G and a storage device, in accordance with several embodiments described in the present disclosure.

FIG. 11A is a side view of an embodiment of a system 450 illustrating use of the grip assembly 400 for engaging and locking the tray T1 in the cassette 102. As shown, the bottom surface 309 of the tray T1 is in contact with the top surface 412 (FIG. 10A) of the grip body 402.

Figure 11B:
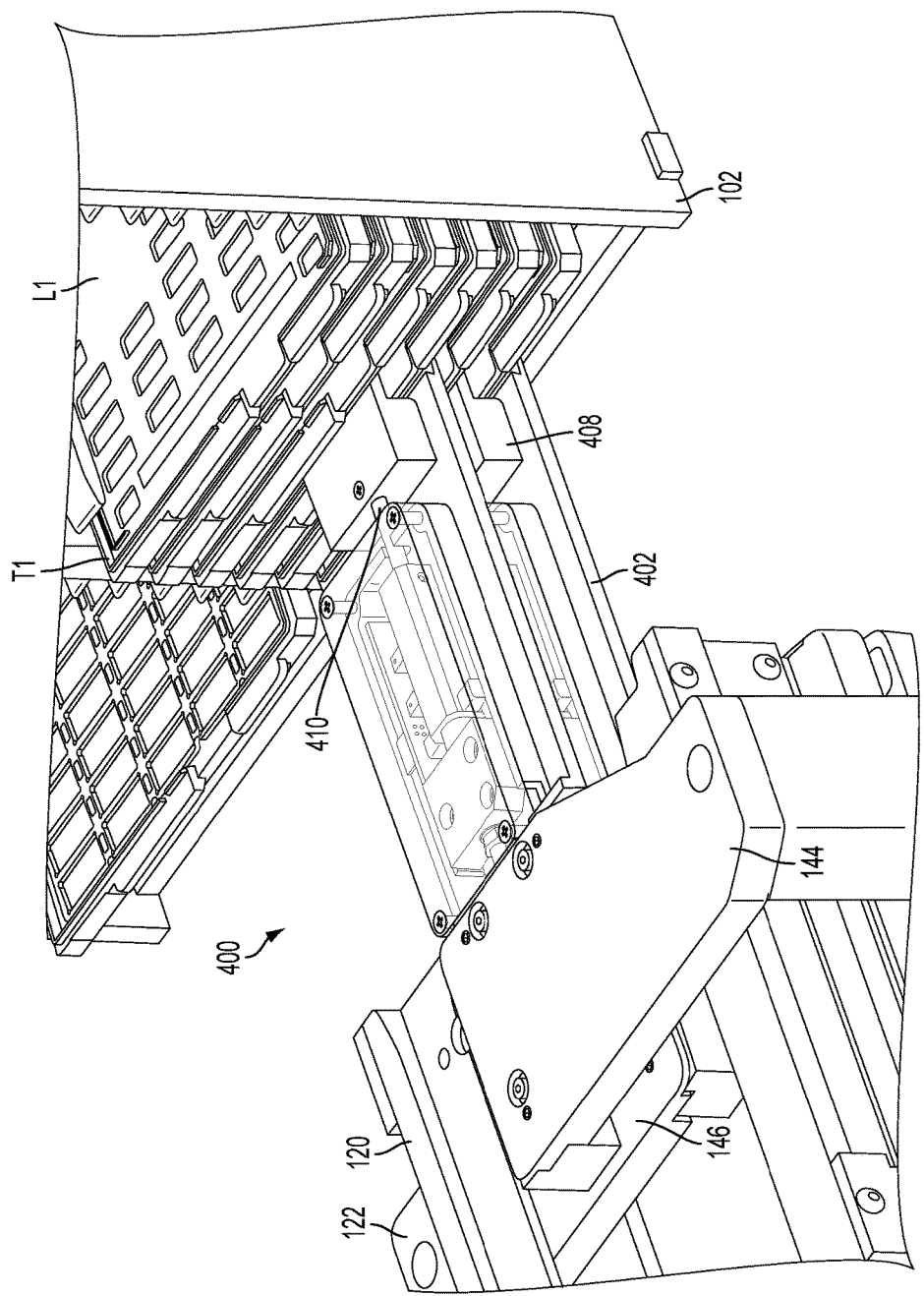
FIG. 11B is a view to illustrate a transfer of trays between the grip assembly of FIGS. 10A-10G and the storage device of FIG. 11A, in accordance with some embodiments described in the present disclosure.

FIG. 11B is an isometric view of an embodiment of the grip assembly 400 as gripping tray from the cassette 102.

Figure 11C:
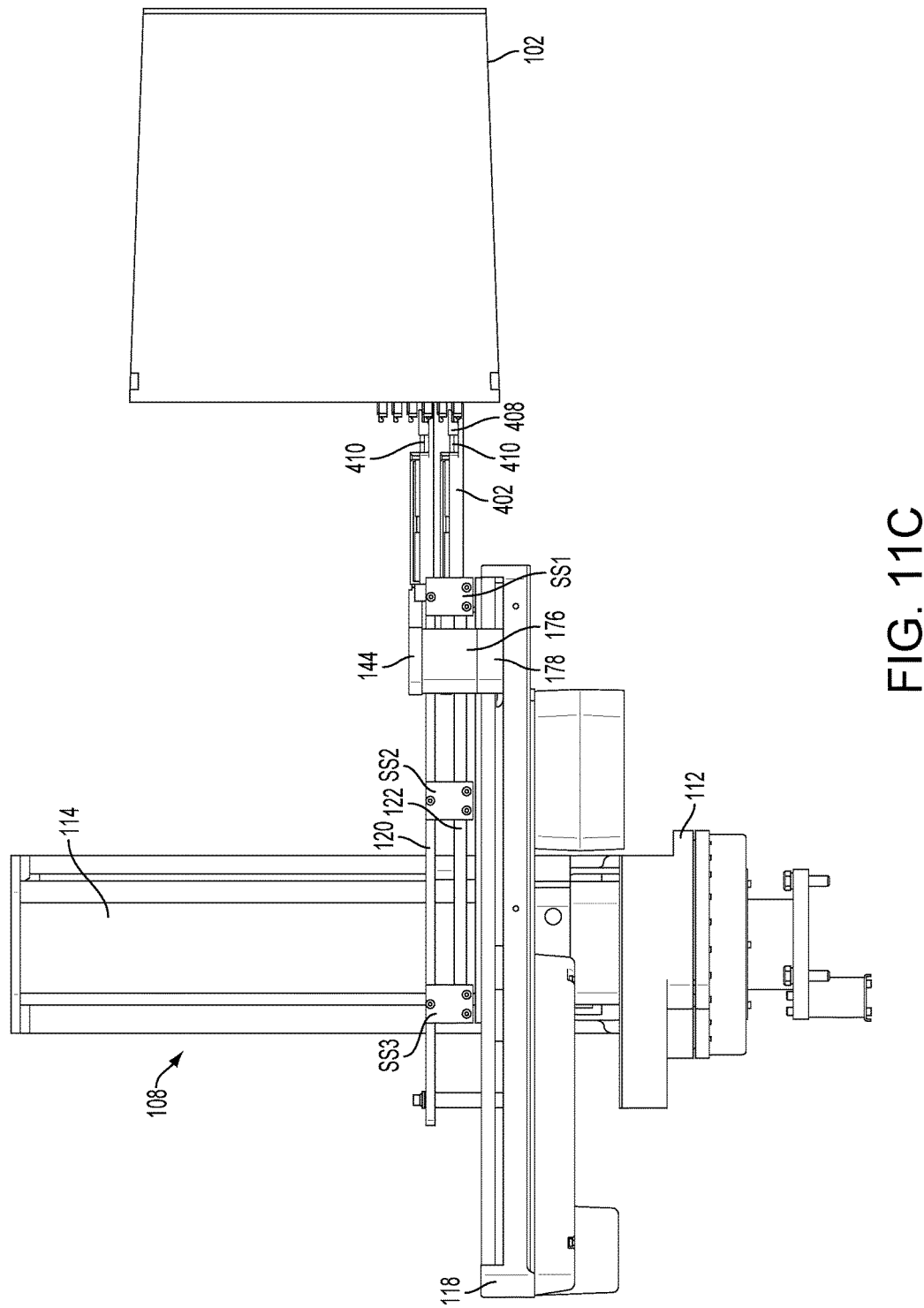
FIG. 11C is a view to illustrate a transfer of trays between the grip assembly of FIGS. 10A-10G and the storage device of FIG. 11A, in accordance with several embodiments described in the present disclosure.

FIG. 11C is a side view of an embodiment of the tray engine 108 that includes two grip assemblies 400 as examples of the upper and lower grip assemblies 180 and 182 (FIG. 5A).

In some embodiments, the grip assemblies 180 and 182 are used to grip tray lids instead of trays to remove tray lids from trays located within the cassette 102 or the indexer 104. In these embodiments, the grip assemblies 180 and 182 are used to place tray lids on trays located within the cassette 102 or the indexer 104.

Figure 11D:
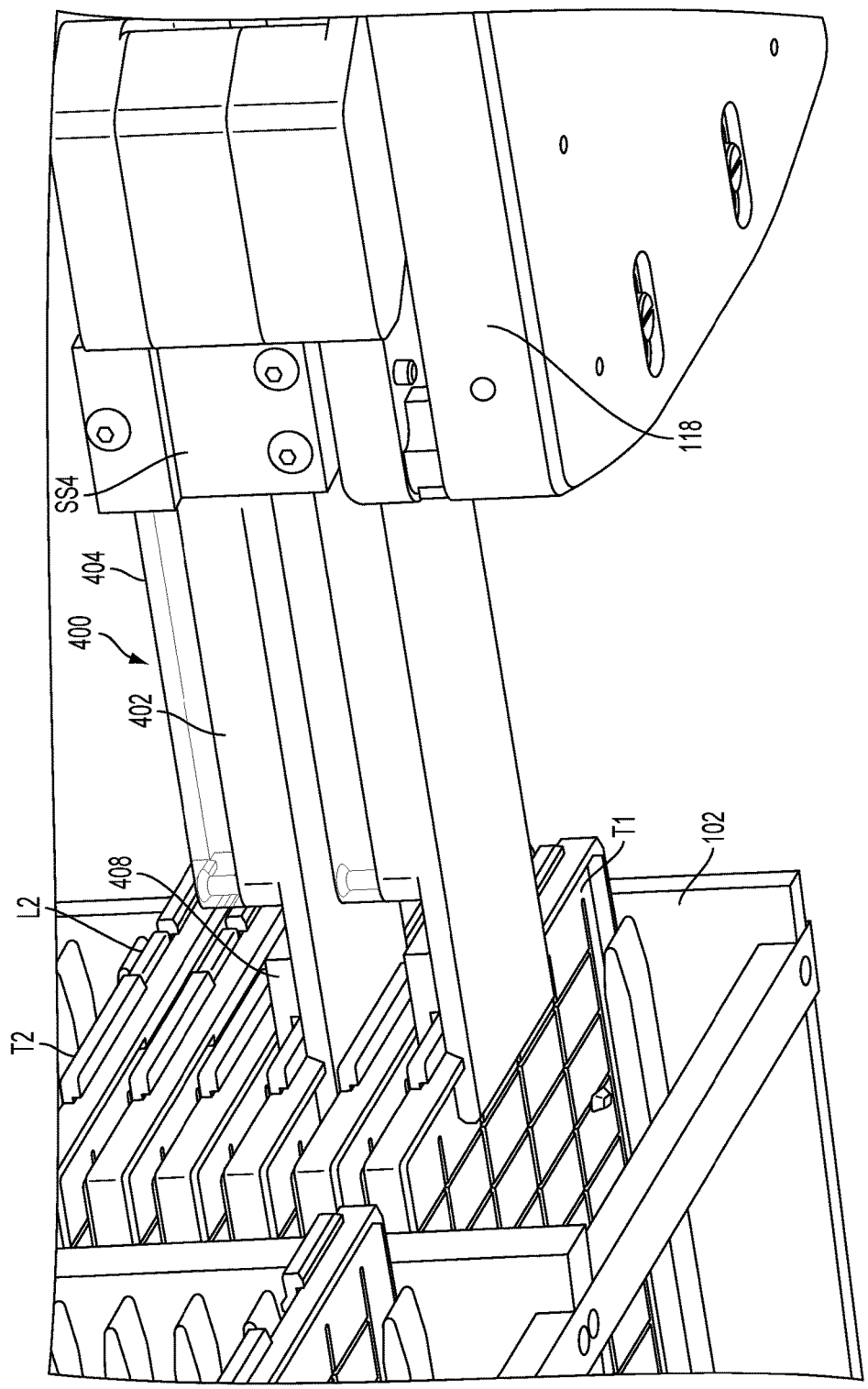
FIG. 11D is a view to illustrate a transfer of trays between the grip assembly of FIGS. 10A-10G and the storage device of FIG. 11A, in accordance with various embodiments described in the present disclosure.

FIG. 11D is an isometric view of an embodiment of the grip assembly 400.

In various embodiments, the grip assembly 400 includes sensors to determine whether a tray is gripped or released.

Figure 12:
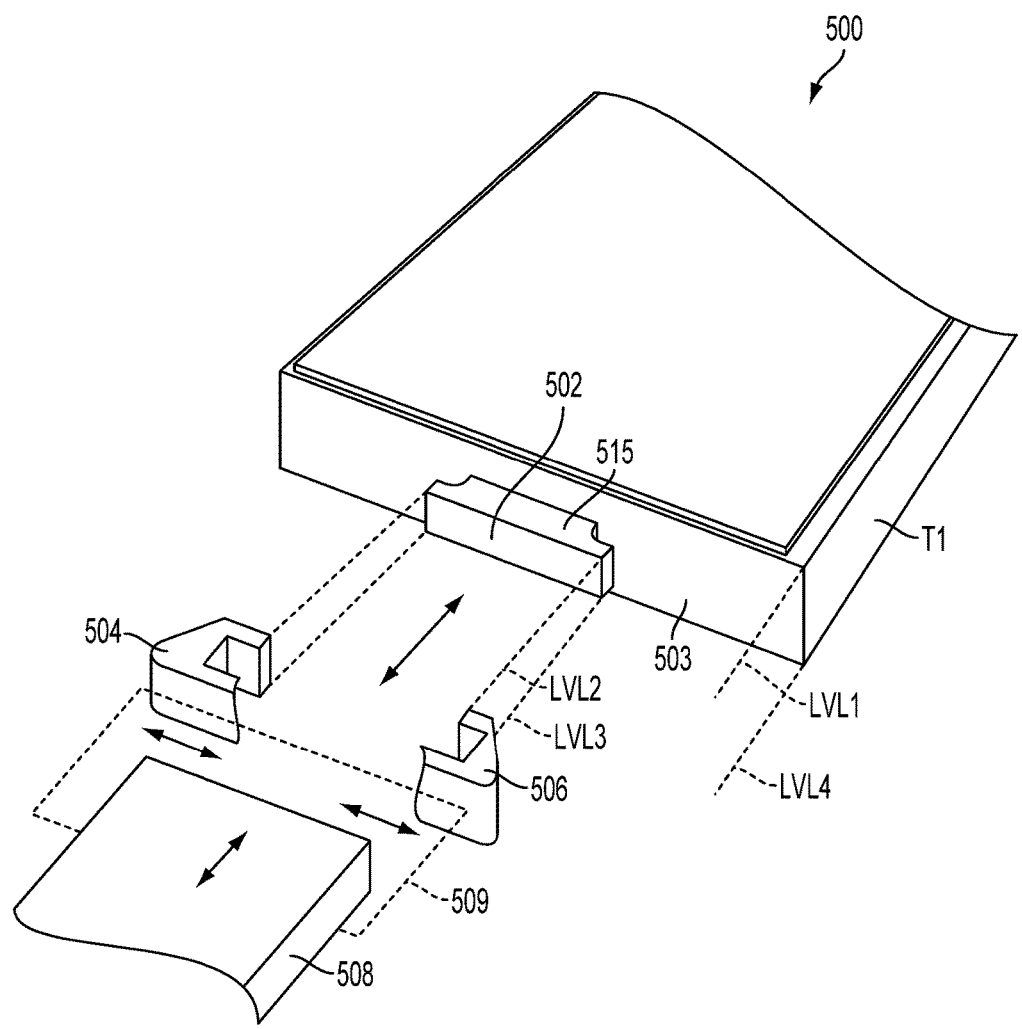
FIG. 12 is an isometric view of a grip assembly that is a part of an end effector located within the sorter, in accordance with various embodiments described in the present disclosure.

FIG. 12 is an isometric view of an embodiment of a grip assembly 500 that provides horizontal access to a tray. The grip assembly 500 is an example of the upper grip assembly 180 or the lower grip assembly 182 (FIG. 5A). A grip attachment 502 is attached to a front surface 503 of the tray T1. Gripping clamps 504 and 506 of the grip assembly 500 are attached to a grip base 508 via a grip connector 509. The grip base 508, the grip connector 509, and the gripping clamps 504 and 506 are parts of the grip assembly 500. The grip base 508 is attached to the driving plate 302 (FIG. 8A).

In several embodiments, the gripping clamps 504 and 506 are C-shaped or nearly C-shaped.

In some embodiments, the grip connector 509 includes a sliding mechanism, e.g., rails, etc., that allow the gripping clamps 504 and 506 to slide along the rails. In various embodiments, the grip connector 509 includes pivot mechanisms and the gripping clamps 504 and 506 pivot with respect to the pivot mechanisms.

With the extension of the driving plate 302 (FIG. 8A) from the position P1 (FIG. 5A) to the position P2 (FIG. 5B), the grip assembly 500 extends with the driving plate 302. The gripping clamps 504 and 506 pivot with respect to the grip connector 509 to engage, e.g., form a hook connection with, etc., the grip attachment 502 to grip the tray T1. In embodiments in which slides are used to slide the gripping clamps 504 and 506, the gripping clamps 504 and 506 slide along the connector 509 to engage the grip attachment 502.

It should be noted that when a pitch between two trays at consecutive levels within the cassette 102 or the indexer 104 is low, the gripping clamps 504 and 506 to slide or pivot horizontally facilitates use of the low pitch. For example, the gripping clamps 504 and 506 do not use space between a level LVL 1 of the tray lid L1 and a level LVL 2 of the top surface 515 of the grip attachment 502. As another example, the gripping clamps 504 and 506 do not use space between a level LVL3 of a bottom surface of the grip attachment 502 and a level LVL4 of a bottom of the tray T1.

Figure 13:
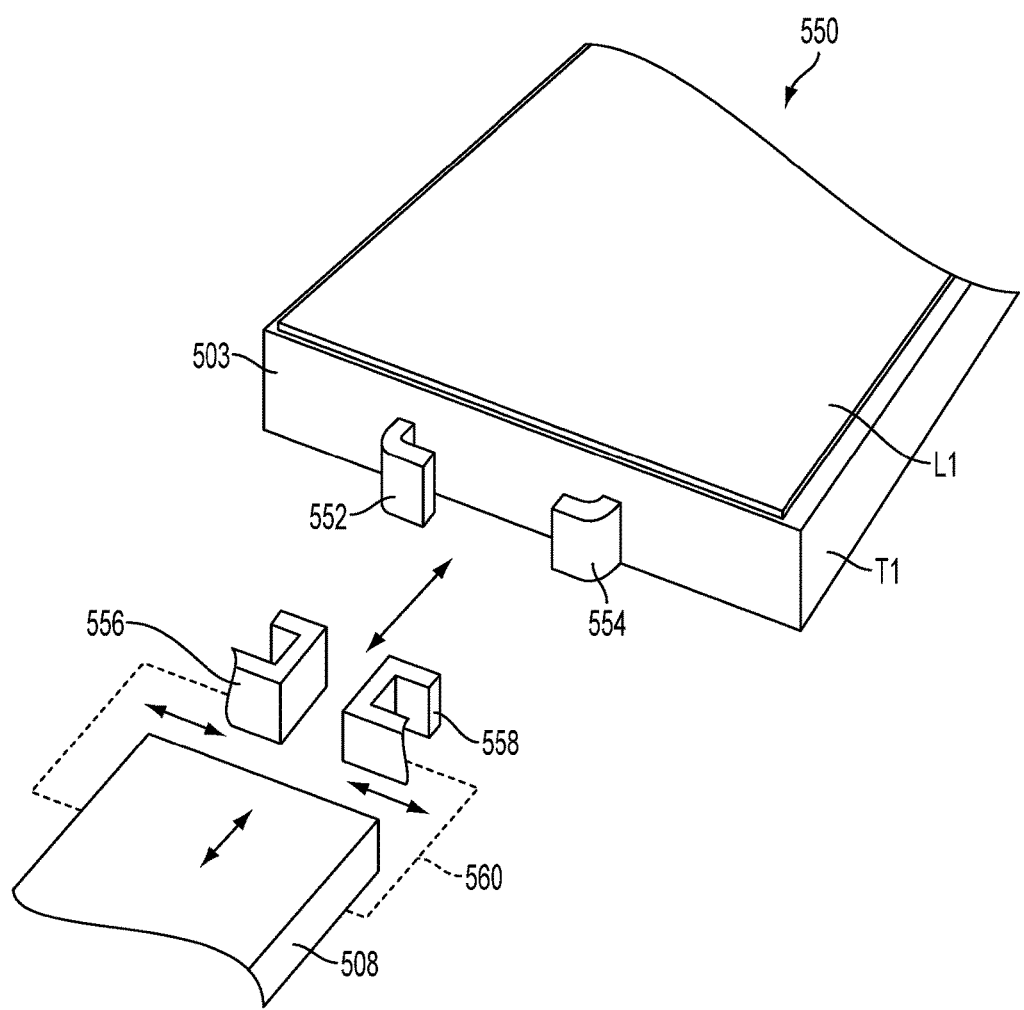
FIG. 13 is an isometric view of a grip assembly that is a part of an end effector located within the sorter, in accordance with some embodiments described in the present disclosure.

FIG. 13 is an isometric view of an embodiment of a grip assembly 550 that provides horizontal access to a tray. The grip assembly 550 is an example of the upper grip assembly 180 or the lower grip assembly 182 (FIG. 5A). Grip attachments 552 and 554 are attached to the front surface 503 of the tray T1. Gripping clamps 556 and 558 of the grip assembly 550 are attached to the grip base 508 via a grip connector 560. The grip base 508, the grip connector 560, and the gripping clamps 556 and 558 are parts of the grip assembly 550. The grip base 508 is attached to the driving plate 302 (FIG. 8A).

In some embodiments, the grip connector 560 includes a sliding mechanism, e.g., rails, etc., that allow the gripping clamps 556 and 558 to slide along the rails. In various embodiments, the grip connector 560 includes pivot mechanisms and the gripping clamps 556 and 558 pivot with respect to the pivot mechanisms.

In several embodiments, the gripping clamps 556 and 558 are C-shaped or nearly C-shaped. In various embodiments, the grip attachments 552 and 554 are L-shaped or nearly L-shaped.

With the extension of the driving plate 302 from the position P1 to the position P2, the grip assembly 550 extends with the driving plate 302. The gripping clamps 556 and 558 pivot with respect to the grip connector 560 to engage, e.g., form a hook connection with, etc., the corresponding grip attachments 552 and 554 to grip the tray T1. In embodiments in which slides are used to slide the gripping clamps 556 and 558, the gripping clamps 556 and 558 slide along the connector 560 to engage the grip attachments 552 and 554.

It should be noted that gripping clamps 556 and 558 provide the same advantages as that of the gripping clamps 504 and 506 (FIG. 12).

Figure 14A:
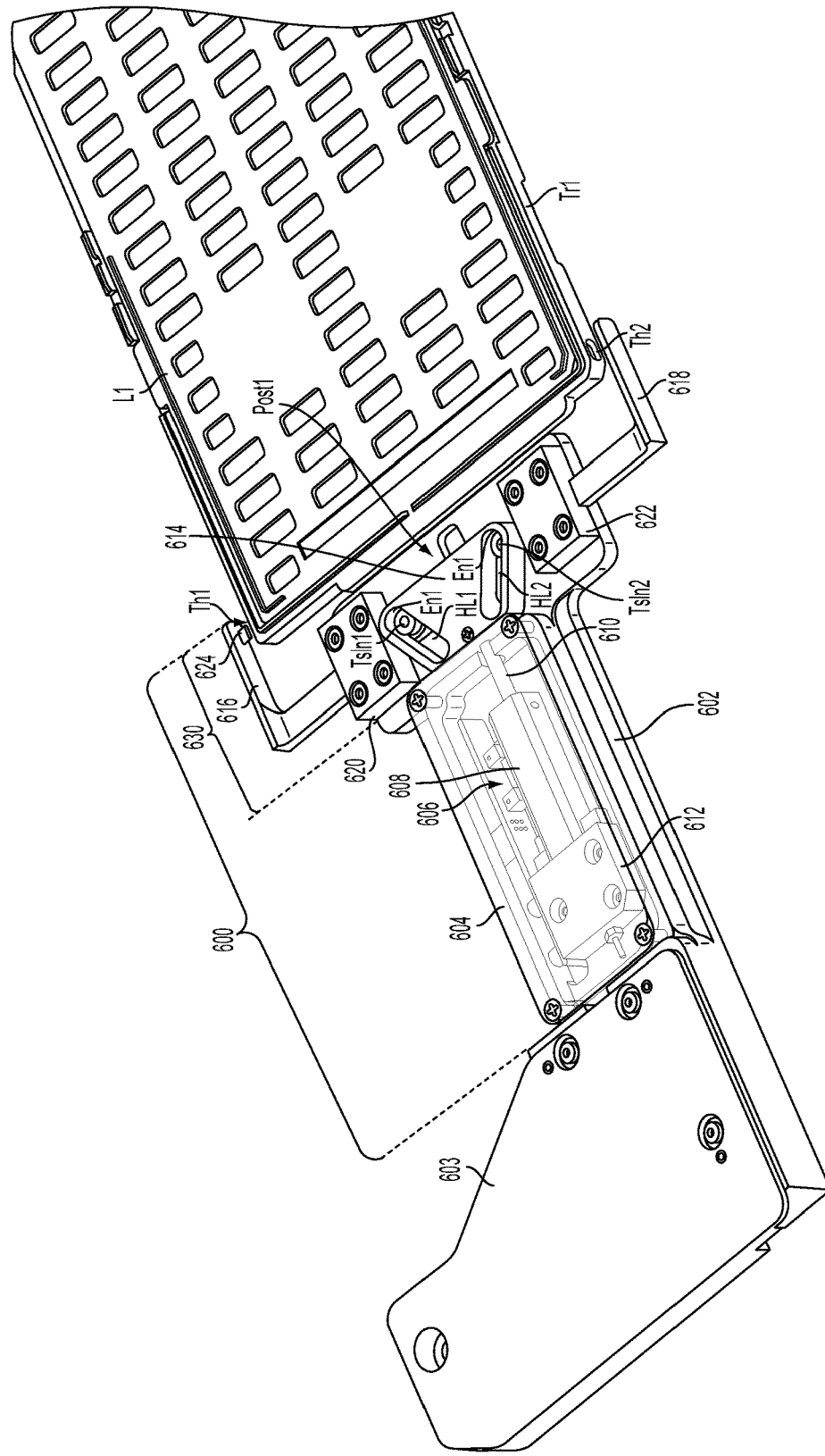
FIG. 14A is an isometric view of a grip assembly, in accordance with various embodiments described in the present disclosure.

FIG. 14A is an isometric view of an embodiment of a grip assembly 600. The grip assembly 600 is fixed to a driving plate 603 via an attachment mechanism. The grip assembly 600 includes a grip body 602 that is attached to the driving plate 603 via an attachment mechanism. The driving plate 603 is an example of the top driving plate 144 or the bottom driving plate 146 (FIG. 5A).

A cover 604 of the grip assembly 600 covers a portion of the grip body 602. For example, the cover 604 covers a piston mechanism 606. The piston mechanism 606 includes a piston housing 608 and a piston 610 that is slidable within the piston housing 608.

The piston housing 608 is attached to the grip body 602 via a block connector 612. The block connector 612 is attached to the grip body 602 via an attachment mechanism.

The piston 610 is fixedly attached to a slider 614 that is in a position "Post1". The slider 614 is retracted in the position Post1 when the piston 610 is retracted.

The slider 614 is attached via a translation mechanism Tsln1 to a left arm 616 and is attached via a translation mechanism Tsln2 to a right arm 618. In some embodiments, the arms 616 and 618 are referred to herein as a gripper. The translation mechanism Tsln1 translates within a through hole HL1 of the slider 614 and the translation mechanism Tsln2 translates within a through hole HL2 of the slider 614. As shown, each translation mechanism Tsln1 and Tsln2 is at an end Ent of the slider 614.

A portion of the left arm 616 lays within a slide block 620 and a portion of the right arm 618 lays within a slide block 622. A left extension 624 extends from an inner surface of the left arm 616 and a right extension 626, shown below in FIG. 14F, extends from an inner surface of the right arm 618.

As shown, the left extension 624 is a part of the left arm 616 and the right extension 626 is a part of the right arm 618. In various embodiments, instead of being integral to the corresponding arms 616 and 618, the left extension 624 is attached to the left arm 616 and the right extension 626 is attached to the right arm 618.

A portion of the grip body 602, the slider 614, the translation mechanisms Tsln1 and Tsln2, the slide blocks 620 and 622, the arms 616 and 618, and the extensions 624 and 626 are parts of a grip mechanism 630, which is a part of the grip assembly 600.

A tray Tr1 that is about to be gripped by the grip assembly 600 or just released by the grip assembly 600 includes through holes Th1 and Th2. The through holes Th1 and Th2 are located at opposite edges of the tray Tr1.

Figure 14B:
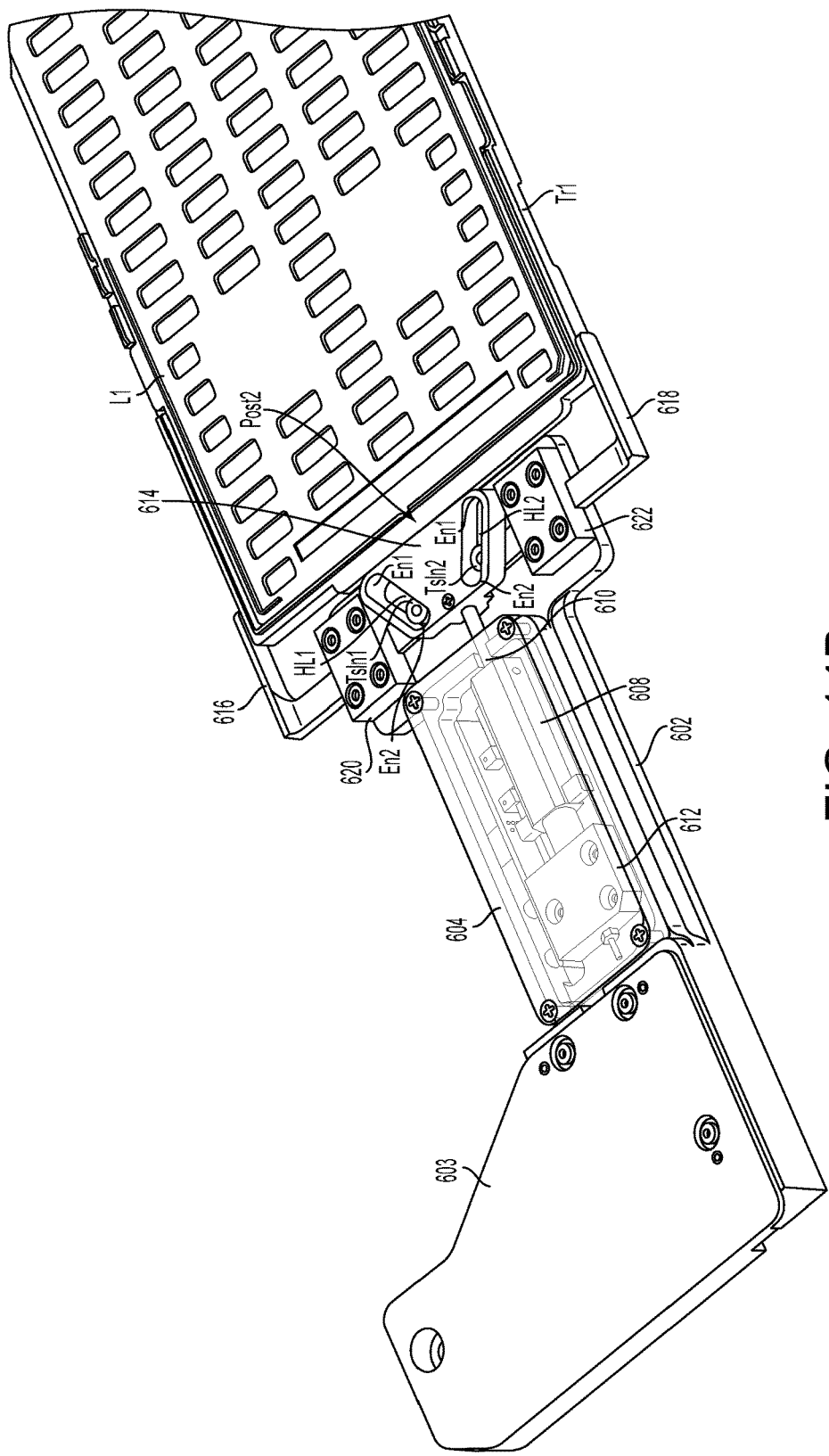
FIG. 14B is an isometric view of the grip assembly of FIG. 14A when the grip assembly has gripped a tray, in accordance with several embodiments described in the present disclosure.

FIG. 14B is an isometric view of an embodiment of the grip assembly 600 when the grip assembly 600 has gripped the tray Tr1. When the piston 610 extends from the piston housing 608 and is not in the retracted position, the translation mechanism Tsln1 translates within the through hole H1 from the end Ent to a location closer to an opposite end En2 of the slider 614 and the translation mechanism Tsln2 translates within the through hole H2 from the end Ent to a location closer to an opposite end En2 of the slider 614.

The translations of the translation mechanisms Tsln1 and Tsln2 within the corresponding through holes HL1 and HL2 from the ends Ent to locations closer to opposite ends En2 of the slider 614 contracts the arms 616 and 618 to extend the extensions 624 and 626 (FIGS. 14A and 14F) within the corresponding through holes Th1 and Th2 (FIG. 14A) of the tray Tr1. As the arms 616 and 618 contract towards each other to move in a horizontal direction, the arms 616 and 618 slide within the corresponding slide blocks 620 and 622.

When the extensions 624 and 626 extend via the corresponding through holes Th1 and Th2 of the tray Tr1, the tray Tr1 is gripped by the grip assembly 600.

Similarly, in an opposing motion, the piston 610 is retracted into the piston housing 608. When the piston 610 retracts into the piston housing 608, the slider 614 retracts from the position Post2 to the position Post1. As the slider 614 retracts from the position Post2 to the position Post1, the translation mechanisms Tsln1 and Tsln2 slide within the corresponding through holes HL1 and HL2 from the ends En2 towards the opposite ends Ent of the slider 614.

As the translation mechanisms Tsln1 and Tsln2 slide within the corresponding through holes HL1 and HL2 towards the ends En1, the arms 616 and 618 extend outward in a horizontal direction to extend the extensions 624 and 626 outside of the corresponding through holes Th1 and Th2 to release the tray Tr1 from grip of the grip assembly 600. As the arms 616 and 618 extend outward away from each other, the arms 616 and 618 slide within the slide blocks 620 and 622.

It should be noted that the grip assembly 600 grips the tray Tr1 by using a horizontal motion of the arms 616 and 618 towards and away from the tray Tr1. The horizontal motion of the arms 616 and 618 to grip trays may facilitate a lower pitch between levels of the cassette 102 or the indexer 104 compared to vertical motion of arms of a grip assembly to grip trays.

Figure 14C:
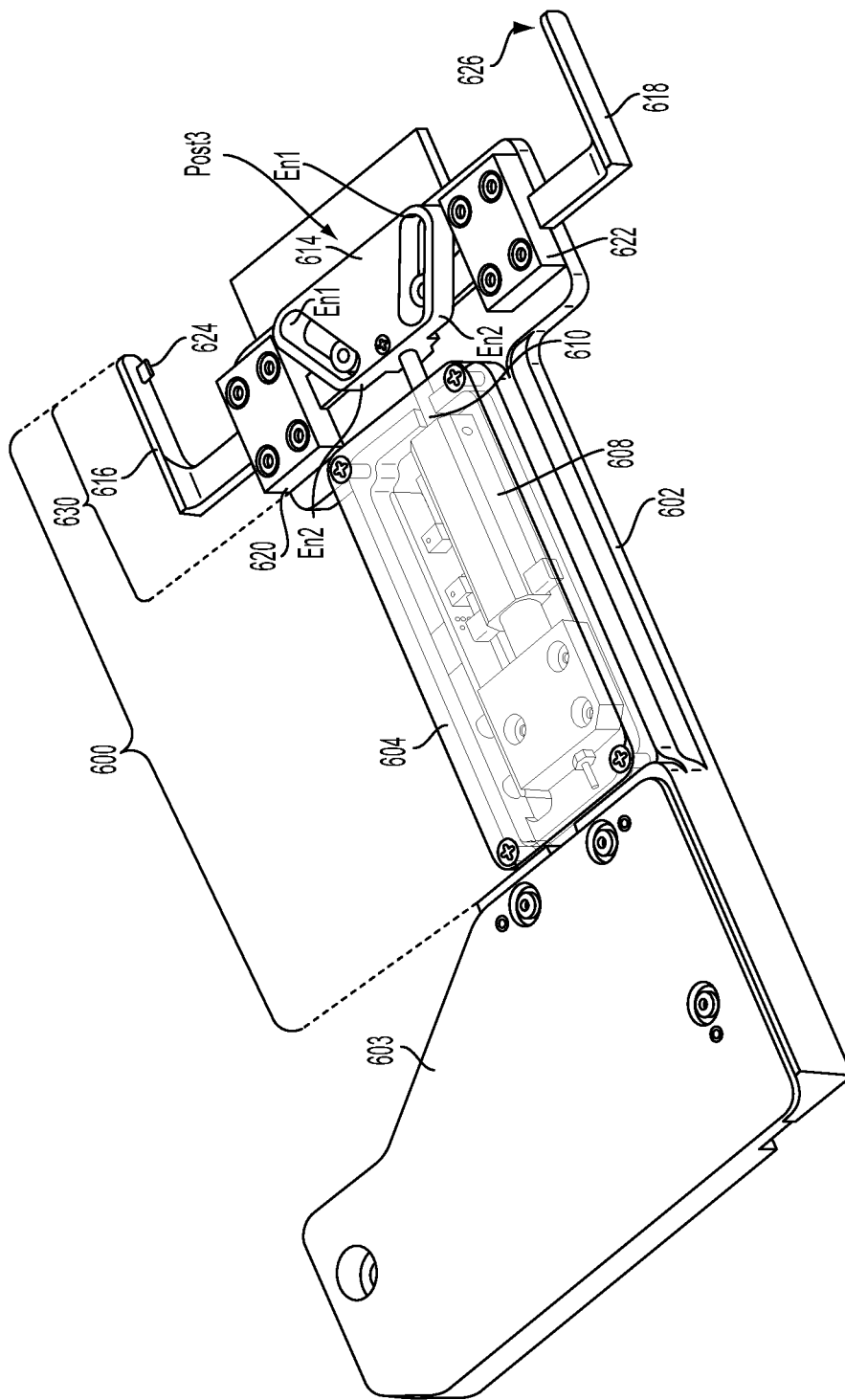
FIG. 14C is an isometric view of the grip assembly of FIG. 14A in a position in which the grip assembly may have missed gripping a tray, in accordance with some embodiments described in the present disclosure.

FIG. 14C is an isometric view of an embodiment of the grip assembly 600 in a position Post3. The piston 610 extends further out from the piston housing 608 to extend the slider 614 from the position Post2 to the position Post3. As the slider 614 translates, e.g., slides on the grip body 602, from the position Post2 to the Post3, the translation mechanisms Tsln1 and Tsln2 move to the ends En2. In some embodiments, the move to the ends En2 may indicate a miss of gripping a tray Tr1.

Figure 14D:
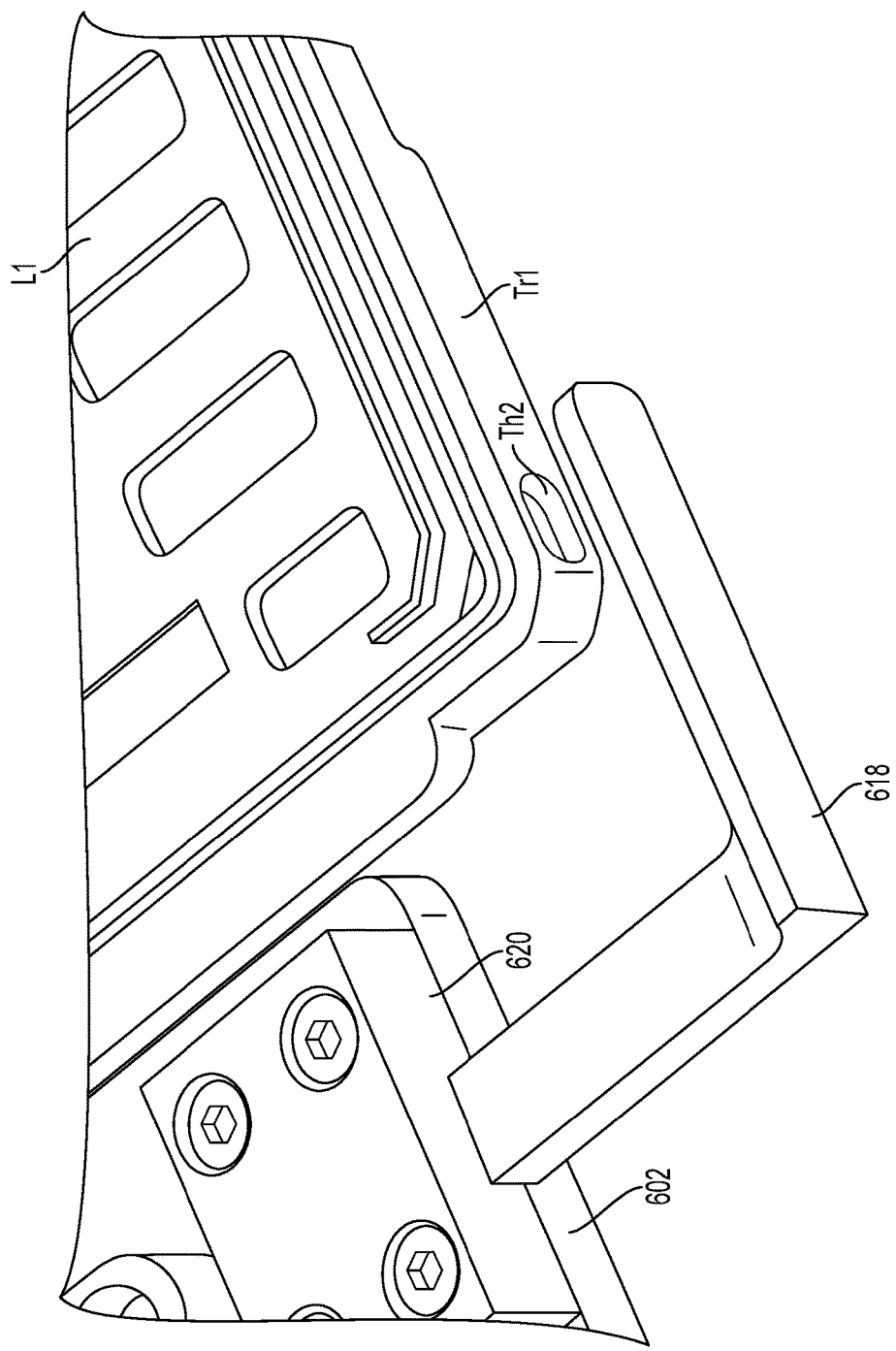
FIG. 14D is an isometric view of a right arm of the grip assembly of FIG. 14A, in accordance with several embodiments described in the present disclosure.

FIG. 14D is an isometric view of an embodiment of the right arm 618 of the grip assembly 600. The right arm 618 is about to grip the tray Tr1 or has just released the tray Tr1.

Figure 14E:
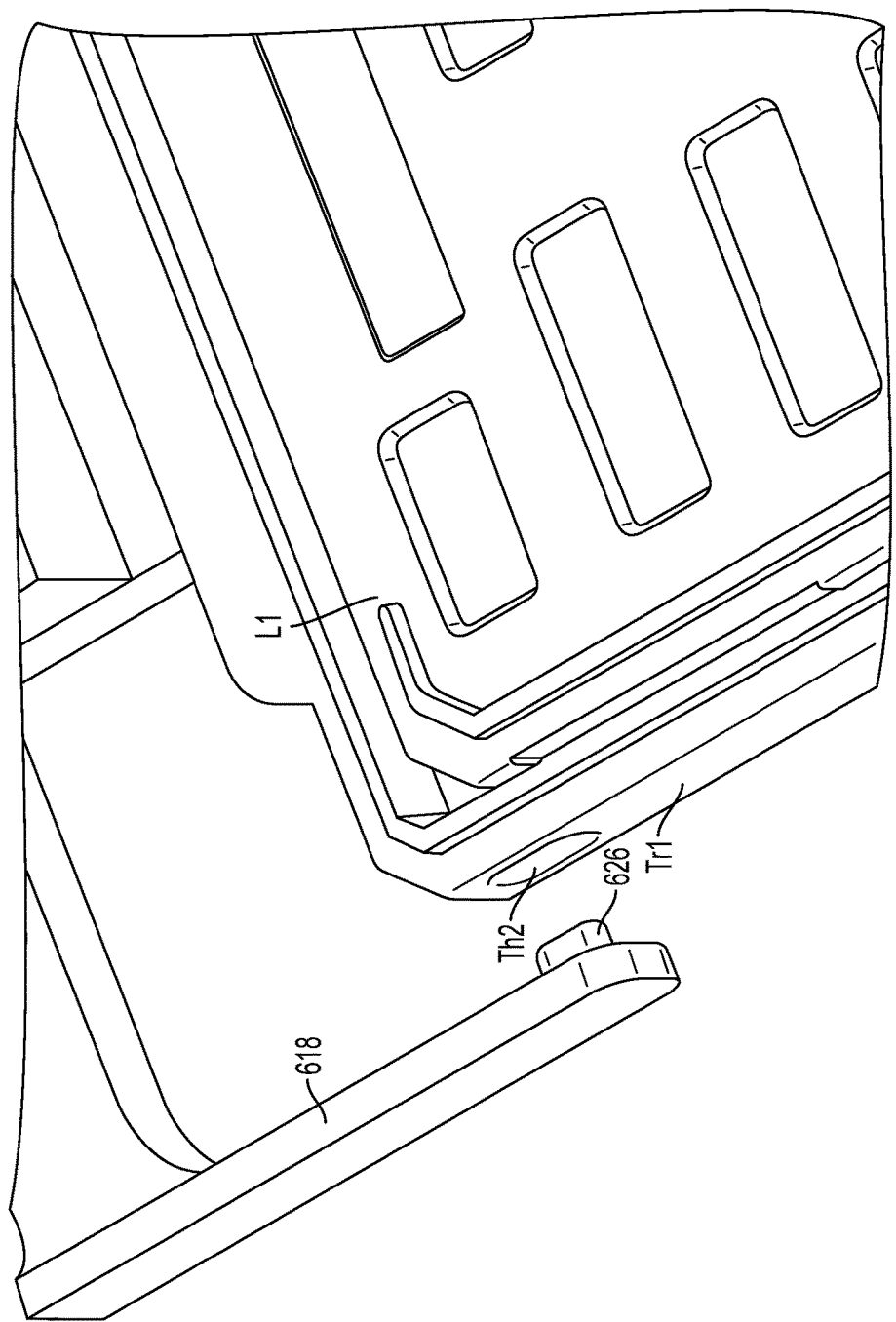
FIG. 14E is an isometric view of the right arm of FIG. 14D, in accordance with several embodiments described in the present disclosure.

FIG. 14E is an isometric view of an embodiment of the right arm 618 of the grip assembly 600. The right arm 618 is about to grip the tray Tr1 or has just released the tray Tr1. As shown, the right extension 626 is about to extend within the through hole Th2 or has just retracted from the through hole Th2.

Figure 14F:
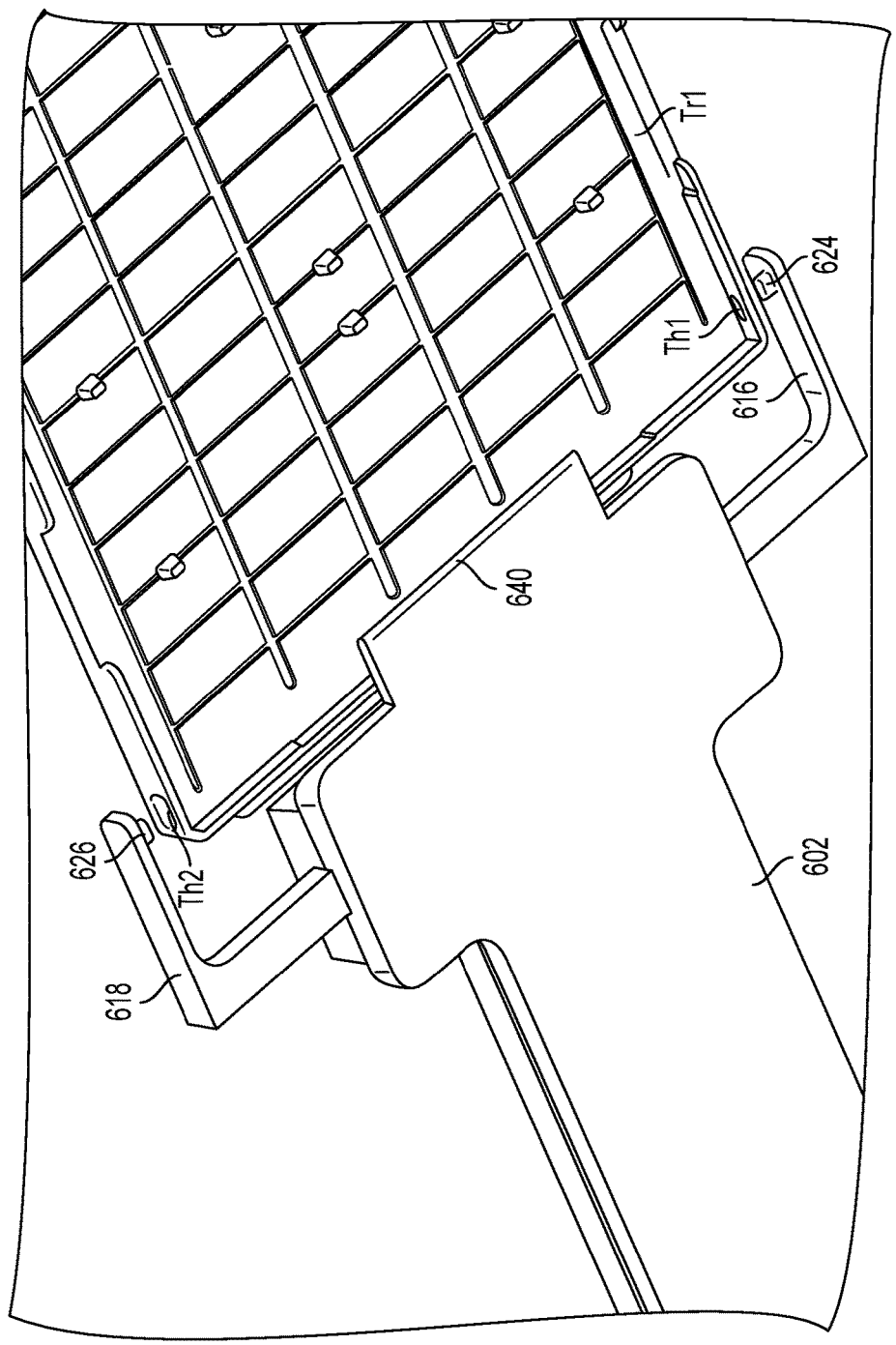
FIG. 14F is a bottom isometric view of an embodiment of a grip body of the grip assembly of FIG. 14A in which the grip assembly is about to grip a tray or has just released the tray, in accordance with various embodiments described in the present disclosure.

FIG. 14F is a bottom isometric view of an embodiment of the grip body 602 and the arms 616 and 618. As shown, the grip body 602 includes a grip tab 640 that supports the tray Tr1 when the tray Tr1 slides from the cassette 102 or the indexer 104 (FIG. 1) to the sorter 106 (FIG. 1) or from the sorter 106 to the cassette 102 or the indexer 104. The arms 616 and 618 are about to grip the tray Tr1 or has just released the tray Tr1.

Figure 14G:
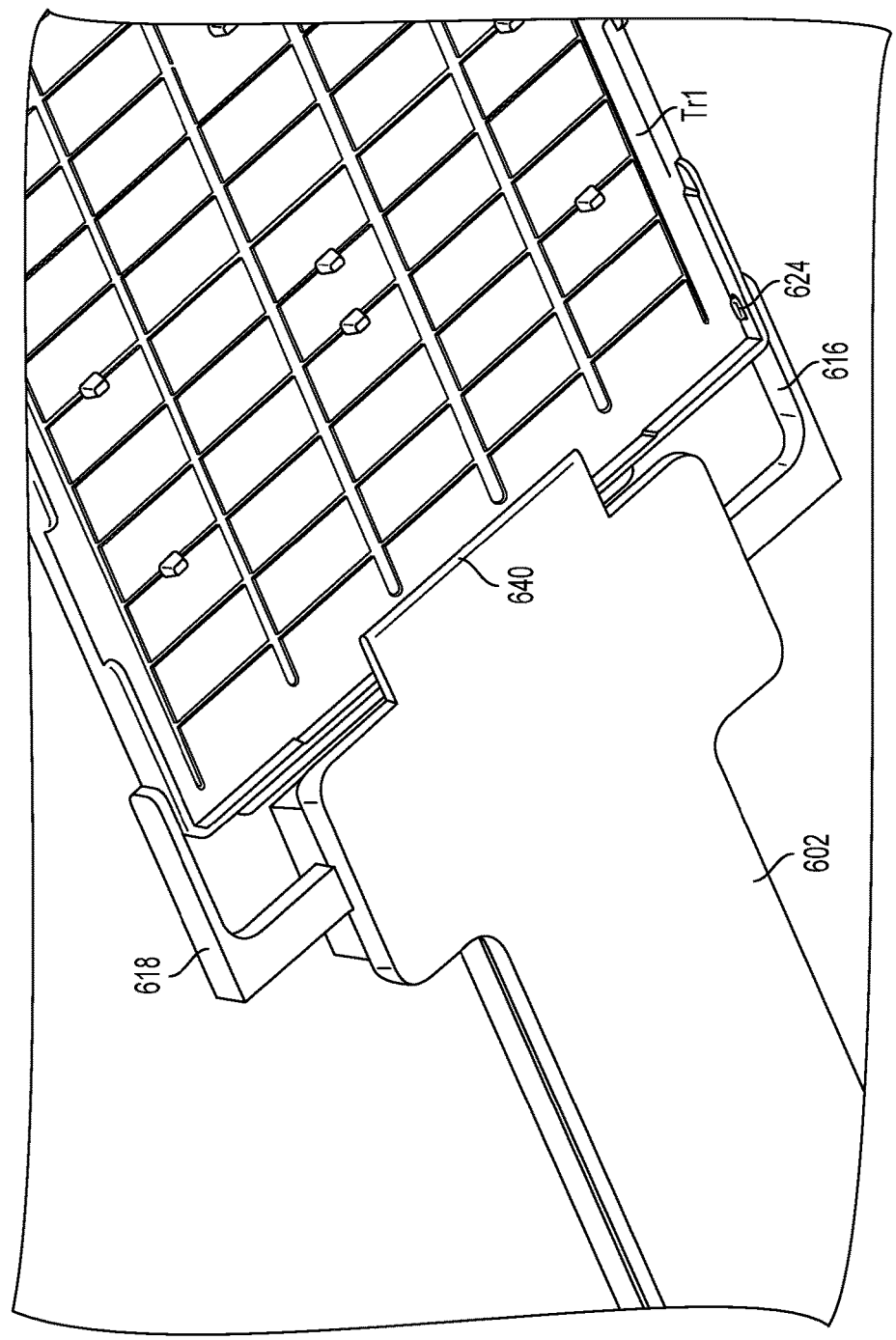
FIG. 14G is a bottom isometric view of an embodiment of the grip body of FIG. 14F in which the grip assembly has gripped a tray, in accordance with some embodiments described in the present disclosure.

FIG. 14G is a bottom isometric view of an embodiment of the grip body 602 and the arms 616 and 618. The arms 616 and 618 grip the tray Tr1 when the right extension 626 extends through the through hole Th2 and the left extension 624 extends through the through hole Th1.

Although some of the above-described embodiments describe trays covered with tray lids, in some embodiments, a tray is used without a tray lid. For example, a tray is not covered with a tray lid.

It is noted that although some of the above-described embodiments include the tray engine 102 within the sorter 106 (FIG. 1A) or the EFEM 156, in some embodiments, the tray engine 102 is located within a tool that is described with reference to FIG. 3.

Moreover, in various embodiments, instead of using information identifying a tray, information identifying a tray lid may be used. For example, a tray lid has a tag or imprints that identifies the tray and the tag is captured by a camera or read by an RFID reader. In various embodiments, both a tray and a tray lid have tags that identify the tray and the tray lid, and information on the tags is captured with a camera or with an RFID reader.

Also, in some embodiments, the sorter 106 has storage devices to buffer trays and/or tray lids as the trays and/or tray lids are transferred between the cassette 102 and the indexer 104.

While the present disclosure in terms of several embodiments, it will be appreciated that those skilled in the art upon reading the preceding specifications and studying the drawings will realize various alterations, additions, permutations and equivalents thereof. Therefore, it is intended that the present disclosure includes all such alterations, additions, permutations, and equivalents as fall within the true spirit and scope of the invention.

The invention claimed is:

1. A wafer tray sorter comprising:
a first wall having a plurality of doors, wherein the doors are configured to open to create a plurality of openings in the first wall, wherein one of the openings is configured to interface with a cassette having one or more trays, wherein one of the trays is configured to carry a wafer,
a second wall that faces the first wall, wherein the second wall includes a plurality of slots, wherein one of the slots is configured to interface with an indexer; and
a tray engine configured to move in a linear direction between the first wall and the second wall to facilitate a transfer of the one of the trays, wherein the transfer occurs between the one of the openings and one of the slots,
wherein one of the doors is coupled to a detector configured to detect the one of the trays,
wherein the detector is configured to identify the one of the trays by reading a plurality of numbers, or a barcode, or a combination of a barcode and numbers, or an EZ code, or an alphanumeric code on the one of the trays.

2. The sorter of claim 1, wherein the detector is a sensor, wherein the sensor is configured to detect whether the one of the trays is present within the cassette.

3. The sorter of claim 1, wherein the detector is a camera, wherein the camera is configured to identify the one of the trays.

4. The sorter of claim 1, wherein the detector is attached to a top surface of the one of the doors, wherein the one of the doors is configured to slide down to form the one of the openings.

5. The sorter of claim 1, wherein the detector is attached to a bottom surface of the one of the doors, wherein the one of the doors is configured to slide up to form the one of the openings.

* * * * *